United States Patent [19]

Fiori et al.

[11] Patent Number: 5,299,138
[45] Date of Patent: Mar. 29, 1994

[54] DESK TOP SPECTRUM ANALYZER

[75] Inventors: Charles E. Fiori, McLean, Va.; Carol R. Swyt, Germantown, Md.

[73] Assignees: The United States of America as represented by the Secretary of Commerce; The United States of America as represented by the Department of Health and Human Services, both of Washington, D.C.

[21] Appl. No.: 743,072

[22] Filed: Aug. 9, 1991

[51] Int. Cl.$^5$ ............................................. G06F 15/20
[52] U.S. Cl. .................................. 364/498; 364/485; 250/390.07
[58] Field of Search ............ 364/485, 487, 498, 551.01; 250/310, 390.07, 370.07

[56] References Cited

U.S. PATENT DOCUMENTS

| | | | |
|---|---|---|---|
| 4,093,991 | 6/1978 | Christie, Jr. et al. | 364/498 |
| 4,322,807 | 3/1982 | Chamran et al. | 364/498 |
| 4,365,303 | 12/1982 | Hannah et al. | 364/498 |
| 4,560,275 | 12/1985 | Goetz | 356/326 |
| 4,568,186 | 2/1986 | Yoshimura et al. | 364/498 |
| 4,642,778 | 2/1987 | Hieftje et al. | 364/498 |
| 4,703,437 | 10/1987 | Nishimura | 364/498 |
| 4,812,996 | 3/1989 | Stubbs | 364/485 |
| 4,988,872 | 1/1991 | Nagatsuka et al. | 250/310 |
| 5,023,804 | 1/1991 | Hoult | 364/498 |
| 5,046,846 | 9/1991 | Ray et al. | 364/498 |
| 5,121,337 | 9/1992 | Brown | 364/498 |

OTHER PUBLICATIONS

Fiori, C. E. and Swyt, C. R., "The Use of Theoretically Generated Spectra To Estimate Detectability Limits and Concentration Variance In Energy-Dispersive X-Ray Microanalysis", Microbeam Analysis-1989, P. E. Russell, Editor, San Francisco Press, Inc. (C) 1990.
Swyt, C. R. and Firoi, C. E., "Desk Top Generation And Analysis of Spectra" Electron Microscopy 1990, Proceedings of the XIIth International Congress for Electron Microscopy, 12-18, Aug. 1990, vol. 2: Analytical Sci., Peachey and Williams, San Francisco Press (C) 1990.
"EDS Quantitation And Application To Biology" by Hall and Gupta.
"Simplex Optimization Of Variables" *Analytical Chemistry* Mar. 1973 by Deming and Morgan.
"Quantitative Electron Probe Analysis:Problems And Solutions" *Ultramicroscopy* 11 (1983) North-Holland Publishing by Kitazawa, Shuman and Somlyo.
*X-Ray Fluorescence Analysis Of Environmental Samples* Edited by Dzubay, 1977 Ann Arbor Science Publishing, "A Modification of Least Square Fitting Method which Provides Continuum Suppression" by Schamber.
"Experience With Multiple-Least-Squares Fitting With Derivative References" by McMillan, Baughman and Schamber, *Microbeam Analysis-1985*.
"Linear and Non-linear Peak Fitting in Energy-dispersive X-Ray Fluroescence" *X-Ray Spectrometry*, vol. 8, No. 3, 1979 by Nullens, Van Espen and Adams.
"Smoothing and Differentiation of Data by Simplified Least Squares Procedures" from *Analytical Chemistry*, Jul. 1964, by Savitzky and Golay.

(List continued on next page.)

[57] ABSTRACT

A control system emulates an X-ray spectrum generation and analyzing system on a computer by emulating the experimental apparatus, emulating the experimental geometry between elements of the experimental apparatus and emulating a material sample within the experimental apparatus including the emulated material sample's physical properties. The control system allows an operator generate theoretical spectra of material samples based on the emulated experimental apparatus and the physical characteristics of the emulated material sample. The control system also allows the operator to compare the generated theoretical spectrum to a real spectrum acquired from the experimental system and sample which have been emulated. Thus, the operator can easily determine the sufficiency of the emulation of the experimental set-up. The control system further allows the operator to analyze the generated theoretical spectra. Thus, the operator can determine the sufficiency of the experimental set-up in determining the character and composition of the real material sample.

22 Claims, 65 Drawing Sheets

"Application Hints for Savitzky-Golay Digital Smoothing Filters" *Analytical Chemistry*, Sep. 1981 by Bromba and Ziegler.

"Some Problems With Quantitative Electron Probe Microanlysis" *Electron Probe* by Philibert and Tixier.

"The Application Of A Numerical Procedure In The Calculation Of The Atomic-Number Correction In Electron Probe Microanalysis" *Microbeam Analysis 1989* by Myklebust and Fiori.

"Revision of the Method for Continuum Fluorescence Correction" *Proceedings of Symposium on Quantitative Electron-Probe Analysis*, W. Germany, Oct. 1972 by Springer.

"Background corrections for quantitative electron microprobe analysis using a lithium drifted silicon x-ray detector" *Journal Physics E: Scientific Instruments*, vol 6, 1973, Gr. Britain, by Ware and Reed.

"Quantitative X-Ray Energy Dispersive Analysis with the Transmission Electron Microscope" *X-Ray Spectrometry*, 1975, vol. 4, by Geiss and Huang.

"Quantitative Electron Microprobe Analysis Using a Lithium Drifted Silicon Detector" *X-Ray Spectrometry*, vol. 2, 1973, by Reed and Ware.

"The Atomic Number Dependence of the X-Ray Continuum Intensity and the Practical Calculation of Background in Energy Dispersive Electron Microprobe Analysis" *X-Ray Spectrometry*, vol. 4, 1975 by Smith, Gold and Tomlinson.

"Recent Experimental Values for K Shell X-Ray Fluorescence Yields" *X-Ray Spectrometry*, vol. 4, 1975 by Freund.

"$K\beta/K\alpha$ X-Ray Transistion-Probability Ratios for Element $18 \leq Z \leq 39$*" *Physical Review A*, Apr. 1972 by Slivinsky and Ebert.

"The Efficiency of Production of Characteristic X-radiation in Thick Targets of a Pure Element" *Cavendish Lab., University of Cambridge*, by Green and Cosslett.

"Theoretical Continuous X-Ray Energy and Polarization" *Physical Review*, Jun. 1945, by Kirkpatrick and Wiedmann.

"A Robust Method For Determining The Duane-Hunt Energy Limit From Energy Dispersive Spectra" by Myklebust, Fiori and Newbury.

NBS special publication 604, "Energy Dispersive X-Ray Spectrometry" published by the U.S. Department of Commerce/National Bureau of Standards, Jun. 1981.

"The Link Analytical News Letter, Issue 1" *Linkline* brochure.

"PortToPort" by Tracor Northern brochure.

"$K\beta/K\alpha$ Radiative-Transistion-Probability Ratios for Elements of Low Atomic Numbers in Amorphous and Crystal Forms" *Physical Review A*, Dec. 1972 by Salem, Falconer and Winchell.

*Primary Examiner*—Thomas G. Black
*Assistant Examiner*—Tan Q. Nguyen
*Attorney, Agent, or Firm*—Stephen J. Roe The EXPERIMENT HEADER includes the information in the Expt_InfoRec and the Plot_infoRec.

The SPECTRUM HEADER contains the information in the Spectrum_InfoRec, including the Element_InfoRec, and Acq_InfoRec:

A spectrum includes the SPECTRUM HEADER and the Spectrum_counts.

An experiment file will contain the EXPERIMENT HEADER, and n spectra( n≥1 ) spectrum files Each spectrum image memory will contain a Work_Spectrum.

```
Expt_InfoRec            - RECORD
        LastSpect               : Integer;    { last Spectrum }
        FirstSpec               : Integer;    { first spectrum }
        Specimen_ID             : String (50);
        MCA_Filename            : String (25);
        Specimen_Comment_Field  : Str255;
        PassWord                : String(25);  { To unlock the below "protect") 
        File_Protect            : Boolean;
        Analyst                 : String(50);
        DetectorID              : real;
        Azimuth                 : real;       { degrees }
        Elevation               : real;       { degrees }
        Detector_Area           : real;       { cm sq }
        Detector_Thickness      : real;       { nm }
        C_Thickness             : real;       { um }
        Diamond                 : real;       { um }
        Mylar                   : real;       { um }
        BN_Thickness            : real;       { um }
        SiN_Thickness           : real;       { um }
        Ice_Thickness           : real;       { um, as pure oxygen }
        Au_Thickness            : real;       { um }
        Al_Thickness            : real;       { um }
        Be_Thickness            : real;       { um }
        Si_Thickness            : real;       { um }
        spare5                  : real;
        spare6                  : real;
        spare4                  : real;
        dE.                     : real;
        Si_Resolution           : real;       { eV at Mn K alpha }
```

FIG.21

```
              Energy_Intercept          : real;      { y intercept in eV }
              Energy_Slope              : real;      { }
              Number_of_Channels        : integer;
              kV                        : real;
              Detector_Tilt             : real;      { Beta }
              Quantum                   : real;
              Spare2                    : Boolean;   { the Demo file boolean }
              Spare3                    : Integer;
    end;

Plot_InfoRec              =RECORD
              Plot_Connected            : Integer;
              Plot_Symbol               : Integer;
              Spectrum_Color            : Array {1..3} of Integer;  {Red, Green, Blue}
    end;
```

FIG.21 Cont.

```
Acq_InfoRec              = RECORD
    Probed_Area              : real;     { cm sq. to calculate current density }
    X_Position               : real;     { dimensionless }
    Y_Position               : real;     { dimensionless }
    Specimen_Temperature     : real;
    Vacuum                   : real;
    Begin_Faraday            : real;     { nA }
    End_Faraday              : real;     { nA }
    Begin_Time               : DateTimeRec;
    Real_Time                : real;           { The time on the wall }
    Live_Time                : real;
    Slow_Channel_Counts      : Longint;  { Represents total out counts }
    Medium_Channel_Counts    : Longint;  { If UTW. Approx. input counts below 1 keV }
    Fast_Channel_Counts      : Longint;  { Represents total input counts above 1 keV }
    RequestedLiveTime        : Longint;
    ActualLiveTime           : Longint;
    Acquiring                : Boolean;
    LLD                      : INTEGER;  { Acquisition setup dialog box }
    Offset                   : INTEGER;  { Acquisition setup dialog box }
    PulseProcessorType       : INTEGER;
    PulseProcessorSetting    : INTEGER;
end:

Spectrum_InfoRec         = RECORD
    Spectrum_Type            : String {4};
    Spectrum_Comment_Field   : Str255;
    Spectrum_Number          : Integer; { Position of spectrum in a collection }
    Spectrum_Class           : String {25};
    Theoretically_Generated  : Boolean;
    This_is_a_Standard       : Boolean;
    BkgSubtracted            : Boolean;
    Maximum_Counts           : real;
    Minimum_Counts           : real;

X_Tilt                   : real;     { }
    Y_Tilt                   : real;     { }
    Take_Off_Angle           : real;     { can be SPARE: this is calculated }
    Spec_Detector_Distance   : real;     { mm }
    Spare                    : real;
    Specimen_Thickness       : real;     { cm }
```

FIG.22

```
        Specimen_Density       : real;   { g/cm sq. }
        Number_of_Elements     : Integer;
        Element_Info           : array { 1..MaxNumPks } of Element_InfoRec:
        Average_Z              : real;
        Spare1                 : real;
        Spare2                 : Boolean; { used to denote demo spectrum }
        Spare3                 : Integer;
        END;
Element_InfoRec                = RECORD
        Atomic_number          : Integer;
        Spare1                 : real;
        Weight_Fraction        : real;  { We will always store as wt fr }
        Spare2                 : real;
        Valence                : real;
    end;
Spectrum_counts                = ARRAY {1..8192} OF Real;

Work_Spectrum                  = RECORD
        Expt_Info              : Expt_InfoRec;
        Plot_Info              : Plot_InfoRec;
        Spectrumstuff          : Spectrum_Structure;
        S                      : Spectrum_counts;
    END;
```

FIG.22 Cont.

The ML SETUP FILES include the information in ML_Stuff.

```
Deriv_info = record        { used to store info about derivatives to use }
        Z                  : integer;
        Family             : string{1} {Family_Type};
        use1st             : boolean;
        use2nd             : boolean;
    end;

ML_Stuff           =    record
    number_of_files              : integer;
    The_File_Name                : Array{1..5} of fnamestr;  { reference files used }
    refindex                     : NPKARRAY;
    number_of_MLwindows          : integer;
    number_of_refs               : integer;
    ML_LoeV                      : PKARRAY;    { low energy of each peak ROI }
    ML_HieV                      : PKARRAY;    { high energy of each peak ROI }
    number_of_derivs             : integer;
    window_element               : NPKARRAY;   { atomic number of each element }
    weFamily                     : Array {1..MaxNumPks} of string{1} {Family_Type};
    Number_of_refs_in_Window     : NPKARRAY;
    number_of_derivs_Window      : NPKARRAY;
    First_Ref                    : NPKARRAY;
    Last_ref                     : NPKARRAY;
    First_Deriv                  : NPKARRAY;
    Last_deriv                   : NPKARRAY;
    DoFirst                      : Array {1..MaxNumPks} of boolean;
    DoSecond                     : Array {1..MaxNumPks} of boolean;
    BkgLo                        : integer;
    BkgHi                        : integer;
    BkgArea                      : real;
    end;
```

FIG. 23

A file of REFERENCES contains the following information for each reference distribution.

```
References_Rec  = RECORD
    Data                : realWindowArray;  { the ref: segment of a spectrum }
    area                : REAL;
    dE                  : REAL;
    kV                  : REAL;
    Intercept           : REAL;
    Slope               : REAL;
    FWHM_Mn             : REAL;
    Atomic_Number       : integer;
    Family              : string[1];
    Begin_Energy        : REAL;  { low energy of the segment of a spectrum in eV }
    End_Energy          : REAL;  { high energy of the segment in eV }
    Standard_Used       : Str255; { name of the spectrum file }
    Comments            : Str255;
END;
```

The XRAY DATA FILE contains the density and atomic weight of each element; for every characteristic line: atomic number, wavelength, and line weight; and the wavelengths of all absorption edges.

FIG.23 Cont.

A Fit RESULTS FILE contains the information in Expt_InfoRec. Spectrum_Structure.
Fit_Params_Type, and Fit_Result_Type for each spectrum analyzed.

```
Fit_Params_Type    = RECORD
                     Fit_Procedure      : STRING {2}
                     Ref_FileName       : array {1..5} of fnamestr;
                     Toler              : real;
                     DEN                : real;
                     DFWHM              : real;
                     switch             : real;
                     Chosen_ROI_Lo      : integer;
                     Chosen_ROI_Hi      : integer;
                     Number_of_Windows  : integer;
                     Number_of_Peaks    : integer;    { # in all windows }
                     First_in_Roi       : ARRAY {1..MaxNumPks} OF integer;
                     Fitting_Roi_Lo     : ARRAY {1..MaxNumPks} OF real;
                     Fitting_Roi_Hi     : ARRAY {1..MaxNumPks} OF real;
                     Atomic_Number      : ARRAY {1..MaxNumPks} OF integer;
                     Siegbahn           : ARRAY {1..MaxNumPks} OF Str_5;
                     Ref_Index          : ARRAY {1..MaxNumPks} OF integer;
                     END;

Fit_Result_Type    = RECORD
                     Iterations         : ARRAY {1..MaxNumPks} OF integer;
                     Response           : ARRAY {1..MaxNumPks} OF real;
                     FWHM_Mn            : ARRAY {1..MaxNumPks} OF real;
                     area               : ARRAY {1..MaxNumPks} OF real;
                     Err_or_Energy      : ARRAY {1..MaxNumPks} OF real;
                     Peak_to_Local_Bkg  : ARRAY {1..MaxNumPks} OF real;
                     Peak_to_Chosen_Bkg : ARRAY {1..MaxNumPks} OF real;
                     conc               : ARRAY {1..MaxNumPks} OF real;
                     Chosen_Norm_Bkg    : real;
                     END;
```

FIG. 24

```
A HALL FILE contains the information in Hall_Stuff and Hall Hall_OutStuff.
Hall setup file contains the information in Hall_Stuff.
Hall_Stuff = record
    do_bulk      : boolean;
    get_film     : boolean;
    get_grid     : boolean;
    get_stds     : boolean;
    Bulk_z       : integer;
    Bulk_Line    : Str_5;
    FilmCorr     : real;
    BulkFactor   : real;
    Average Z    : real;
    FilmFile     : fnamestr;
    BulkFile     : fnamestr;
    number_of_peaks : integer;
    Atomic_Number   : array {1..MaxNumPks} of integer;   { which peaks to quantitate }
    Siegbahn        : ARRAY {1..MaxNumPks} of Str_5;
    K_Factor        : array {1..MaxNumPks} of real;
    Std_File_Code   : array {1..MaxNumPks} of integer;
    Standard_files  : array {1..5} fnamestr;
end;
Hall_OutStuff = record
    do_M         : BOOLEAN;
    resultsname  : fnamestr;
    DTSAname     : string{25};
    class        : string{25};
    spectrum     : integer;
    z_Corr       : real;                                 { Calculated avg z }
    BulkBk       : real;                                 { bkg contribution from bulk source }
    Totbk        : real;                                 { bkg corrected for film and bulk contributions }
    conc         : array {1..MaxNumPks} of real;
    ptob         : array {1..MaxNumPks} of real;
    stdev        : array {1..MaxNumPks} of real;
end;
```

```
A ZAF FILE contains the information in ZAF_Stuff.
ZAF_Stuff = record
    Simplex_run          : boolean;            { all spectra - one of these two must be 1 }
    ML_run               : boolean;            { all spectra }
    Standard             : boolean;            { if spectrum is a standard this is 1 }
    Stoic_Diff           : boolean;            { 0 for element by difference or 1 if by stoic. }
    Num_elements         : integer;            { number of elements in specimen }
    Atomic_Number        : array{1..15} of integer;   { for each element in specimen }
    Atom_Wt              : array{1..15} of real;      { for each element in specimen }
    Valence              : array{1..15} of real;      { for each element in specimen }
    Siegbahn             : ARRAY{1..15} OF Str_5;     { x-ray line for quant. of each element }
    Std_Name             : array{1..15} of STRING{64};
                                               { for specimen - name of standard used to quant. each element }
    Pure_Standard_Intensity : array{1..15} of real;   { for standard - peak area }
    Concentration        : array{1..15} of real;
                                               { if std then wt.fr. of element.  if unknown then quant. results }
    K_kRatio             : array{1..15} of real;      { k ratio for a k line - unknown.  if std then this is std factor }
    L_kRatio             : array{1..15} of real;      { k ratio for a L line - unknown.  if std then this is std factor }
    M_kRatio             : array{1..15} of real;      { k ratio for a M line - unknown.  if std then this is std factor }
    Peak_to_Bkg          : array{1..15} of real;      { peak to background ratio - used for particles }
    ChiSqr               : array{1..15} of real;      { chi squared from fitting }
    Err_Energy           : array{1..15} of real;      { Ls - fitting error. Simplex - peak energy }
    Spare1               : array{1..15} of integer;
    Spare2               : array{1..15} of real;
    Unanal_Z_On          : boolean;
    Fixed_Conc           : array{1..15} of Boolean;
    Normalize_On         : boolean;
    bspare3              : boolean;
    bspare4              : boolean;
end;
```

A PREFERENCES FILE includes the information contained in the RECORD Setting.

```
Setting    - RECORD
              sText_Color                  : RGBColor;
              sPeakROI_Color               : RGBColor;
              sBkgROI_Color                : RGBColor;
              sScaleROI_Color              : RGBColor;
              sQuantROI_Color              : RGBColor;
              sAxes_Color                  : RGBColor;
              sBackGround_Color            : RGBColor;
              sPeakLabel_Color             : RGBColor;
              sKLMColor                    : RGBColor;
              SpectrumColor                : ARRAY {1..1c} of RGBColor;
              sGeom                        : Geometry;
              Peak                         : ARRAY {1..Max_ROIs} OF ROI_Data_Structure;
              BackGround                   : ARRAY {1..Max_ROIs} OF ROI_Data_Structure;
              Scale                        : ROI_Data_Structure;
              Quant                        : ROI_Data_Structure;
              Expt_Info                    : Expt_InfoRec;
              Plot_Info                    : Plot_InfoRec;
              SpectrumStuff                : Spectrum_Structure;
              counts                       : Spectrum_counts;
              Toler                        : real;
              DEN                          : real;
              DFWHM                        : real;
              Switch                       : real;
              Constraint_Switch            : Boolean;
              Incomplete_Charge_Switchs    : Boolean;
              WtSwitch                     : Boolean;
              Number_of_BackGrounds        : integer;
              Number_of_PeakRois           : integer;
              Element2                     : ARRAY {1..MaxNumPks} OF integer;
              SiLi_Response                : Spectrum_counts;
              Spectrum_Class_Holding_String : ARRAY {1..13} OF Str255;
              BoxLeft                      : integer;
              BoxTop                       : integer;
              XCenter                      : integer;
              YCenter                      : integer;
              High_Peak_Meas               : REAL;
              High_Peak_Book               : REAL;
              Low_Peak_Meas                : REAL;
              Low_Peak_Book                : REAL;
              NM_Alpha                     : REAL;
              NM_Beta                      : REAL;
```

FIG.27A

```
NM_Gamma                : REAL;
Amp_Perturb             : REAl;
Energy_Perturb          : REAL;
Width_Perturb           : REAL;
Energy_Estimate         : REAL;
Num_Noise_Spectra       : integer;
Thin_Fluor_Yield        : REAL;
Bulk_Fluor_Yield        : REAL;
Thin_K_Xsect            : integer;
Bulk_K_Xsect            : integer;
Thin_L_Xsect            : integer;
Bulk_L_Xsect            : integer;
Thin_M_Xsect            : integer;
Bulk_M_Xsect            : integer;
Bulk_CONT_Xsect         : integer;
Thin_CONT_Xsect         : integer;
Bulk_CONT_Xsect_BG      : integer;
Thin_CONT_Xsect_BG      : integer;
Thin_Wk_Choice          : integer;
Thin_Rslt_Choice        : integer;
Thin_S1_Choice          : integer;
Thin_S2_Choice          : integer;
Thin_S3_Choice          : integer;
Thin_S4_Choice          : integer;
Thin_S5_Choice          : integer;
Thin_S6_Choice          : integer;
Thin_S7_Choice          : integer;
Thin_S8_Choice          : integer;
Bulk_Wk_Choice          : integer;
Bulk_Rslt_Choice        : integer;
Bulk_S1_Choice          : integer;
Bulk_S2_Choice          : integer;
Bulk_S3_Choice          : integer;
Bulk_S4_Choice          : integer;
Bulk_S5_Choice          : integer;
Bulk_S6_Choice          : integer;
Bulk_S7_Choice          : integer;
Bulk_S8_Choice          : integer;
Bulk_K_ScaleFactor      : REAL;
Bulk_L_ScaleFactor      : REAL;
Bulk_M_ScaleFactor      : REAL;
Bulk_CONT_ScaleFactor   : REAL;
Thin_K_ScaleFactor      : REAL;
Thin_L_ScaleFactor      : REAL;
```

FIG.27A Cont.

| | | |
|---|---|---|
| Thin_M_ScaleFactor | : | REAL; |
| Thin_CONT_ScaleFactor | : | REAL; |
| Mu_Choice | : | integer; |
| Live_Time | : | REAL; |
| Thickness | : | REAL; |
| Faraday_Current | : | REAL; |
| Thin_At_Num | : | Array {1..15} of integer; |
| Thin_Concentration | : | Array {1..15} of real; |
| Thin_KV | : | REAL; |
| Thin_density | : | REAL; |
| tilt | : | REAL; |
| Bulk_At_Num | : | Array {1..15} of integer |
| Bulk_Concentration | : | Array {1..15} of real; |
| Bulk_KV | : | REAL; |
| Number_of_Elements_Simplexes | : | integer; |
| Elements_Chosen | : | Boolean; |
| Running_Bulk_Mode | : | Boolean; |
| Running_Thin_Mode | : | Boolean; |
| Thin_Physics_Boolean | : | Boolean; |
| Bulk_Physics_Boolean | : | Boolean; |
| WW | : | REAL; |
| XX | : | REAL; |
| YY | : | REAL; |
| ZZ | : | REAL; |
| Clmn1 | : | integer; |
| Clmn2 | : | integer; |
| Clmn3 | : | integer; |
| Sound_Off | : | Boolean; |
| Normal_Output | : | Boolean; |
| Reduced_Output | : | Boolean; |
| SiLi_Area | : | real; |
| MN_FWHM | : | real; |
| Det_Thickness | : | real; |
| Si_DeadZone | : | real; |
| Au_Contact | : | real; |
| Be_Window | : | real; |
| Pulse_Width | : | real; |
| Oxygen_Window | : | real; |
| Carbon_Window | : | real; |
| BN_Thickness | : | real; |
| SiN_Thickness | : | real; |
| Mylar | : | real; |
| Diamond | : | real; |
| Quantum | : | real; |
| Aluminum_Window | : | real; |
| END; | | |

FIG. 27B

| FILE | ANALYSIS | GENERATE | MATH | PARAMETERS | DISPLAY | SHOW HEADER | 4:06:04 PM |

| ATOMIC # OR SYMBOL | WEIGHT FRACTION | | |
|---|---|---|---|
| 1 K | 1.0000000 | ⊙ ELEMENT WEIGHT FRACTION | BEAM kV: 100.000 |
| 2 C | 0.0000000 | ○ ATOMIC FRACTION | NANOAMPS FARADAY: 1.000 |
| 3 Ca | 0.0000000 | ○ NUMBERS OF ATOMS | SECONDS, LIVE: 1000.00 |
| 4 Na | 0.0000000 | ○ mMOL/kg DRY WEIGHT | DENSITY, g/cc: 1.000 |
| 5 Mg | 0.0000000 | ○ DELETE WEIGHT FRACTION | THICKNESS Å: 100.000 |
| 6 Al | 0.0000000 | ○ ENTER VALENCES SEPARATELY | |
| 7 Si | 0.0000000 | INSERT ITEM IN DATABASE   REMOVE ITEM   LOAD NEW DATABASE |
| 8 P | 0.0000000 | ENTER HERE NAME OF NEW ITEM IN DATABASE (<50 CHARS) |
| 9 S | 0.0000000 | 1 KOKANUI HORNBLENDE |
| 10 Cl | 0.0000000 | 2 KAKANUI AUGITE |
| 11 0 | 0 | 3 QUARTZ |
| 12 0 | 0 | |
| 13 0 | 0 | SUM= 1.00000 |
| 14 0 | 0 | 1-SUM= 0.00000 |
| 15 0 | 0 | Av 2= 19.0000 |

PICK OUTPUT DESTINATION    * HELP *

| EXPERIMENT HEADER | SPECTRUM HEADER |
| DETECTOR PARAMETERS | PICK YOUR PHYSICS |
| LOAD DEFAULTS | CANCEL | ACCEPT |

FIG. 38

SINGLE CLICK ON A LIST ITEM TO GET MORE INFORMATION ABOUT THAT ITEM  IF YOU WANT TO DISPLAY THE ITEM THEN ENTER THE NUMBER AT THE LEFT OF THE ITEM IN ONE OF THE "SPECTRUM" BOXES ON THE LEFT SIDE OF THE DIALOG WINDOW.

ENTER A NUMBER FROM THE LIST ON THE RIGHT INTO A SPECTRUM BOX ON THE LEFT.

WORK: 100

RESULTS:

| | 100 FIN COMPOSITE SPECTRUM WITHOUT COUNTING NOISE |
|---|---|
| S1: 0 | 1 Qk— K SHELL IONIZATION CROSS SECTION VS Z |
| S2: 0 | 2 Ql— L SHELL IONIZATION CROSS SECTION VS Z |
| S3: 0 | 3 Qm— M SHELL IONIZATION CROSS SECTION VS Z |
| S4: 0 | 5 Qk*F*OMEGA VS Z |
| S5: 0 | 6 Ql*F*OMEGA VS Z |
| S6: 0 | 7 Qm*F*OMEGA VS Z |
| S7: 0 | 8 Qk*F*OMEGA/At.Wt. VS Z |
| S8: 0 | 9 Ql*F*OMEGA/At.Wt. VS Z |
| | 10 Qm*F*OMEGA/At.Wt. VS Z |
| | 11 Fk VS Z |
| | 12 Fl VS Z |
| | 13 Fm VS Z |
| | 14 OMEGA K VS Z |
| | 15 OMEGA L VS Z |

ACCEPT

FILE  ANALYSIS  GENERATE  MATH  PARAMETERS  DISPLAY  SHOW HEADER    4:06:48 PM

FIG.39

| FILE | ANALYSIS | GENERATE | MATH | PARAMETERS | DISPLAY | SHOW HEADER | 8:18:31 AM |

CHANGING ANY OF THE QUANTITIES ON THE LEFT WILL CAUSE A NEW DETECTOR RESPONSE CURVE TO BE GENERATED AUTOMATICLLY.
THIS CAN TAKE MANY SECONDS TO MINUTES
LEAVE A ZERO IN ANY QUANTITY THAT DOES NOT APPLY TO YOUR DETECTOR.

Au CONTACT [0.01] UM: RHO=19.3 (=0.01-0.02)
Si DEAD ZONE [0.20] UM: RHO=2.33 (=0.1-0.2)
• Be WINDOW [7.600] UM: RHO=1.82 (=7.6 OR 12.5)
CARBON [0.00] UM: RHO=1.0 (=0.01)
DIAMOND [0.000] UM: RHO=3.515 (=0.4)
BN [0.00] UM: RHO=2.25
KEUEN QUANTUM [0.000] UM: RHO=1.4 (=0.25)
Si3N4 [0.00] UM: RHO=3.44
MYLAR [0.0] UM: RHO=1.37 (=1 OR 6)

Al [0.000] UM: RHO=2.39 (=0.02)
ICE (AS OXYGEN) [0.90] UM: RHO=0.92 (=0.1-5)

DETECTOR THICKNESS [3.00] MM (=3)

RESOLUTION FWHM Mn [158.00] eV
DETECTOR AREA: [9.00] Sq. mm

[LOAD 'TYPICAL' VALUES]

[DETECTOR-SPECIMEN GEOMETRY DIALOG]

[*EDIT* THE *SPECTRUM* HEADER IN ACTIVE *FILE*]

[LOAD PARAMETERS FROM *WORK* SPECTRUM HEADER]

☐ PUT NEW RESPONSE CURVE IN 'RESULTS' AFTER A RECALCULATION

[ACCEPT]   [CANCEL]

FIG. 40

FILE  ANALYSIS  GENERATE  | MATH |  PARAMETERS  DISPLAY  SHOW HEADER    8:19:06 AM

CONVERT WAVELENGTH DISPERSIVE SCAN IN "WORK" TO AN ENERGY SCALE IN "RESULTS".

WAVELENGTH UNITS OF SPECTROMETER
- ⊙ ANGSTROMS
- ○ SIN THETA
- ○ MILLIMETERS

⊙ CONVERT H AND Y AXIS
○ CONVERT ONLY H AXIS

BEGIN CHANNEL # OF WDS: [ 1 ]    AND ITS VALUE: [ 1.00193 ]
END CHANNEL # OF WDS: [ 1000 ]   AND ITS VALUE: [ 2.00390 ]

eU/CHANNEL FOR ENERGY CONVERTED SPECTRUM: [ 10.0000 ]

2d (ANGSTROMS) SPACING OF CRYSTAL: [ 4.02670002 ]

| ⊙ LiF | ○ NaCl | ○ MoB4C | ○ Pb STEARATE |
| ○ PET | ○ MYA | ○ SiO2 1011 | ○ Mica |
| ○ TAP | ○ LOD | ○ SiO2 1010 | ○ EDDT |
| ○ RAP | ○ LDE1 | ○ Si | ○ USER1 |
| ○ KAP | ○ U-C | ○ GRAPHITE | ○ USER2 |

CANCEL   ACCEPT

FIG. 43

| FILE | ANALYSIS | GENERATE | MATH | PARAMETERS | DISPLAY | SHOW HEADER | .OPEN FIT FILE |

OUTPUT

K. OlinC_MLFitStd
AUGUST 5, 1991  9:20 AM

ANALYST: CRS
SPECIMEN_ID: HALL TEST
EXPERIMENT COMMENTS: BIO TEST SPEC FOR HALL
BEAM KeV = 100.00
TAKE OFF ANGLE = 40.000
ENTERED Mn FWHM (eV) = 158.000
Si(Li) DEAD ZONE (um) = 0.100
DETECTOR THICKNESS (mm) = 4.000
DETECTOR AREA (SQ. mm) = 30.000
DETECTOR-SPECIMEN DISTANCE (mm) = 45.000
CARBON WINDOW COMPONENT = 0.100
ICE (AS OXYGEN) = 1.000
Be THICKNESS = 7.600
Au THICKNESS = 0.020
ELEVATION ANGLE = 40.000
AZIMUTH ANGLE = 0.000

FROM REFERENCE FILE TEST REFS_USE: K K
QUANT BACKGROUND REGION = 1.350 : 1.450

1:  GENERATED K IN CARBON, NO NOISE
SPECTRUM WAS GENERATED; SPECTRUM CLASS: MATRIX
LIVE AND REAL TIME: 0.00000e+0    0.00000e+0
BEGIN AND END FARADAY CURRENT =  0.500     0.500
    FITTING REGION = 3.000 : 4.220
RESPONSE = 0.007    CALCULATED FWHM Mn = 158.0   INTERATIONS = 1
Z  LINE      AREA            FitSigma           P/B(10eV)      P/Chsn        CONC
19  K       2005.9154      61.75130081         204.571        131.170      0.010000

| FILE | ANALYSIS | GENERATE | MATH | PARAMETERS | DISPLAY | SHOW HEADER | OLD FIT FILE |

BEAM kV 100.00

| ATOMIC NUMBER OF SYMBOL | | WEIGHT FRACTION |
|---|---|---|
| 1 | 29 | 1.000 |
| 2 | 0 | 0.000 |
| 3 | 0 | 0.000 |
| 4 | 0 | 0.000 |
| 5 | 0 | 0.000 |
| 6 | 0 | 0.000 |
| 7 | 0 | 0.000 |
| 8 | 0 | 0.000 |
| 9 | 0 | 0.000 |
| 10 | 0 | 0.000 |

○ THIN TARGET
⦿ BULK TARGET

THIS FEATURE IS MAINLY TO BE USED TO BACKGROUND CORRECT REFERENCE SPECTRA ALTHOUGH IT CAN BE USED FOR OTHER PURPOSES.

\*\*\* YOU MUST HAVE PREVIOUSLY CHOSEN AT LEAST TWO BACKGROUND ROI's. \*\*\* SCALING WILL BE BASED ON THESE REGIONS.

THE SPECTRUM TO REMOVE THE BACKGROUND FROM SHOULD BE IN WORK. THE BACKGROUND CORRECTED SPRCTRUM WILL BE PUT INTO RESULTS.

ENTER WEIGHT FRACTION OF ALL COMPONENTS.
LEAVE 0 IN UNUSED CELLS.

[ OPTIONS ]   [ CANCEL ]   [ ACCEPT ]   [ DETECTOR PARAMETERS FOR FIT ]

FIG.51

DESK TOP SPECTRUM ANALYZER

BACKGROUND OF THE INVENTION

1. Field of the Invention

The present invention relates to an x-ray spectrum analysis system for spectra obtained with an electron microscope instrument. More particularly, the invention pertains to a computer based analyzer system which allows an analyst to extract quantitative information from experimentally acquired x-ray spectra and to simulate the experimental environment to generate theoretical spectra.

2. Description of Related Art

The physics and mathematics required to describe the generation and detection of a spectrum of characteristic and continuum x-rays resulting from the interaction of an electron beam with a specimen is described in an extensive body of literature. The generation of x-rays by interaction of an electron beam with a specimen is dependent upon the elemental composition of the specimen. Further complicating the process is the fact that detectors for the detection of x-rays have varying sensitivities, depending upon their construction. In use, the electron beam microscope is used to excite a spectrum representative of the sample. The final spectrum presented to the analyzer system depends on the specimen composition and geometry, the detector sensitivity, and the geometry of the electron microscope and detector configuration. The spectrum is then analyzed to determine the constituent elements of the sample and the relative proportions or absolute concentration of the elements in the sample.

The microprobe assay of a specimen must provide both a mean and the variance about this mean for each analyte or elemental constituent of a specimen. The mean refers to the estimate of the weight or atom concentration at a single analytical point, or some local grouping of points, from a homogeneous region of the specimen. The variance about this mean then represents the uncertainty due to counting statistics plus those aspects of the data reduction procedure which will contribute uncertainty, such as peak unraveling and continuum suppression. The accuracy of the estimate is a measure of the closeness of the estimate to the true value of the concentration. The task of predicting the variance about this estimated concentration can range from easy to quite difficult. As the specimen is further examined at many points, any variance greater than that determined above will represent true compositional variation. A significant period of time is required to collect enough data to analyze the specimen and estimate the concentration of the constituent elements to a sufficient accuracy and to a required level of confidence.

As with all measuring devices, the energy-dispersive x-ray analysis system has for a given set of conditions a sensitivity which translates into a minimum concentration of analyte that can be reported with a certain level of confidence. This quantity is often referred to as the minimum detectable limit (MDL) and its estimation can also range from easy to quite difficult.

A spectrum observed with an energy-dispersive spectrometer (EDS) consists of x-rays arising from both the characteristic and the continuum process. The x-ray peaks arising from the characteristic process contain the analytical information sought. Often the peaks to be determined overlap with the peaks from other elemental constituents of the specimen. Furthermore, the peaks are always superposed onto a smoothly varying spectrum of x-rays arising from the continuum process; and both the characteristic and continuum signals are modulated by the effects of counting statistics.

The MDL and variance about a measured concentration depend on the magnitude of the peak and background intensities, the degree of peak overlap, and the algorithms used to extract the required peak intensity and background intensity values below the peak. In general, there is no straightforward way of estimating the quantities required for standard statistical treatment. Therefore, many analysts, when faced with the problem of providing good error estimates, resort to the time-consuming but extremely reliable technique of direct measurement. In this method the specimen is sampled n times at a number of representative locations. For each of the n replicate measurements at each location one goes through all the spectra processing and data reduction steps required to arrive at an elemental concentration, where n is preferably greater than 25. From the n results at each location the analyst can then predict by conventional statistical methods the expected variance for each of the elemental concentrations at the various presumably representative locations. Knowing the expected variances the analyst can then proceed on with a strategy of single measurements at each analytical point in the specimen. For specimens with many phases or a wide range of compositions this procedure can be quite daunting. One approach to reducing the amount of time expended collecting the spectra data is to predict the minimum detectable limit achievable under proposed experimental conditions and to adjust these conditions to meet the requirements of the analysis.

There is an ever-growing body of knowledge concerning the physics of electron-specimen interaction and of the energy-dispersive x-ray spectrometer used to detect the resulting x-rays. The requisite knowledge is now at hand to generate from first principles an x-ray spectrum that is more than sufficiently close in all of the germane physical and statistical properties to represent an actual spectrum from a real specimen. From generated spectra one could then deduce accurate estimates of variance about mean compositional values and MDL of any analyzable stable element in any stable matrix. One might also accurately estimate the elemental composition of the specimen without the need to measure a set of calibration standards. Furthermore, one might adjust the experimental parameters to determine the optimum set that will produce the lowest MDL. One could do that relatively rapidly before even presenting a specimen to the electron beam.

By so determining the minimum detectable limits, the experiment could be designed so as to collect sufficient but not excessive spectrum data.

The electron microscope system is an expensive system to procure and operate. When analysis of the collected spectrum is performed using the computer analysis system that is part of the electron microscope system, the electron microscope system may not be used for the collection of x-ray spectra data. It would be beneficial to separate the analysis of spectra function from the collection of spectra function.

SUMMARY OF THE INVENTION

It is an object of the present invention to provide a system for the analysis of x-ray spectra that is independent of the electron microscope/x-ray acquisition system that collects x-ray spectra data.

This and other objects are achieved by a spectrum analyzer system comprising a spectrum analyzer, a data interface such as a serial data transfer line or disk for transferring spectra data from an electron microscope/x-ray acquisition system to the spectrum analyzer, and an output device, driven by the spectrum analyzer, for producing printed graphs and reports. The spectrum analyzer comprises a microcomputer having processing means for analyzing and transforming spectra data according to control modes defined by the analyst. Further, the spectrum analyzer preferably has an operator interface comprising a mouse and keyboard for receiving commands from an operator to define the control mode and a display for displaying the control mode and the processed spectra data. Further, the spectrum analyzer preferably comprises an input device for receiving the spectra data from an electron microscope/x-ray acquisition system and an output device driving a printer capable of printing graphics and text reports.

Yet another object of the invention is elemental analysis where a sample spectrum is plotted and displayed, peak areas determined and converted to concentrations using an appropriate quantitation scheme.

Yet another object of the invention is to provide the system by which an operator may adjust parameters pertaining to the generation of the theoretical spectrum and so that the differences between the displayed theoretical spectrum and the displayed sample spectrum are minimized and by which Poisson counting noise may be added to n generated spectra to simulate the experimental determination of variance and MDL.

BRIEF DESCRIPTION OF THE DRAWINGS

These and other objects will be described in the following detailed description of the preferred embodiments taken in conjunction with the accompanying drawings wherein:

FIG. 21 illustrates the data structure for the Experiment Header of an experiment file;

FIG. 22 illustrates the data structure for Spectrum Header of each spectrum of an experiment file, and for the spectrum image memories;

FIG. 23 illustrates the data structure for the multiple linear least squares regression set up files and references of the preferred embodiment;

FIG. 24 illustrates the data structure for the fit results file of the preferred embodiment FIG. 25 illustrates the data structure for the Hall file of the preferred embodiment;

FIG. 26 illustrates the data structure of the ZAF file of the preferred embodiment;

FIGS. 27A and 27B illustrate the data structure of the preferences file of the preferred embodiment;

FIG. 38 illustrates the first thin target spectrum dialogue interface of the generate submenu;

FIG. 39 illustrates the pick output destinations dialogue interface of the thin target spectrum dialogue interface of the generate submenu;

FIG. 40 illustrates the first detector parameters dialogue interface of the parameter submenu;

FIG. 43 illustrates the convert WDS scan to energy scale dialogue interface of the math submenu;

FIG. 46 illustrates a fit results display;

FIG. 47 illustrates the read sundry file formats dialogue interface for the file submenu;

FIG. 48 illustrates the experiment header dialogue interface of the parameters submenu;

FIG. 49 illustrates the spectrum header dialogue interface of the parameters submenu;

FIG. 51 illustrates a background subtract dialogue interface for the math submenu;

DETAILED DESCRIPTION OF THE PREFERRED EMBODIMENTS

Figure 1:
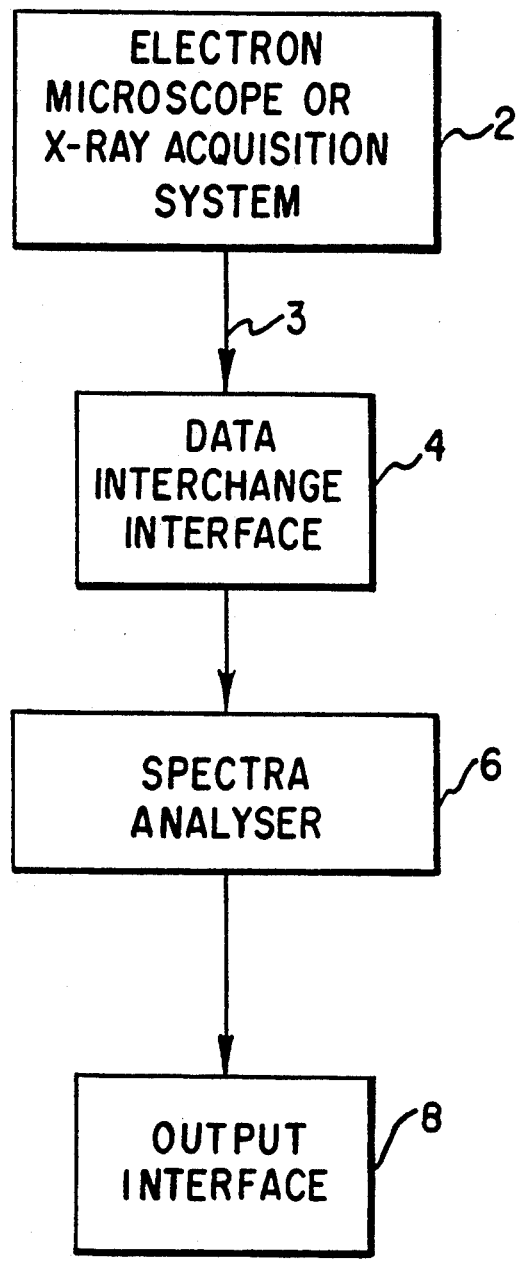
FIG. 1 illustrates the spectrum analyzer and its interfaces.

The known equations required to describe the generation and modification of the characteristic x-ray lines and background x-ray distribution in the specimen, the geometrical dependence of the detected radiation and the alteration of the spectrum by the detection process are incorporated in the spectrum analyzer. In one embodiment of the spectrum analyzer, spectra may be generated by the system or imported from an external source by the user and transformed to an internal format, and displayed in any one of ten spectra overlays of 8192 channels each. The values required for quantitative analysis of an experimentally collected spectrum may be extracted from the spectrum using multiple linear regression analysis or by the non-linear sequential simplex method. The analyst may choose among a number of widely accepted quantitation methods to obtain chemical concentrations expressed in the units appropriate to the particular method. The results of an analysis, of one spectrum or many spectra, may be saved as a binary file, an ASCII file, and one or more of the more popular readily available spreadsheet files for later statistical analysis. The system affords the analysts a full suite of mathematical tools to manipulate spectra such as scaling, summing, and filtering. Markers may be selected to indicate from one to all lines of an element, as well as the escape peaks, double energy peaks, and edges; labels may be displayed for each.

The analyst controls the progress of the analysis by selecting control modes from menus, dialogues and diagrams displaying values in editable text and options selected by, for example, mouse click or equivalent interface. Each value and option is operational until changed by the user, and, on exit from the program, all values and options are saved to become active on start-up. A set of all values may be saved at any time to a 'preference' file which the user can make the active set.

A computer environment which allows the user to interact with a computer system by means of windows, dialogues, pull-down menus and check boxes is available in commercial systems. The present invention described herein is one such system distinguished in that it enables the analyst to process and display spectra data from electron column instruments, and also provides the analyst the additional powerful capability to model the physical processes involved in the generation of an x-ray spectrum. The procedure to emulate the experimental environment and specimen to generate a series of spectra reflecting the relevant physics and statistics was previously described in terms of the application to estimating detection limits under proposed experimental conditions. This procedure clearly could reduce the amount of electron microscope time expended to acquire a particular set of useful data but, more fundamentally, it enables the analyst to develop an understanding of the physical and statistical parameters that affect the spectrum distribution and detection limits.

A major advantage of the system is that desktop analysis and processing of spectrum allows the analyzer on the electron beam instrument to remain free for data acquisition. Spectra acquired on a commercial multi-channel analyzer are converted to the system binary format by selecting from a menu of possible incoming formats and then stored in a menu specified file of related spectra. Spectra acquired with wavelength dispersive detector can also be converted to an energy distribution, scaled appropriately for direct comparison with Si(Li) detector spectra, and stored in the internal format. These spectra can be processed in a batch mode of operation using either the non-linear sequential simplex method of fitting generated Gaussians or the linear method for fitting reference spectra, with or without derivative references, to extract peak to background ratios. Required fitting information is provided by checking boxes and editing default text values or by accessing a file of previously chosen preferences. The results of the fitting procedure are automatically stored in an appendable binary file which can be accessed by the appropriate menu chosen quantitation procedure. They also can be reported in any of the common spreadsheet formats for convenient statistical analysis and plotting and as an ASCII text file.

Reference spectra required by the program for the analysis of a specified set of elements are automatically read from selections made by the analyst from a menu of previously created files. Each of these files contains any number of spectrum segments, either generated or acquired, all with experimental conditions such as kV and detector the same. The experimental parameters of the selected reference file are verified by the program to match those of the spectrum to be analyzed and the analyst is prompted to choose another file if a discrepancy is found. An appropriately generated background may be automatically subtracted from an acquired spectrum before storing the peak distribution in a reference file.

In generating a theoretical spectrum, functions such as the response of the silicon detector (lithium drifted silicon detector referred to as Si(Li)), mass absorption, the continuum distribution and characteristic peaks before and after convolution with the detector function are calculated and available for concurrent display in any of ten 8192 channel real valued 'spectrum displays'.

This affords the researcher a means to study the effect of the various physical phenomena at each step of spectrum production and on the final detected spectrum. One may vary detector characteristics such as the thickness of the gold contact layer, window, Si(Li) dead zone or ice, the resolution, or experimental parameters such as kV and specimen characteristics. By comparing detected distributions to generated the analyst can assess the physical condition of the detector-microscope environment or the suitability of experimental parameters for his analysis objective.

Any displayed distribution, be it an acquired spectrum, the results of fitting and stripping peaks from an acquired spectrum, a generated spectrum, or any distribution calculated to generate a spectrum, may be sent directly to a printer or stored in a file. Displayed distributions also may be summed, scaled, digitally filtered, Fourier transformed, smoothed, peak stripped and otherwise modified by a simple selection from a number of menus. An option to determine the operating voltage based on the method for determining the Duane-Hunt energy limit is also available.

A software interface to any spectrum acquisition system based on a NuBus card is provided. The user is able to set acquisition parameters such as acquisition time, eV per channel, discriminator setting, and the parameters of the particular pulse processor of the detector system and to control acquisition by means of dialogue interfaces. The spectrum data counts are accumulated and displayed in the Work spectrum image memory as they are acquired. Any processing function of the analyzer may be applied to the accumulated spectrum data while acquisition continues. The final spectrum accumulated in the Work spectrum image memory may be saved as a binary experiment file.

In FIG. 1, electron microscope/analyzer system 2 produces x-ray spectrum data 3 in a format defined by the analyzer system of the electron microscope. Spectrum data 3 is either stored in data interchange interface 4, which may be a floppy disk or other data interchange interface, or is stored on a hard disk and transferred to the spectrum analyzer via serial lines. The format of spectrum data 3 stored in data interchange interface 4 varies between different manufacturers of x-ray analyzers. Data interchange interface 4 is ported to spectrum analyzer 6 where the data interchange interface is received. An analyst working with the various controls of spectrum analyzer 6 produces output data which is transferred to output interface 8. Output interface 8 may be, for example, a laser printer capable of printing the analyzer 6 graphics display graphs and report text, or it may be a disk for electronic storage and later transfer of data.

Figure 2:
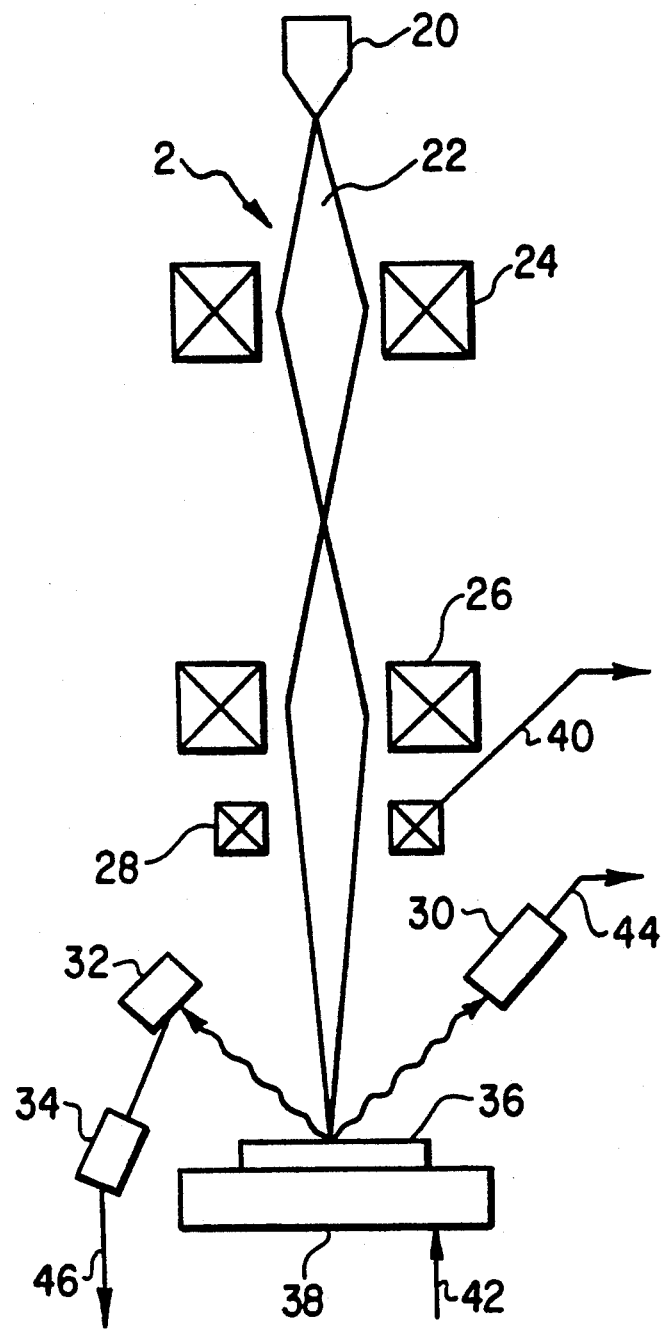
FIG. 2 illustrates a typical electron microscope.

FIG. 2 illustrates a typical electron beam microscope. Electron gun 20 produces electron beam 22 which passes through condenser lens 24 and through final-stage focusing lens 26 before impinging on specimen 36. Electron beam-scanning coil 28 is disposed proximally to the electron beam to make electron beam 22 scan the specimen surface in two dimensions. Electron beam-scanning coil 28 is driven by control signal 40. Specimen 36 is carried on specimen stage 38 which is moved according to control signal 42.

Disposed above the specimen are spectral crystal 32 and x-ray detector 34. Spectral crystal 32 and x-ray detector 34 together comprise a wave-dispersive x-ray spectrometer. X-rays emanating from specimen 36 arrive at spectral crystal 32 and are dispersed by the crystal structure. Only a certain wavelength of the x-rays is directed into x-ray detector 34 to produce detected signal 46. Spectral crystal 32 and x-ray detector 34 are moved such that a given relationship between them is maintained. Thus, different wavelengths of x-rays impinge upon detector 34 successively. As a result, the specimen is wavelength swept. Detector 34 forms output pulses which comprise signal 46. The output pulses are counted over a predetermined time and stored.

X-rays emanating from specimen 36 and arriving at detector 30 form an energy dispersive x-ray spectrometer. Detector 30 produces a pulse signal having a pulse amplitude corresponding to the energy of the incident x-ray. Output pulses of signal 46 is stored. A plurality of such pulse signals are counted to form an energy distribution spectrum.

Figure 3:
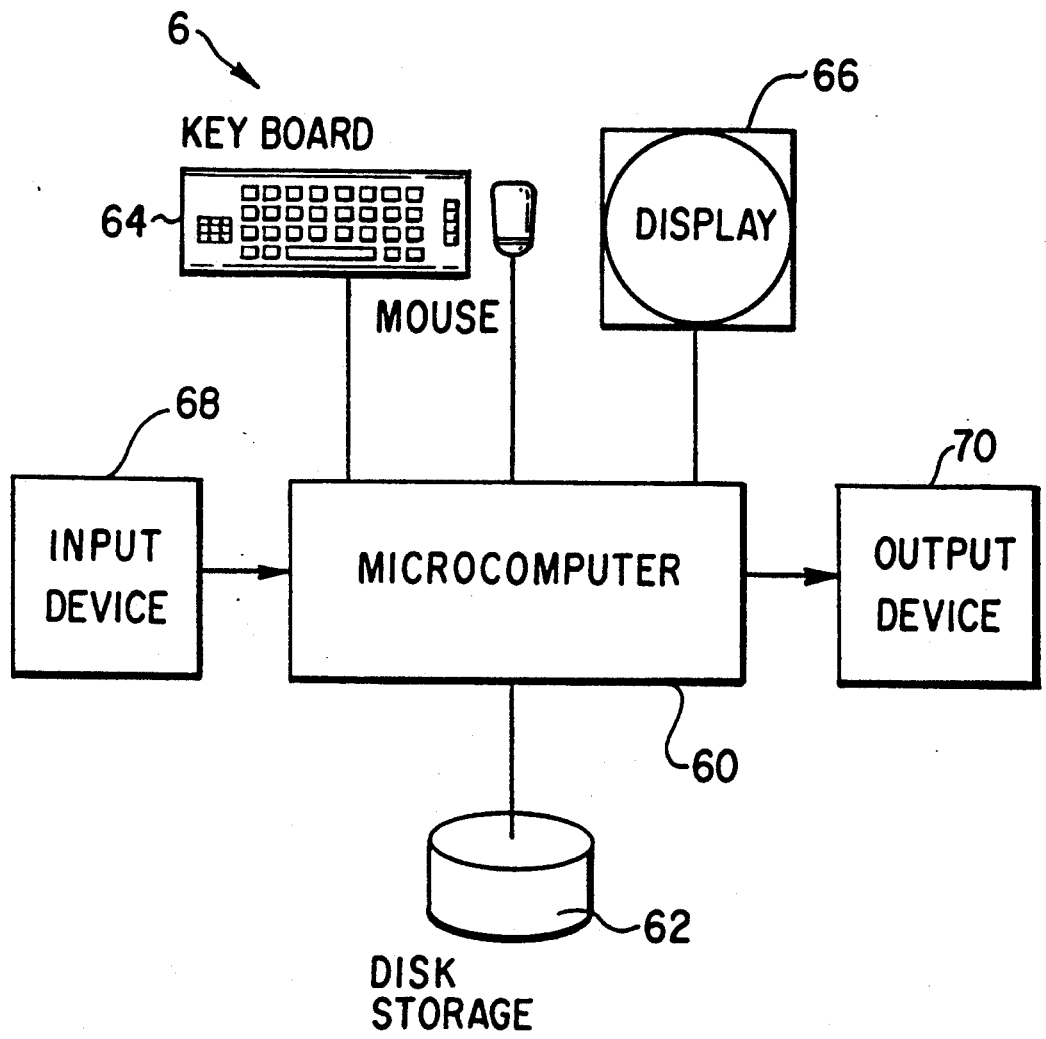
FIG. 3 illustrates one embodiment of the spectrum analyzer.

FIG. 3 illustrates an embodiment of spectrum analyzer 6. In this embodiment, an analyst interfaces with microcomputer 60 through keyboard/mouse 64 and display 66. Input device 68 receives data interchange interface 4, from FIG. 1. Thereafter, microcomputer 60 reads data from input device 68, processes the data and stores the data on disk storage 62. It will be appreciated that other storage media may be used in place of disk storage 62. After data is processed in microcomputer 60, it is transferred to output device 70. Output device 70 drives output interface 8, of FIG. 1. Spectrum analyzer 6 is based upon a microcomputer design so that it may be conveniently located on an analyst's desktop. Microcomputer 60, under user commands from keyboard/mouse 64, performs a variety of processing tasks.

Figure 4:
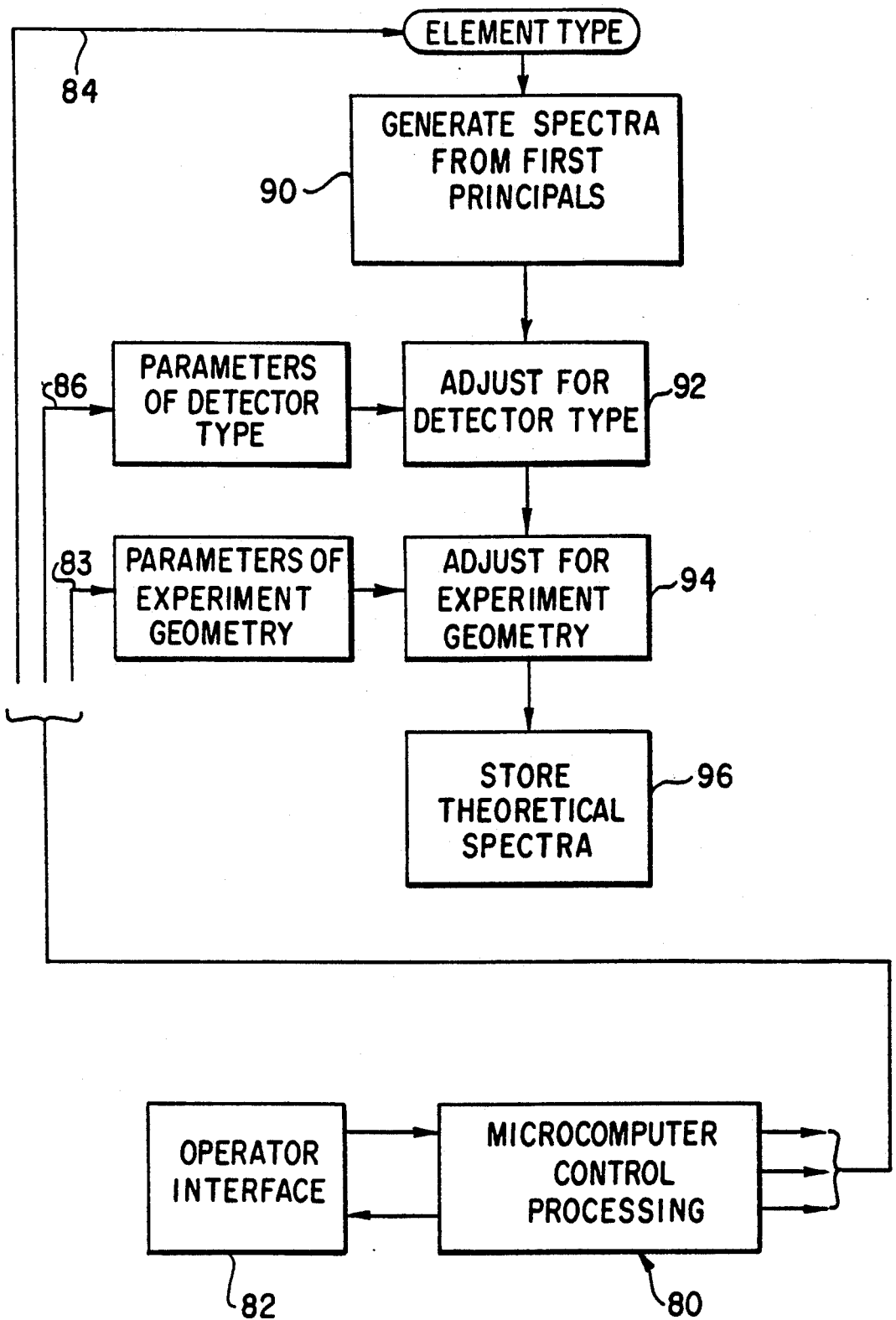
FIG. 4 illustrates an embodiment of the process for generation of a theoretical spectrum.

FIG. 4 illustrates one such processing task. Operator interface 82 comprises both keyboard/mouse 64 and display 66 as well as required interface control processing. Operator interface 82 controls microcomputer processing 80 so as to generate commands 84, 86 and 88. Command 84 identifies the element type whose spectrum is to be generated from first principles in processing step 90. The spectrum so generated is adjusted in step 92 based on the detector type that is to be simulated according to the detector type parameters provided in command 86. The spectrum so generated in step 90 and adjusted in step 92 is further adjusted in step 94 based on the experiment geometry provided by experiment geometry commands 88. The spectrum so generated in step 90 and adjusted in step 92 and further adjusted in step 94 is stored in step 96 in a storage device such as disk storage 62, of FIG. 3.

Figure 5A:
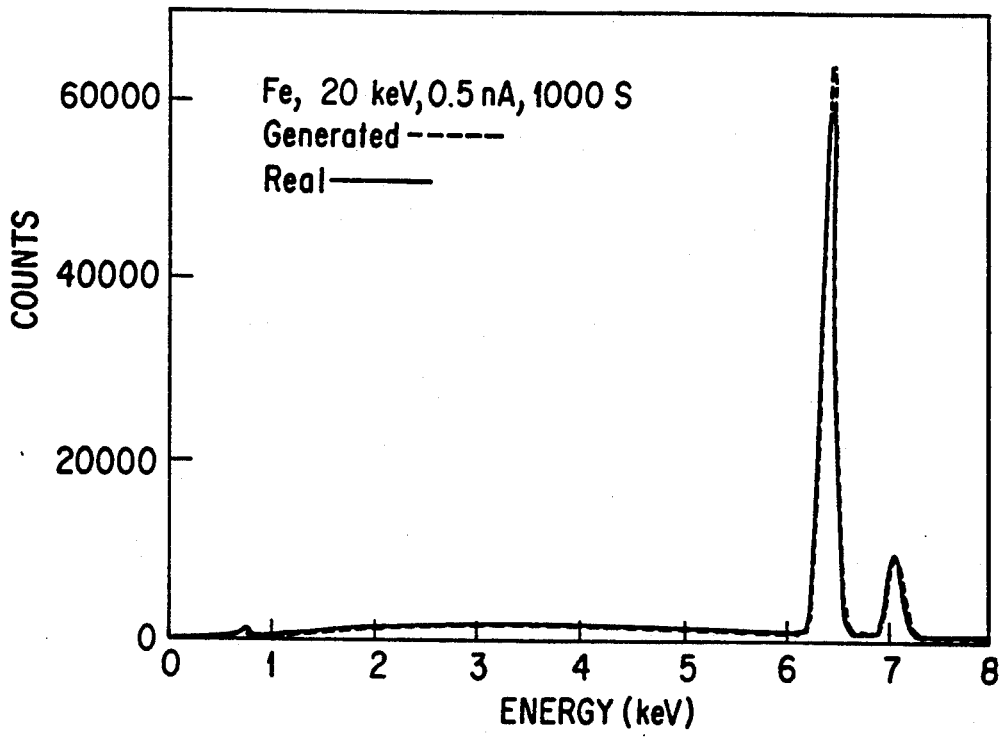
FIG. 5A is a graph showing the spectral response of a real iron sample overlayed on a generated theoretical iron spectrum.

FIG. 5A is a graph of an energy spectrum of iron, Fe, collected over 1000 seconds with an electron beam current of 0.5 nA and an acceleration potential of 20 keV. The figure shows real data overlayed upon theoretical data generated as described in connection with FIG. 4. The real data is a plotted spectrum from bulk iron acquired in a Cameca electron probe with a 9 $mm^2$ acquisition detector which was located 52 mm from the specimen. The theoretical spectrum was generated from first principals using the same experimental parameters, and no arbitrary scaling was used for either continuum or characteristic distributions. As can be seen from FIG. 5A, there is substantially no difference between the real spectrum and the theoretically generated spectrum.

The well-known K-Ca overlap problem typical in biological x-ray microanalysis provides a good example of a case in which conventional statistical procedures cannot provide accurate estimates of the variances about the mean energies because one cannot extract independent estimates of the peak and background under the peak. When the peak-to-background ratio is small, as it is for the Ca peaks in our chosen example, the uncertainty in peak estimation is strongly influenced by the continuum statistics and the effect of the overlapping K K$\beta$ peak. The technique of spectrum generation described in this disclosure permits a rapid simulation of n spectra each of which has the statistical properties of actual spectra acquired for typical experimental times. Each spectrum can be analyzed by any of the procedures normally used to extract peak areas. The variance about the mean can then be calculated directly.

Figure 5B:
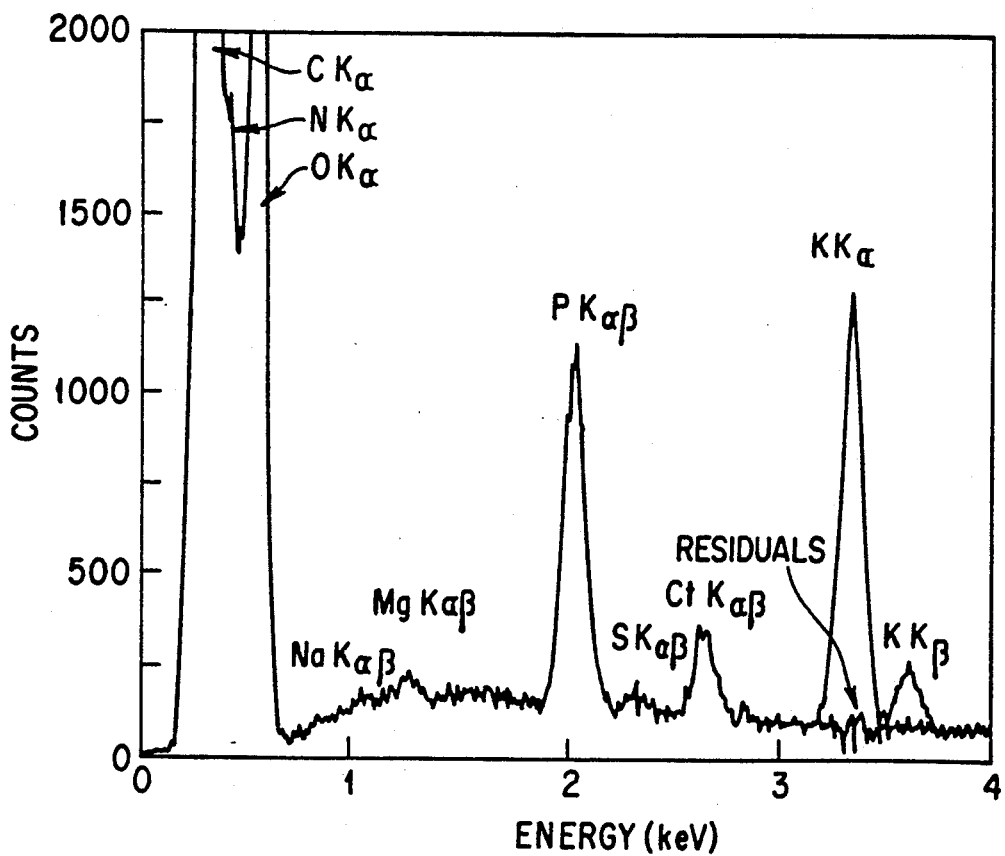
FIG. 5B is a graph of a typical spectral response for a sample having a plurality of constituent elements.

As an experiment to demonstrate this procedure, 25 spectra were generated, identical except for the counting statistics, representing a typical biological matrix which contains 0.02 weight fraction K and 0.00022 weight fraction Ca. FIG. 5B illustrates such a spectrum. The spectrum was generated with parameters corresponding to a Vacuum Generator HB 501 dedicated STEM operating with a 100 kV, 0.5 nA electron beam for 1000 seconds of acquisition time, and a UTW Si(Li) detector with a 0.18 steradian solid angle used as the x-ray detector.

The spectra were analyzed using a sequential simplex algorithm to produce the mean value and standard deviation for K of 10462±143 and of Ca of 80±71. Clearly, to extract this weight fraction of Ca with 97% certainty will require a considerably longer acquisition time per spectrum and/or more spectra.

It will be apparent that an analyst using the spectrum analyzer may generate a sufficient plurality of spectra so as to determine the experimental parameters required so that the mean value and standard deviation obtained will be sufficiently controlled so that the experiment conclusion may be supported to the desired level of confidence. Without this process, it would be necessary to collect and analyze real spectra in order to design the experiment necessary to achieve a desired variance or MDL.

Figure 6:
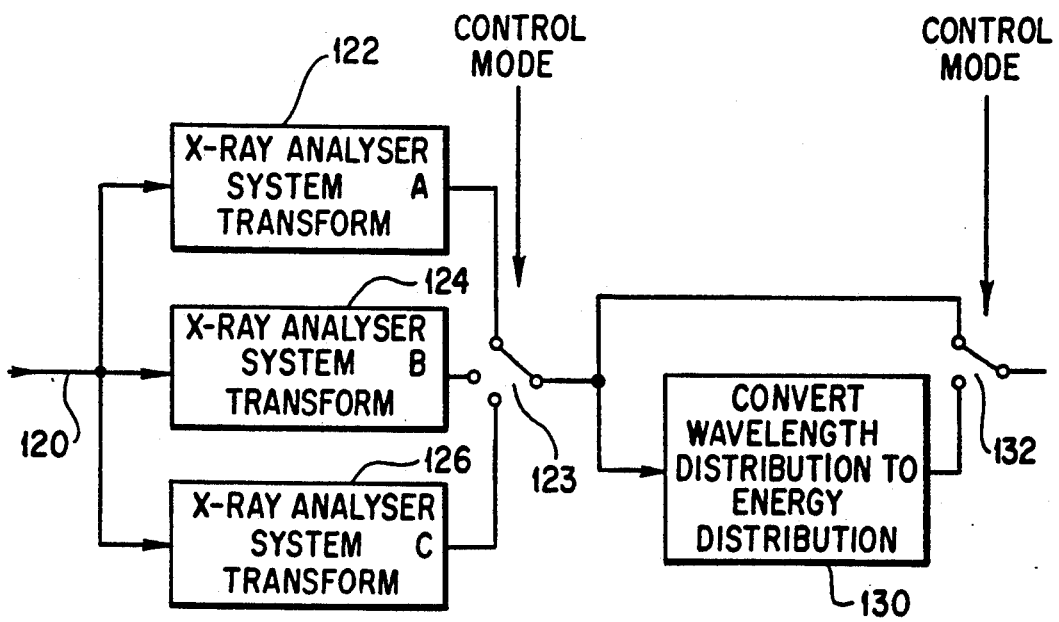
FIG. 6 illustrates processing for an interface transform.

In FIG. 6, acquired spectrum 120 is received from input device 68 of FIG. 3. Acquired spectrum 120 is fed through one of transform 122, transform 124 and transform 126 according to mode control 128. Transforms 122, 124 and 126 serve to transform the data format provided by commercial data acquisition system 2 of FIG. 1 into a standard format for spectra used in spectrum analyzer 6 of FIG. 3. When acquired spectrum 120 is of a wavelength dispersive spectrometer form, converter 130 converts spectra data to an energy distribution spectrum form according to control mode 132. The resulting spectrum is stored in a storage such as disk storage 62 of FIG. 3.

Figure 7:
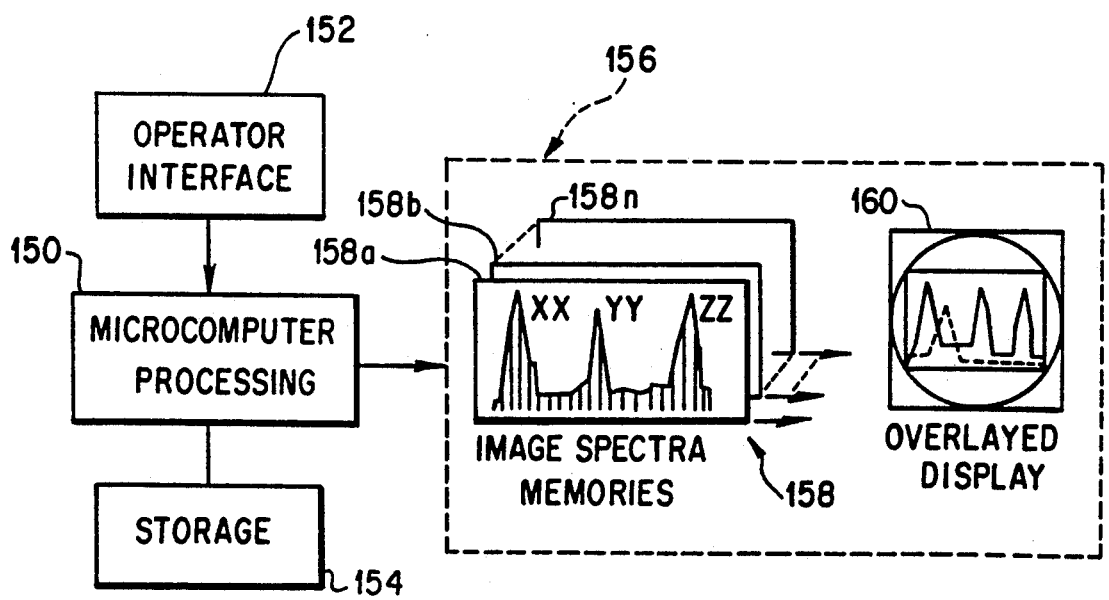
FIG. 7 illustrates a display interface for the spectrum analyzer.

FIG. 7 illustrates details of display 66 from FIG. 3. The display comprises display screen 160 and spectra memories 158. Spectra memories 158 in turn comprise a plurality of memories 158a, 158b, . . . 158n, which plurality is preferably ten. Each display memory is capable of storing a single spectrum comprising, for example, 8192 channels. The plurality of spectra memories 158 are overlayed on each other and displayed on display 160 in such way as to indicate to an observer distinct spectra distributions. Such indication may be by means of multicolored displays where each spectrum memory image is assigned to a unique color. Individual spectrum memories are loaded with data from microcomputer processing 150 or cleared of data according to commands from microcomputer processing 150. Microcomputer processing 150 is the display processing portion of the processing carried out in microcomputer 60 of FIG. 3. Operator interface 152 is comprised of keyboard/mouse 64 of FIG. 3 or equivalent. Storage 154 is the display storage allocation of disk storage 62 of FIG. 3, or equivalent. In operation, an analyst, operating spectrum analyzer 6, processes spectra as required and saves to storage 154 such spectra as the analyst desired displayed. Under control of microcomputer processing 150 desired spectra for display are transferred from storage 154 to spectra memories 158, and consequently displayed on display 160.

Figure 8:
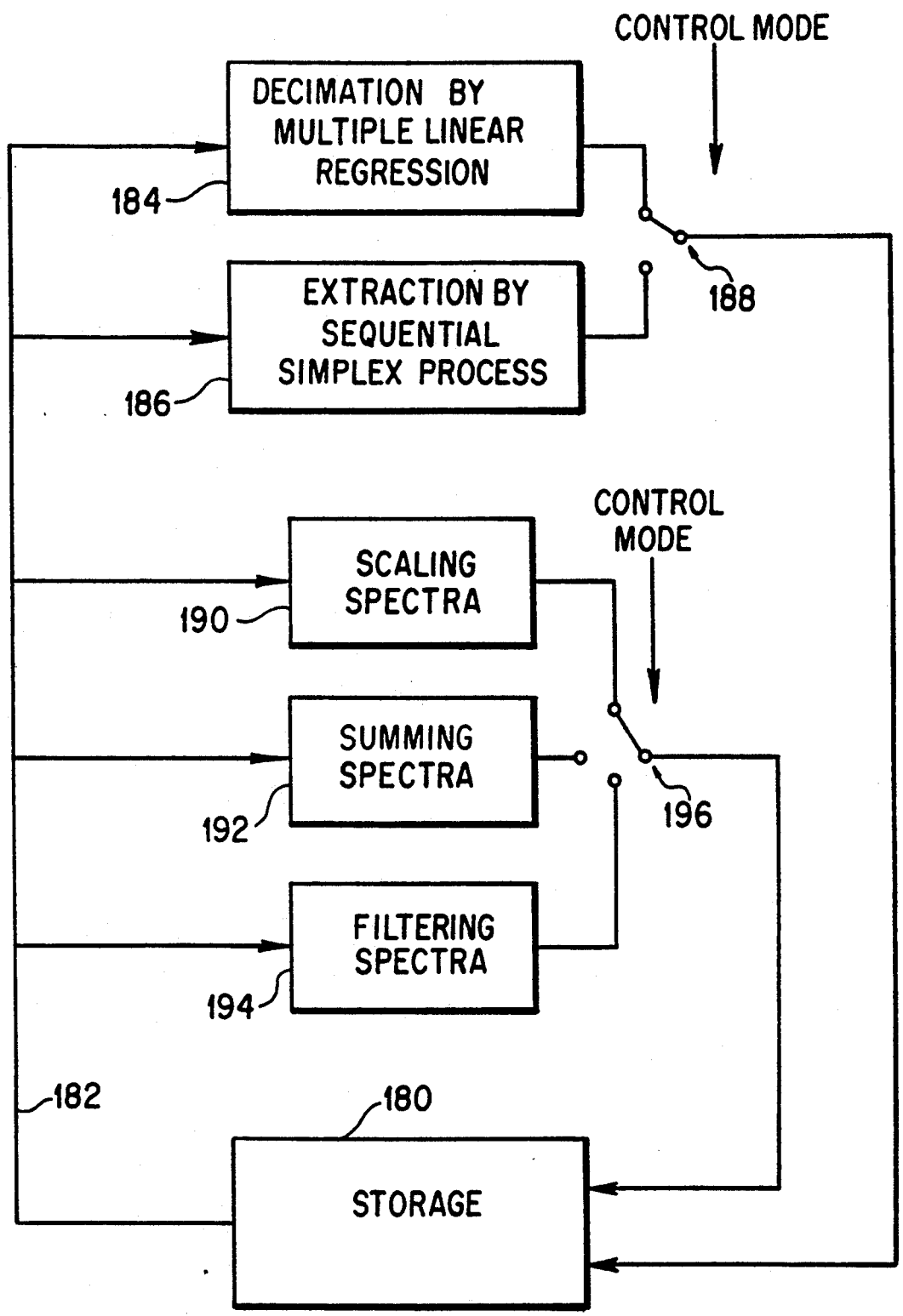
FIG. 8 illustrates processing filters and transforms for the spectrum analyzer.

FIG. 8 shows spectra processing commanded by an analyst. In general, an analyst issues commands through keyboard/mouse 64 to microcomputer 60, as shown in FIG. 3, to generate theoretical spectra data as shown in FIG. 4, or to import acquired spectra data as shown in FIG. 6. Spectra data so acquired or generated is further processed as shown in FIG. 8. Spectra data so acquired or generated is stored in storage 180 which is a portion of disk storage 62 of FIG. 3. Under a command from an analyst, spectra 182 is retrieved from storage 180 and fed to one of processes 184, 186, 190, 192 and 194. The output of the process is stored in storage 180 according to analyst commanded control mode to switch 188 and 196. In process 190, spectra 182 is scaled by multiplying each channel in the spectrum by a scaling constant, which may be positive or negative. Process 192 additively sums two spectra provided though spectra 182. Process 194 filters spectra 182 according to a variety of criteria including differentiation, integration, etc. The results of processes 190, 192 and 194 are spectra which are returned to and stored in storage 180. Process 184 returns peak areas and background value from an acquired spectrum utilizing a plurality of generated or acquired background-free spectrum segments by multiple linear regression. A properly scaled background-free spectrum segment of a constituent element is deducted from an acquired spectrum leaving a residual spectrum. Thereafter, another properly scaled spectrum segment of another constituent element is deducted, the process being repeated until all significant elements have been deducted and the residual spectrum shows no contributions from the peaks of interest. Process 184 stores the constituent elements, scaling factors, and other parameters pertaining to the process in storage 180 when switch 188 is commanded by the analyst exercising control through the proper control mode. In an analogous way, process 186 extracts critical parameters by a sequential simplex process and stores the critical parameters in storage 180 when switch 188 is so commanded by the control mode. The parameters so extracted may be used to calculate elemental concentrations using one of the standard quantitation routines provided.

Figure 9:
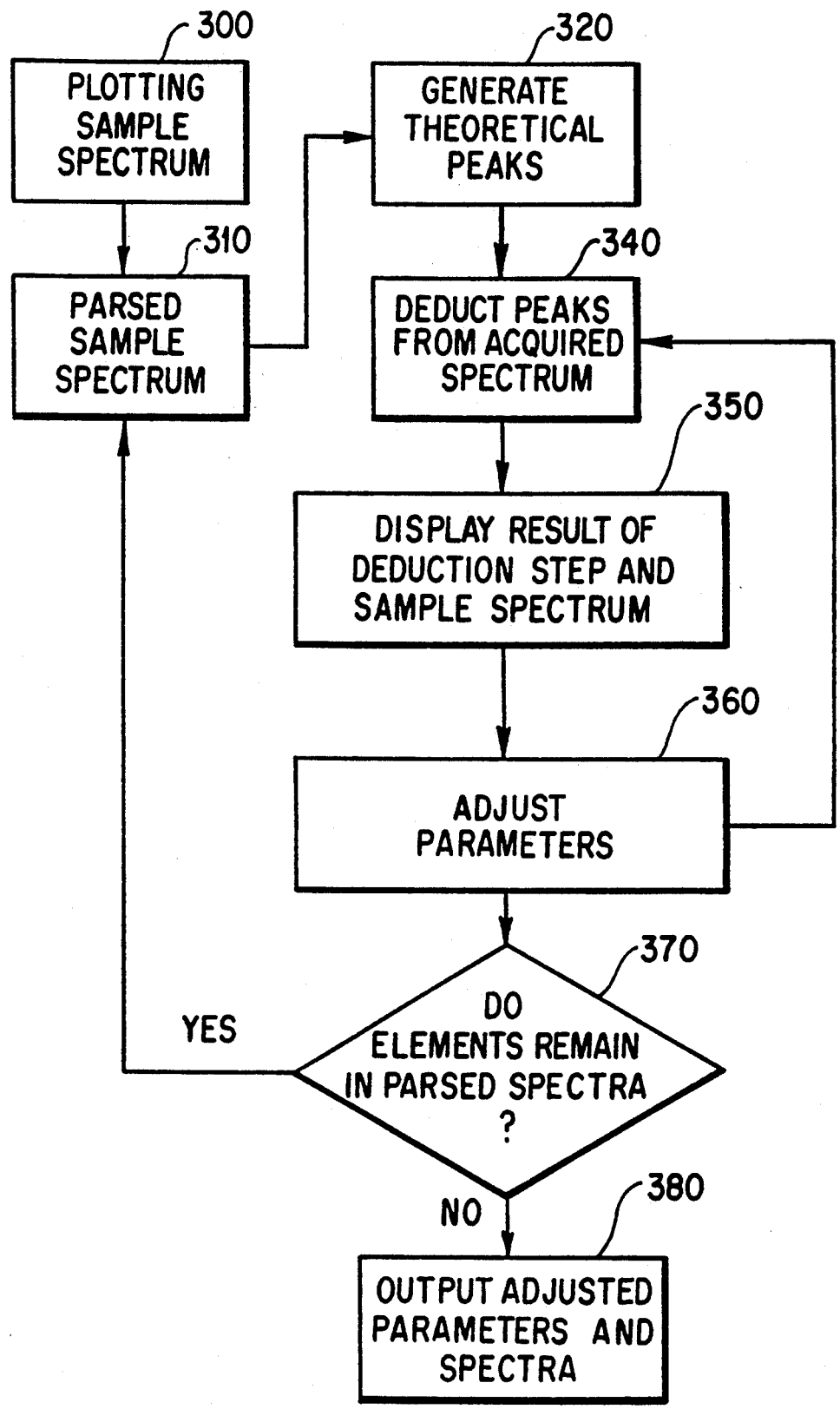
FIG. 9 illustrates a method of elemental analysis.

FIG. 9 shows a method for quantitative identification of the elemental constituents of a sample according to the present invention. In process step 300, a spectrum produced by electron microscope 2 and stored on data interchange interface 4 of FIG. 1 and received in input device 68 of FIG. 3 and transferred to disk storage 62 of FIG. 3 under control of microcomputer 60 of FIG. 3 is written in one of the spectra memories 158 of FIG. 7. An analyst observing display 160 identifies a constituent element in the plotted acquired spectrum. In step 320, the analyst generates a theoretical peak distribution for the identified element according to the process shown in FIG. 4 and deducts it from the acquired spectrum in step 340. The resulting spectrum is plotted in one of the spectra memories 158. In step 350, the analyst observes the differences between the acquired spectrum and the theoretical generated spectrum. In step 360, the analyst adjusts the parameters used for generating the theoretical spectrum so that differences between the theoretical spectrum generated according to the adjusted parameters and the acquired spectrum are minimized over a selected portion of the acquired spectrum.

In step 340, the analyst deducts the theoretical spectrum generated according to the adjusted parameters from the acquired spectrum and displays the residual spectrum. In step 370, the analyst decides if the residual spectrum indicates that further constituent elements remain to be parsed. If the answer to this decision is yes, in step 310, the residual spectrum is labeled parced spectrum and plotted in one of the spectra memories 158. Again, in step 340, the analyst identifies a constituent element appearing in the parsed spectrum. The analyst then repeats the generation and plotting of the theoretical spectrum for the identified element in step 320 and 340 and repeats steps 350, 360 and 370 until no more elements are identified in the parced spectrum, at which time all constituent elements of the sample have been identified including parameters pertaining to the samples such as the peak areas which can be converted to percentage composition by the appropriate quantitation scheme. In step 380, these parameters are output through output device 70 to output interface 8 in the form of reports, graphs or interfaces with other computing machinery.

A spectrum as used herein refers to an x-ray energy distribution comprised of a plurality of channels, each channel containing a count. A channel is defined by a channel width beginning at a lower energy end of the channel and spanning to an upper energy end of the channel. The plurality of channels are disposed adjacent to one another to form a continuous region of interest spanning from the lowest energy of interest to the highest energy of interest. For example, a channel may have a width of 10 eV. The plurality of channels may, for example, comprise 8192 channels which, when concatenated together, span a region of interest that is 81.92 KeV wide. Each channel is characterized by a count representing the number of x-ray photons that were detected by the x-ray detector between the lower energy boundary and upper energy boundary for that channel. It will be appreciated that counts collected during a short experimental time will be smaller than counts collected during a longer experimental time. Random factors, which constitute noise, associated with real spectra cause a randomness in the distribution of the counts in the plurality of channels. It will be apparent that longer experimental times, which collect larger counts, will reduce variances between one experiment and the next. It will be appreciated that each spectrum so produced is a histogram of the x-ray photons that were detected during the experiment.

A spectrum so defined is stored in a computer as a linear array. Each element of the array corresponds to a respective channel, the channel being characterized by a channel width and a center channel energy or position. In order to compare one spectrum to another, it is necessary for each of the two spectra to be characterized by the same channel definitions.

Spectra may be stored as real or integer data and are usually accompanied by a header which contains a body of information about the detector, the electron microscope/x-ray acquisition system, specimen conditions and orientations and other experiment conditions. Spectra and headers that come to the analyzer from other system may be in ASCII, binary, or mixed format, or may be in a predetermined "order" which depends on the specific system which is the source of the data. The invention herein reads the spectra data from a plurality of diverse spectra acquisition systems, processes the spectra data, and rewrites the spectra data in the internal format standard of the Desk Top Spectrum Analyzer. A dialogue interface is provided to allow the user the add information that may not be stored in the files of other spectra acquisition systems.

A typical spectrum contains one or more peaks generally representative of one or more atomic elements plus background spectral energy. A peak may be characterized by specific parameters. For example, a peak may be characterized by its amplitude, width and position (energy of the peak).

It is a task of the present invention to determine the amplitude, width and position of a spectral peak in a sample spectrum. This task is made complicated due to the background energy contained in the sample spectrum and due to the spectral response from a plurality of different atomic elements in the sample specimen. Although it is desirable to determine the amplitude, width and position of a peak associated with calcium, for example, it is difficult to determine what portion of the count in a given channel is attributable to the calcium and what portion of the count in the same given channel is attributable to a conflicting element such as potassium, for example. In complex biological and material science specimens there may appear a complicated matrix of elemental constituents of the sample, each of which contribute to the count in regions of spectral interest for the other elemental constituents. It is a complex procedure to first determine the quantity of a first elemental constituent of the matrix and then remove from the sample spectrum the contribution in the sample spectrum that resulted from the first elemental constituent of the specimen. If successfully done, the residual spectrum will reflect an x-ray spectrum that would be produced if the first elemental constituent were not present in the specimen. As this process in continued, the contribution to the sample spectrum caused by additional elemental constituents may be deducted from the sample spectrum so as to parce the spectrum into its elemental constituents.

There are several well known techniques for determining the peak areas of constituent elements. For example, multiple linear least squares fitting techniques are well known and may be applied to a sample spectrum to determine best fits against the known spectrum of the elemental constituents of the specimen under consideration. Another well known technique in the analytical chemical arts is simplex peak fitting. Both of these techniques are implemented in the invention.

Once the peak area of an elemental constituent of the sample spectrum has been quantitatively determined, it is a task of the present invention to provide quantitative estimates of the concentrations of the elements in the specimen. Several well known procedures are provided by the invention for this task. In the material sciences, a well known technique is ZAF analysis to convert x-ray intensity peak areas into chemical values representative of the elemental weight fractions of the elemental constituents of the specimen. A well known procedure for biological quantitation is the Hall method. Yet another well known procedure to the material sciences is standardless ZAF analysis.

Figure 10:
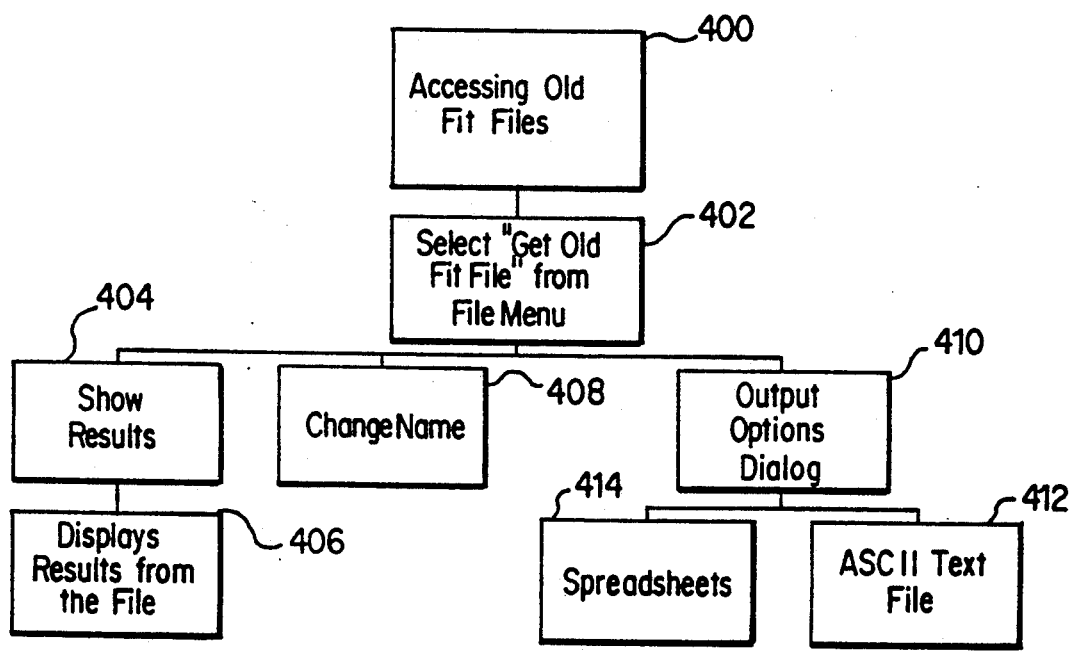
FIG. 10 illustrates manipulation of fit results files.

FIGS. 10–21 describe by way of example a preferred embodiment of the invention. FIG. 10 illustrates the steps for accessing old fit files. A fit file is a binary file of results from Multiple Linear Regression or Simplex processing of spectra. A selection such as "get old fit file" from a file menu as illustrated in step 402 sets the control mode of the analyzer so that the user will be queried as to either show results, change name or output. If the user selects show results, the results in the fit file currently selected will be displayed in an ASCII format. If the user selects change name, the user will be given an opportunity to enter a new name for the fit file. If the user selects output, the user will be given the option to output the fit file in a variety of spreadsheet formats or an ASCII text file format.

Figure 11:
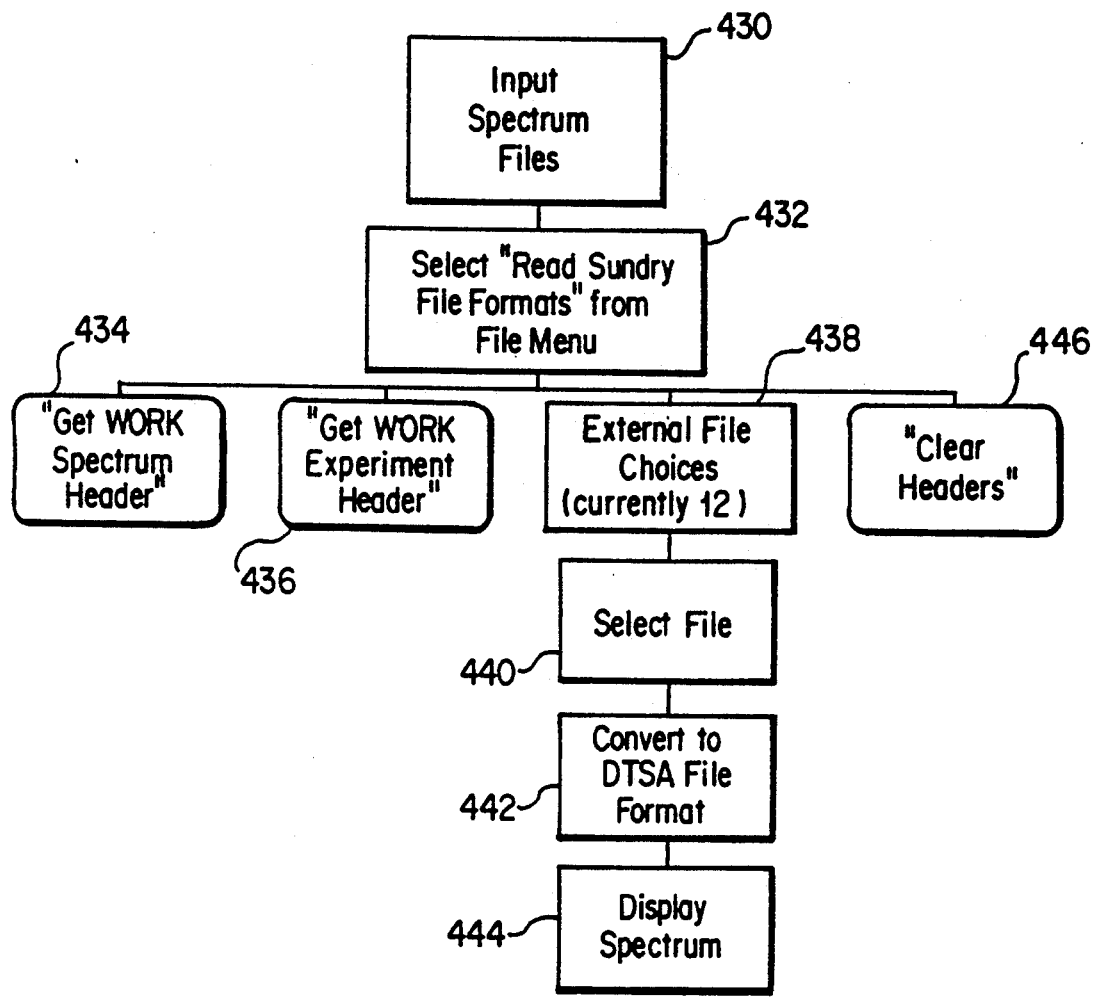
FIG. 11 illustrates the process of converting external files to internal binary form.

FIG. 11 illustrates steps for receiving external spectra files. When the user selects "read sundry file formats" from the file menu the analyzer sets control modes to receive the input spectrum files. The user enters a spectrum header into a "work" storage area and enters an experiment header into the "work" storage area. Thereafter, the user selects from among a plurality of external file choices to import a selected sample spectrum file and convert to a desktop spectrum analyzer file format for display and processing.

Figure 12:
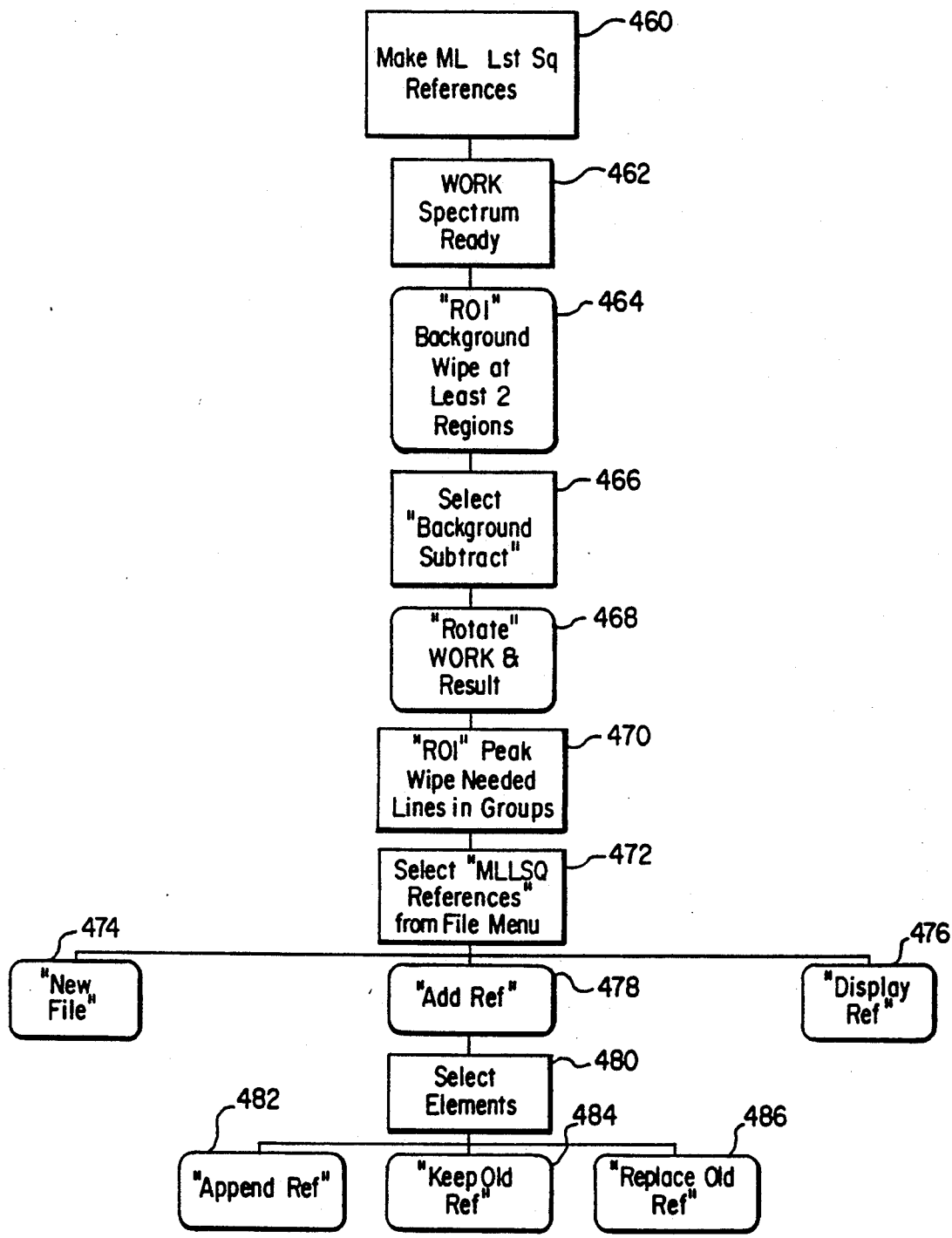
FIG. 12 illustrates the process of making a reference for multiple linear least squares fitting of spectrum peaks.

FIG. 12 illustrates the steps for making a multiple linear least squares reference. At step 462 the work spectrum is prepared as described in FIG. 11 or retrieved from an analyzer storage area. At step 464 a region of interest is identified by moving a cursor across a segment of the displayed work spectrum. At least two regions are selected to fit the background. At step 466 the background is deducted from the spectrum. At step 470 the user specifies a region of interest for each characteristic peak bundle which has no overlay from an adjacent bundle. The user may specify the region of interest using, for example, a mouse and mouse directed cursor in conjunction with the display of the spectrum. At step 472 the user selects multiple linear least squares references from the file menu. The user may then specify either a new reference file at step 474, display a reference file at step 476, or to add a reference to an old file at step 478. If a reference is to be saved as selected at step 474 or 478, the user then selects the elements in step 480 to define the region of interest (ROI) peak bundles to be saved as references. Thereafter the reference may be appended to the file at step 482, or the user may select either to keep an old reference at step 484 or replace an old reference at step 486.

Figure 13:
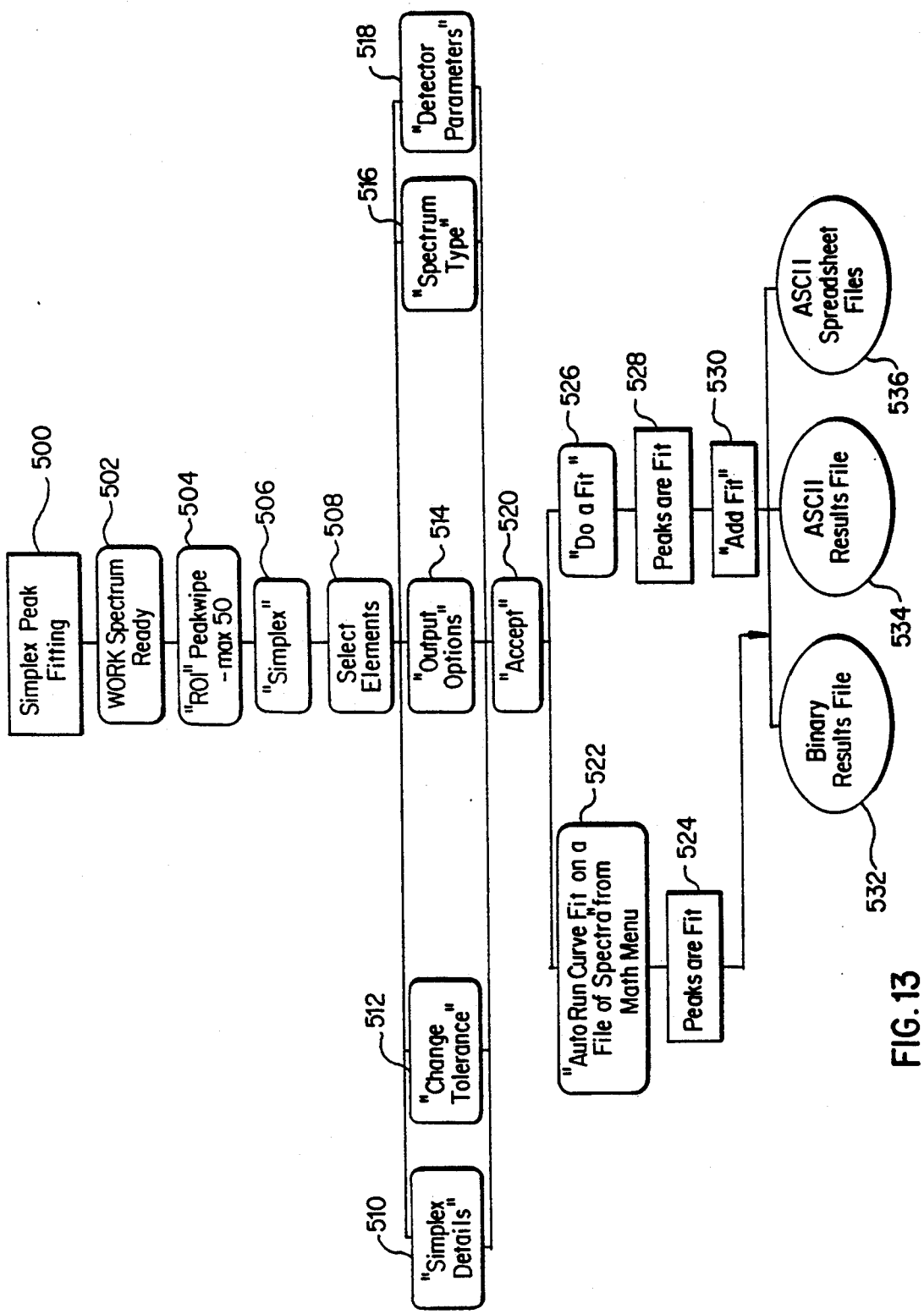
FIG. 13 illustrates the process of fitting spectrum peaks by the sequential simplex method.

In FIG. 13 the simplex peak fitting procedure is illustrated. At step 502 the work spectrum is prepared and at step 504 at least one region of interest is identified. At step 506 the simplex analysis procedure is selected. At step 508 the user selects the elements to be fit by the procedure. At step 510 parameters of the algorithm are displayed to the user for possible modification. At step 512 the user is given the opportunity to change the exit tolerance used in the simplex analysis. At step 516 the user identifies the spectrum type, EDS (energy dispersive spectra) or WDS (wavelength dispersive spectra). And at step 518 the user identifies the detector parameters. At step 514 the user is given output options for the results of the analysis. At step 520 the user may accept the simplex analysis. At step 522 the user selects an auto curve fit on a file of spectra: peak fitting is done in step 524, and output files are produced in steps 532, 534 and/or 536. Alternatively to step 522, at step 526 the user selects to fit the "work" spectrum: the peaks are fit in step 528, and the user may select in step 530 to add the fit results to the output files as in step 532, 534 and/or 536.

Figure 14:
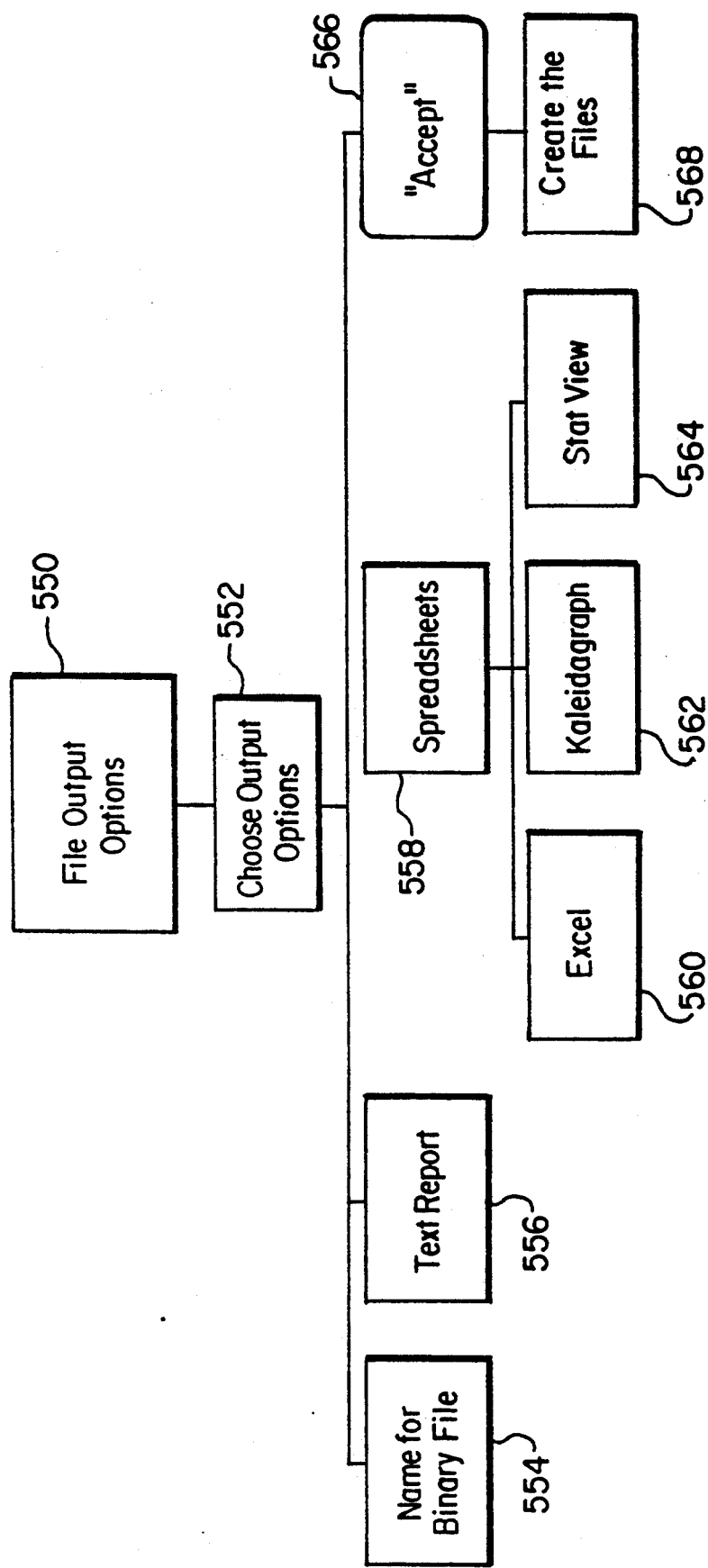
FIG. 14 illustrates the process of making various output formats of a fit results file

FIG. 14 illustrates file output options. At step 552 the user is prompted to choose output options comprising the option at step 554 to name a binary file, the option at step 556 to produce a text report, the option at step 566 to accept the output and create a file of the results, and the option at step 558 to produce outputs for spreadsheets sheets including Excel at step 560, Kaleidagraph at step 562 and StatView at step 564.

Figure 15:
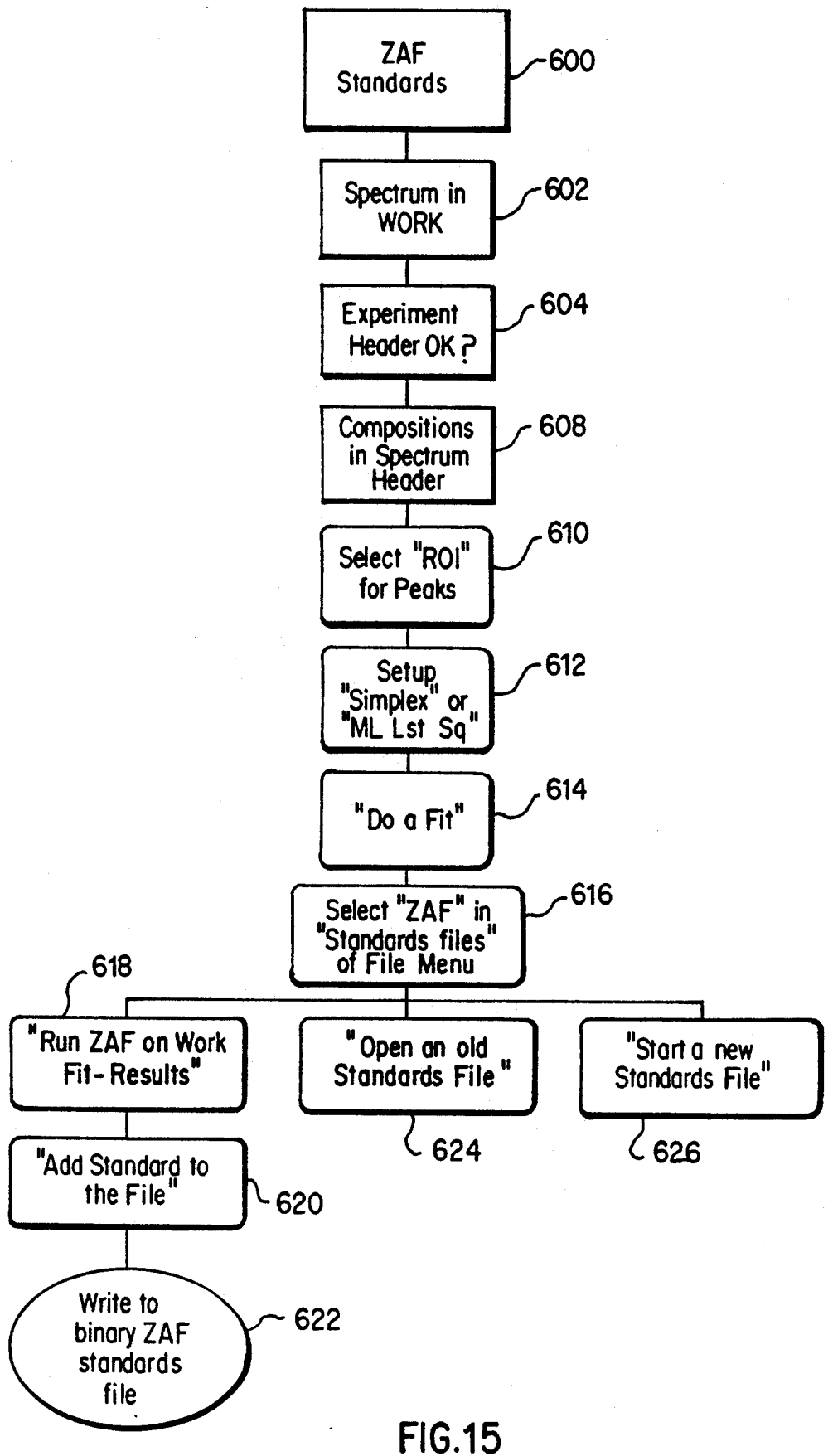
FIG. 15 illustrates the process of performing a ZAF quantitative analysis to make standards data.

FIG. 15 illustrates the procedure 600 of making files of standards data to be used by the ZAF quantitation procedure. In step 602 the spectrum from which the standard data are to be obtained is stored in the Work spectrum display memory. In step 604 the experiment information is verified and modified through the Experiment Header display dialogue. In step 608 the composition of the specimen that produced the spectrum is verified through the Spectrum Header display dialogue. In step 610 peaks to be fit in the procedure are indicated by sweeping (with the mouse) regions of interest encompassing them. In step 612 the Simplex or ML (multiple linear least squares) fitting procedure is setup. The fits to the selected peaks are performed in step 614 and the results are held in memory. In step 616 the option ZAF is selected from the 'Standards Files' choice of the File Menu. In step 624 an old file may be opened to append the new standards data or in step 626 a new file may be created for the data. In step 618 the ZAF quantitation procedure is applied to the fit results held in memory. If the option 620 is chosen, the data is written to the binary file chosen in step 624 or step 626.

Figure 16:
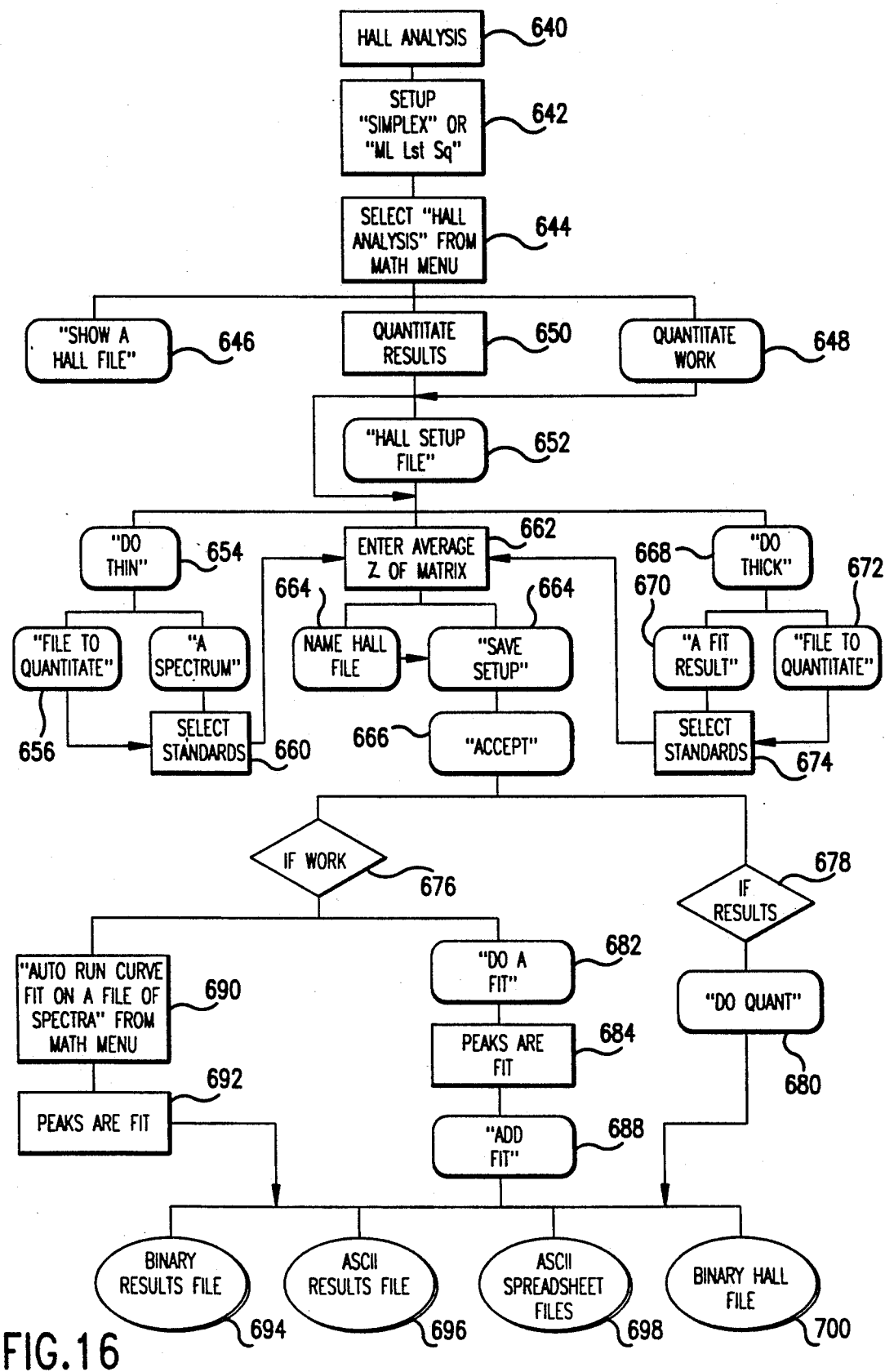
FIG. 16 illustrates the process of performing a Hall quantitative analysis.

FIG. 16 illustrates the procedure 640 for performing a quantitative Hall analysis of spectra from thin biological specimens. In step 642 the Simplex or ML peak fitting procedure is setup, or setup and run on a Work spectrum file. In step 644 the Hall dialogue is presented to the user when 'Hall Analysis' is selected from the 'Analysis' option of the Main Menu. In step 646 the user may choose to examine the results of a previous Hall procedure. To perform a Hall procedure, in step 648 the user selects to quantitate a Work spectrum file or in step 650 selects to quantitate a stored binary ML or Simplex fit results file. In step 652 a file of parameters defined by a previous Hall procedure may be read into memory. The user may then proceed to step 666. In step 654 the user may choose to apply a background correction for a support film. A dialogue is then displayed from which he may choose option 656 to obtain the correction data from the 'File to Quantitate' or option 658 to obtain the data from 'A Spectrum' file selected from the list presented. In step 668 the user may choose to apply a correction for an element not in the specimen but with a contribution to the spectra. A dialogue is then displayed from which he may choose option 672 to obtain the correction data from the 'File to Quantitate' or option 670 to obtain the data from 'A Fit Result' file selected from the list presented. If step 652 was omitted, in step 660 the user selects from a list of fit results files until standards data is found for each element in the spectra or file to quantitate. In step 662 the user enters into an edit text box the average atomic number of the specimen matrix. In step 664 the user enters the name of the file to store the results of the Hall quantitation. In step 664, 'Save Setup', the user saves the defined parameters to a named file. In step 666 the user chooses 'Accept' to retire the dialogue. If option 646 was chosen, in step 678 the selected Fit Results File is opened and in step 680 the Hall procedure is performed using the data in the File to calculate elemental concentrations. If option 648 was chosen, in step 676 the Work spectrum file is opened and the first spectrum is displayed. In step 690 the Hall quantitation procedure is initiated on the file of spectra. In step 692 the peaks in all the files are fit by the procedure selected in step 642 and the concentrations are calculated by the Hall method. The data and concentrations are written to a default binary Hall file or to the file named in step 664; the concentrations are written to the Fit Results File. Alternatively, in step 682 the Hall quantitation procedure is initiated only on the spectrum displayed. In step 684 the peaks in the file are fit by the procedure selected in step 642 and the concentrations calculated by the Hall method. In step 688, the data and concentrations are written to a default binary Hall file or to the Hall file named in step 664; the concentrations are written to the Fit Results File. Other output files are written according to the selections made from the Output Options of the fitting procedure setup: in step 694 a binary fit results file is written; in step 696 an ASCII fit results file is written; in step 698 the spread sheet files are written.

Figure 17:
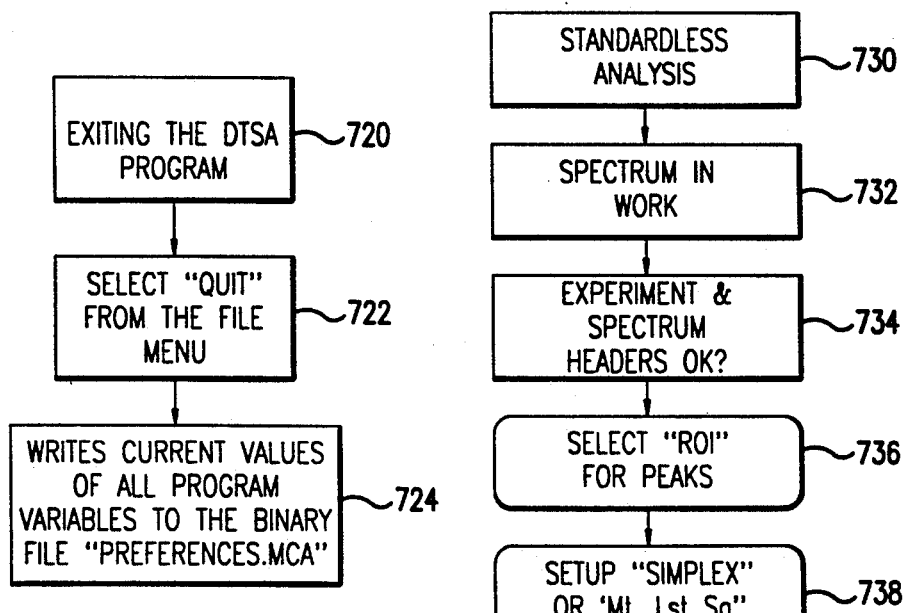
FIG. 17 illustrates the process of making a preference file on program termination.

In FIG. 17 is described the process 720 of exiting from the program. In step 722 the user chooses 'Quit' from the 'File' selection of the Main Menu. In step 724 values of all program parameters are written to the binary file 'Preferences.MCA' and the program terminates.

Figure 18:
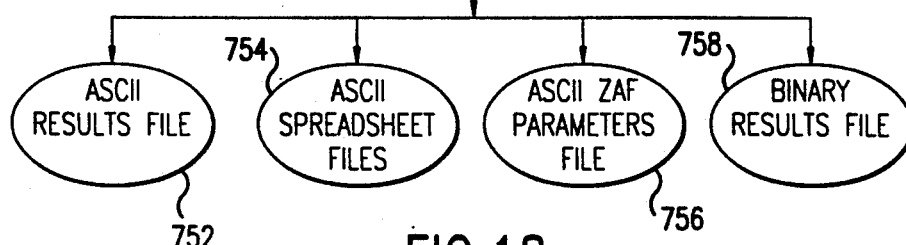
FIG. 18 illustrates the process of performing a ZAF quantitative analysis without measured standards data.

In FIG. 18 a procedure 730 is described for performing a ZAF quantitation without the use of measured standards data. In step 732 a spectrum in the Work spectrum image memory is displayed. In step 734, the Experiment Header and the Spectrum Header dialogues are examined to verify the spectrum file data. In step 736 peaks to be fit and quantitated in the procedure are indicated with the mouse by sweeping regions of interest encompassing the peaks. In step 738 either a Simplex or Multiple Linear Least Squares fitting procedure is setup. In step 740 the user chooses the option to perform procedure 730 from the 'Analysis' selection of the program Main Menu and is presented with a data input dialogue for an element to be quantitated by difference or stoichiometry. In step 742 the user supplies information indicated by that dialogue. In step 744 the user initiates the fitting procedure on the spectrum in Work. In step 744 the peaks are fit and the results are held in memory. In step 748 a ZAF quantitation of the results is performed. In step 750 the user requests that the results of the fitting and the concentration values be appended to a ZAF output file and the files selected from the Output Options of the fitting procedure setup. In step 752 the ASCII results file is written. In step 754 the spread sheet files are written. In step 756 the ZAF results file is written. In step 758 the binary results file is written.

Figure 19:
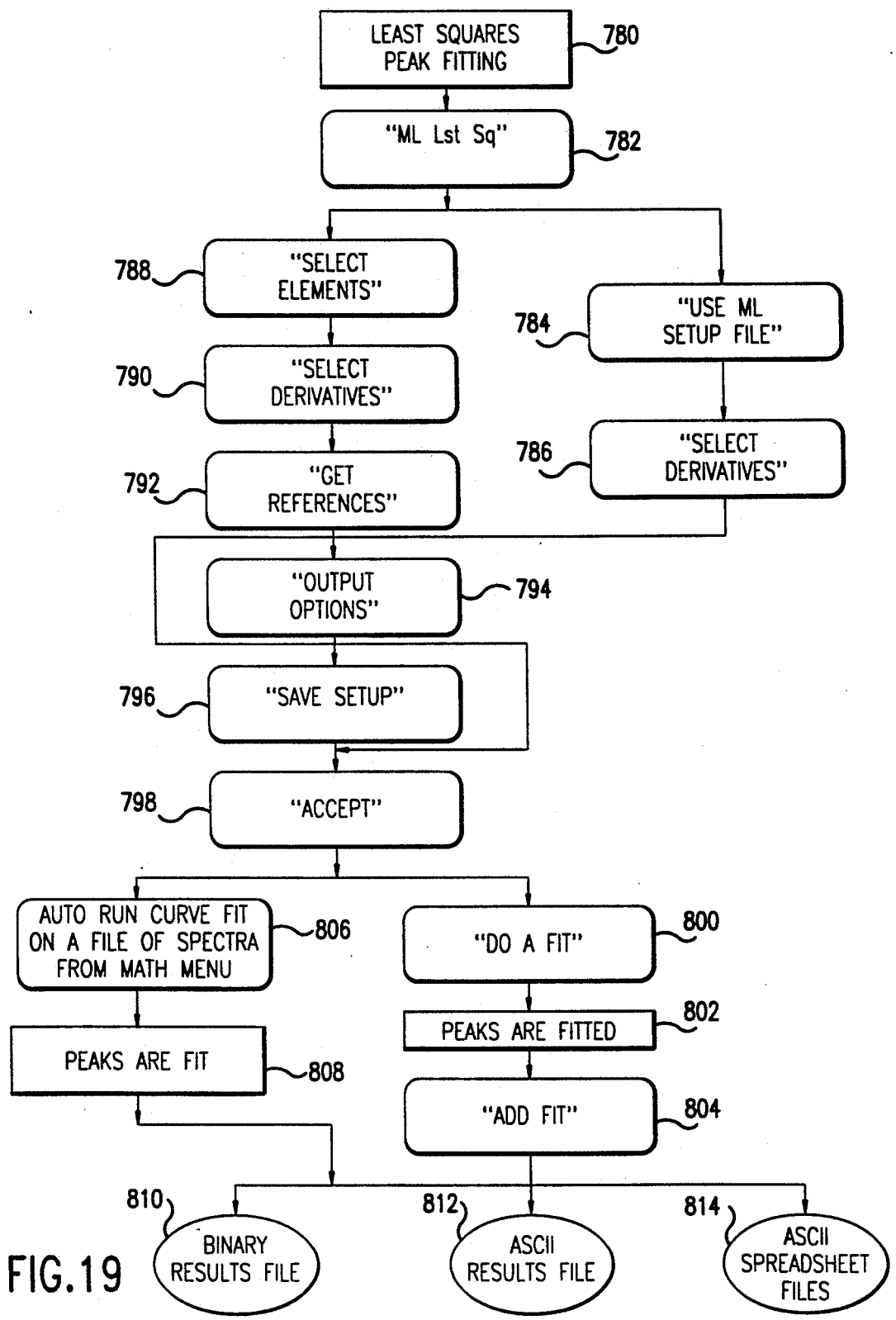
FIG. 19 illustrates the process of fitting spectrum peaks by the multiple linear least squares method.

FIG. 19 describes the procedure 780, Multiple Linear Least Squares Peak Fitting. In step 782 the user selects the procedure and is presented with the setup dialogue. In step 784 the user selects to open a file of required setup data saved from a previous procedure 780. This data includes the families of characteristic lines to be fit in the Work spectrum file, the files of reference distributions to be used, and the derivative references to be included. In step 786 the user may change the set of derivative references. Alternatively, in step 788, the user selects the families of characteristic peaks to be fit in the Work spectrum file. In step 790 the user selects the derivatives of the references to be used in procedure 780. In step 792 the user selects from a list of reference files until references are found for each family of characteristic peaks. In step 794 the user opens the Output Options dialogue and names the files of results to be saved. These may include a binary file, an ASCII file, and any of three popular ASCII spread sheet files. In step 796 the user may save a file of setup data. In step 798 the user accepts the setup and closes the dialogue. In step 806 the user initiates the fitting procedure on the entire Work spectrum file. In step 808 all the fitting procedure is applied to each spectrum in the file and the results are stored in the selected output files. Alternatively, in step 800 the user initiates the fitting procedure on only the spectrum displayed from the Work spectrum image memory. In step 802 the fitting is performed. In step 804 the user commands that the results of the fitting be appended to the selected output files. Results are written to the binary file in step 810, to the ASCII file in step 812, and to the spread sheet files in step 814.

Figure 20:
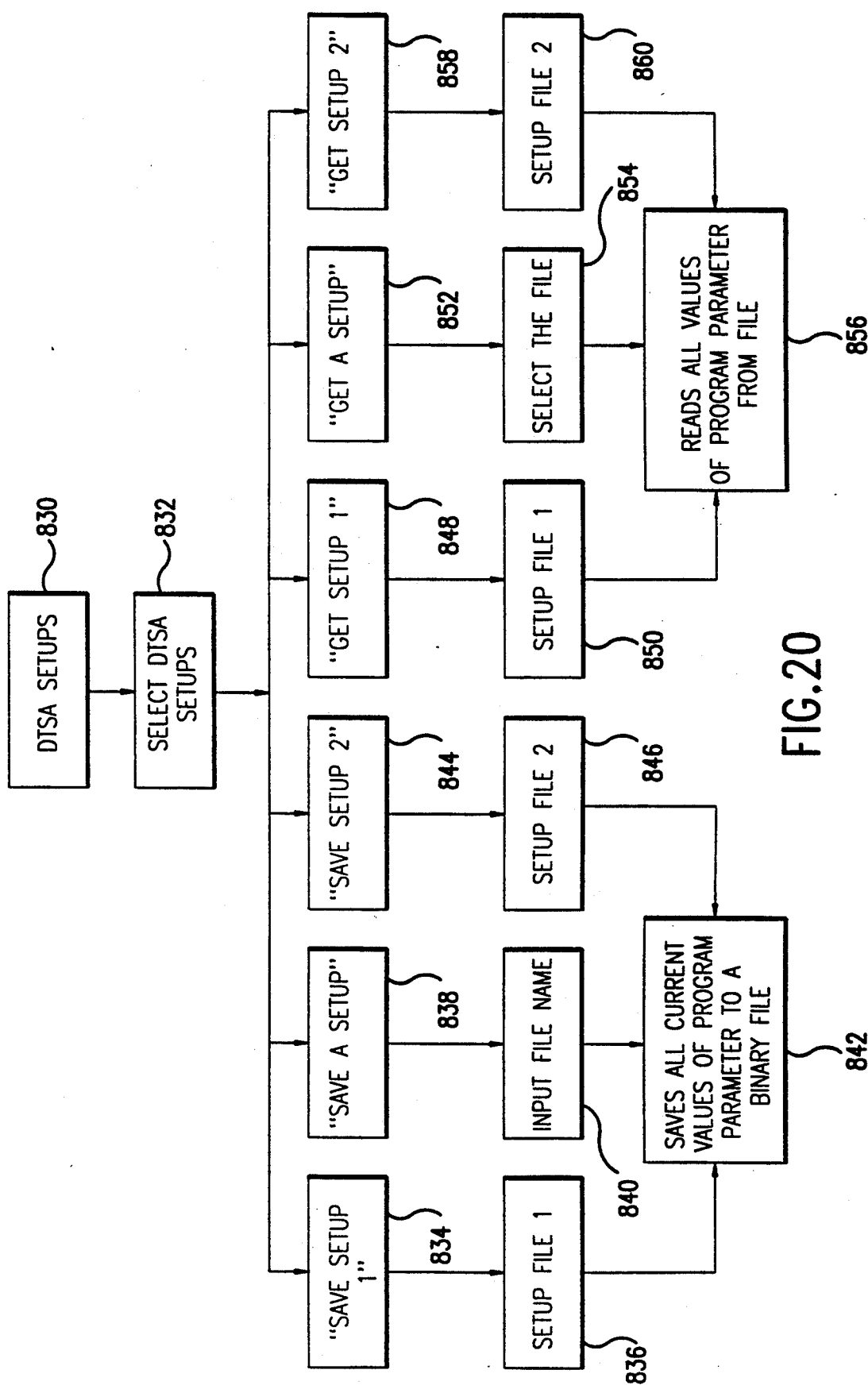
FIG. 20 illustrates processing of preference files.

FIG. 20 describes the procedure 830 by which the set of values for program parameters is read from or written to a binary file. In step 832 the user selects the procedure and is presented with a menu of file options. In step 834 or step 844 one of two default files is selected for writing; or in step 838 the user names a file to be opened for writing. In step 836 or 838 or 846 the selected file is opened. In step 842 the set of current values of all program variables is saved in the selected binary file. Alternatively, in step 848 or step 858 one of two default files is selected for reading; or in step 852 the user names a file to be opened for reading. In step 850 or 854 or 860 the selected file is opened. In step 842 the set of values for all program variables is read from the selected binary file and becomes the active set.

It will be appreciated that data is stored in files in various forms throughout the DTSA. FIG. 21 illustrates, in a Pascal format, the data structure of the experiment header of experiment files, and FIG. 22 illustrates the data structure of the spectrum header of each spectrum file. In the same way, FIG. 23 illustrates the data structure of the multiple linear least squares setup files (ML Setup Files) and the references used in the multiple linear least squares regression. FIG. 24 illustrates the fit results file data structure. FIG. 25 illustrates the file structure for Hall analysis. FIG. 26 illustrates the file structure for ZAF analysis. When analysis is exited on the desk top spectrum analyzer, all critical control parameters are saved in a preference file. FIGS. 27A and 27B illustrate the preference file data structure of the preferred embodiment.

Figure 28:
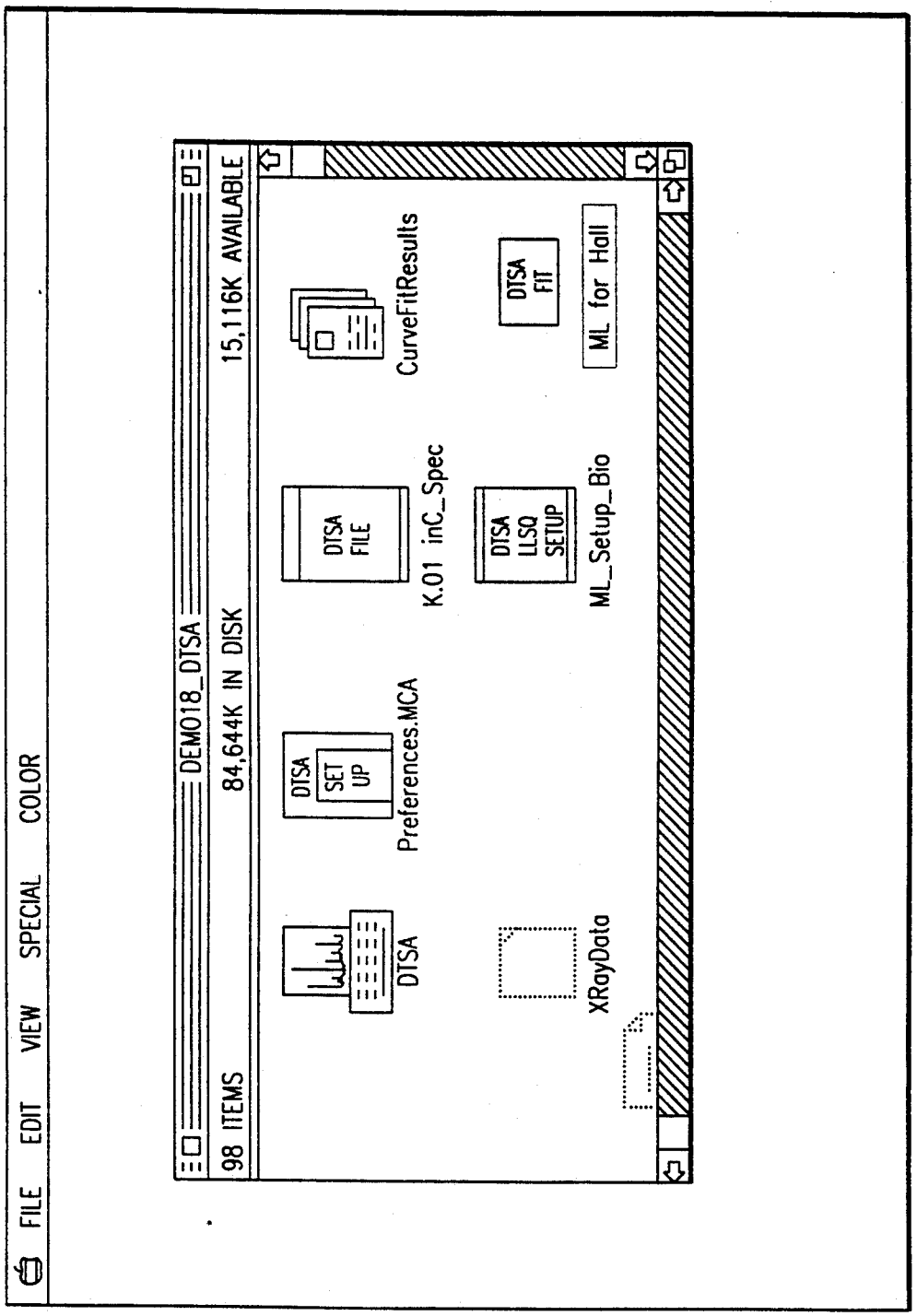
FIG. 28 illustrates the opening display by which the desktop spectrum analyzer is opened.

In the preferred embodiment the desk top spectrum analyzer is implemented in a computer such as a Macintosh computer. FIG. 28 illustrates a display for opening the desk top spectrum analyzer (FIG. 1, element 6) where a user may open the program by selecting the application (DTSA), the default preference file (preferences.MCA), a spectrum file (K.01 in C_Spec), a multiple linear least squares setup file (ML_Setup_Bio), or a binary fit results file (ML for Hall). In the display are also shown the file of x-ray line data use by the program, XRayData, and an ASCII fit results file, CurveFitResults. Upon opening the program DTSA, the display shown in FIG. 29 (also FIG. 3 element 66) appears.

Figure 29:
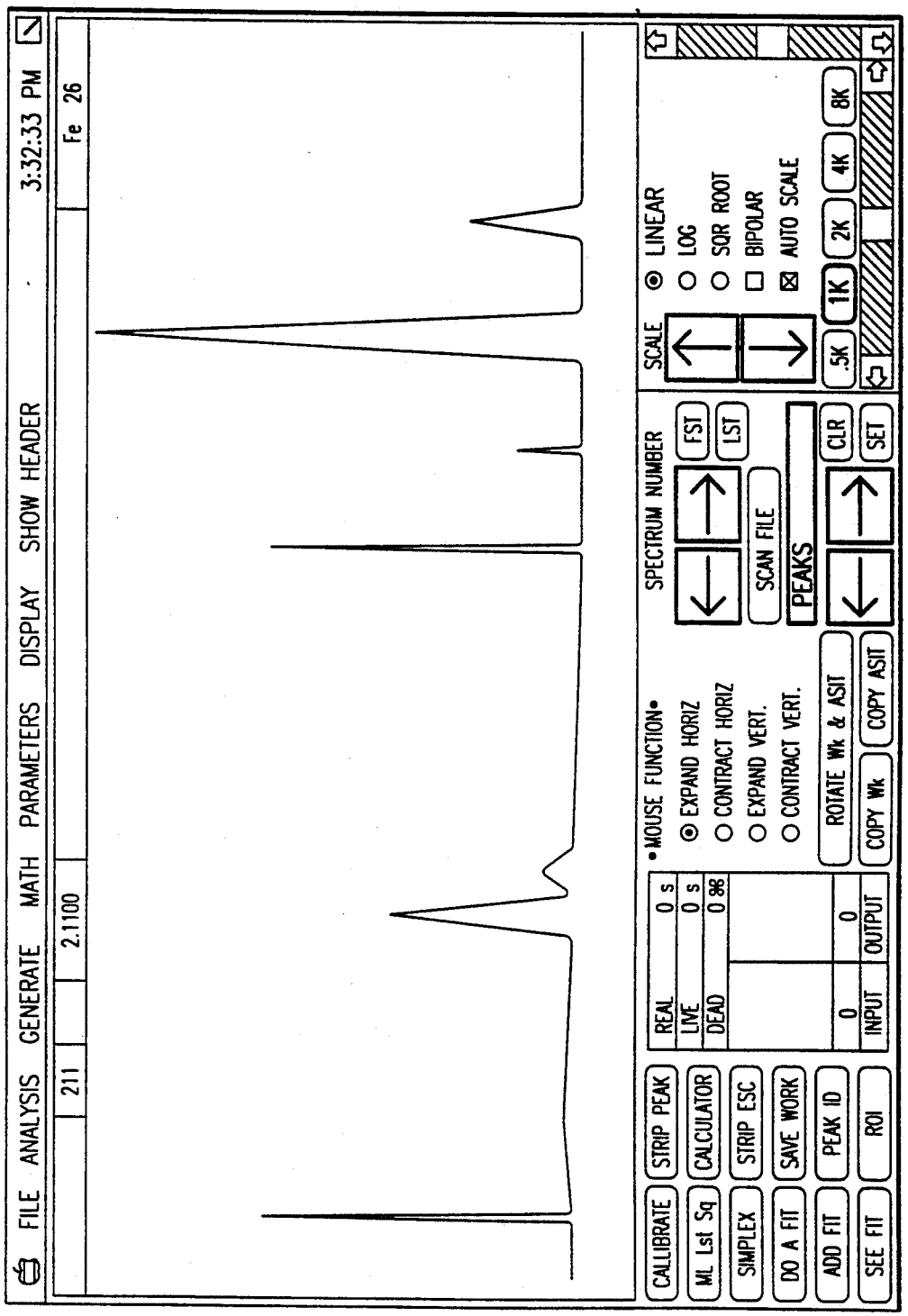
FIG. 29 illustrates the main display of the desktop spectrum analyzer.
Figure 34:
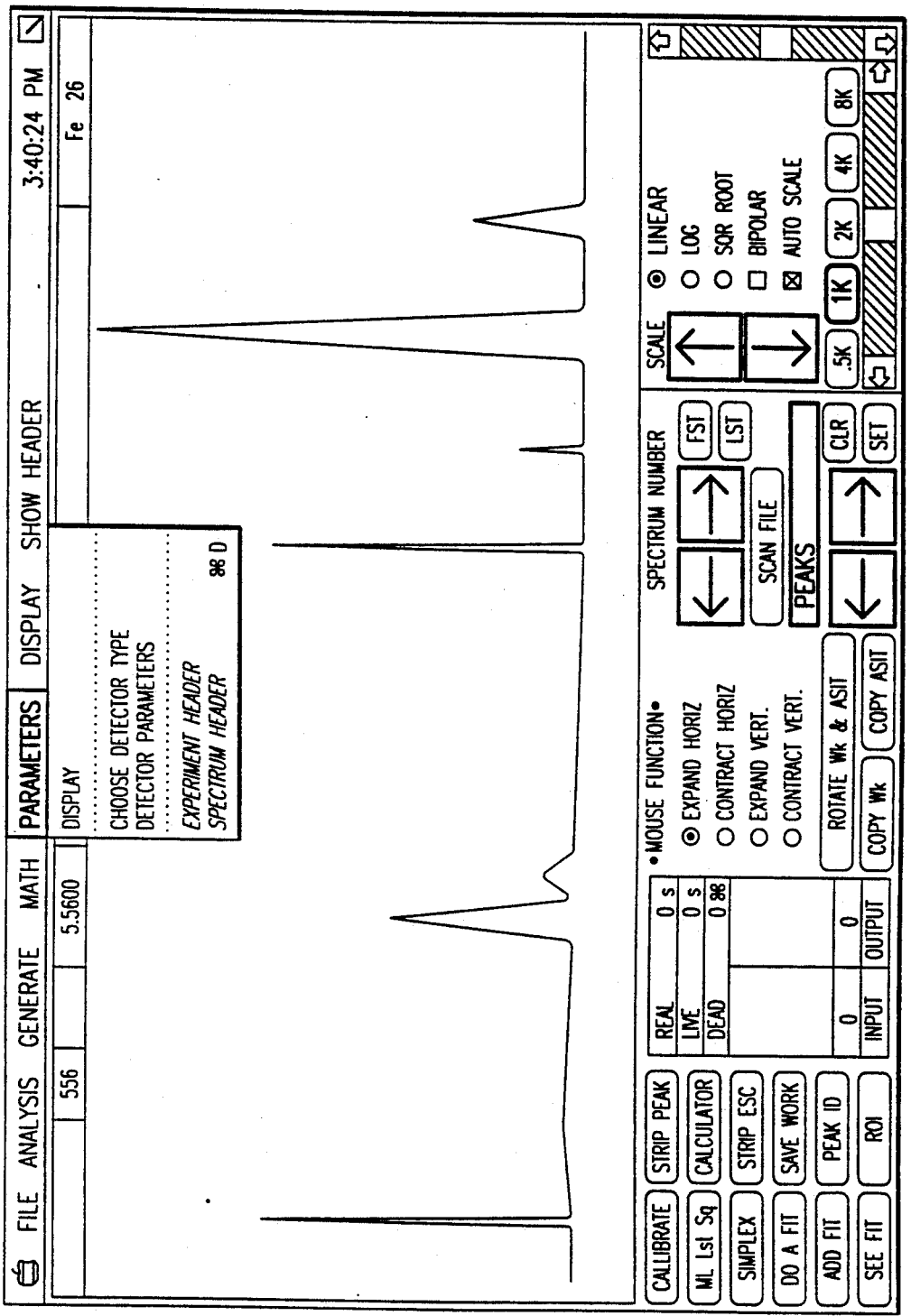
FIG. 34 illustrates the parameters submenu of the desktop spectrum analyzer.

FIG. 29 illustrates a plurality of function choices arranged across the top of the display and in the lower left hand area of the display: File, analysis, generate, math, parameters, display, show header, calibrate, multiple linear least square, simplex, Do a Fit, Add Fit, See Fit, strip peak, calculator, strip escape, save work, peak ID and ROI (region of interest); a spectrum acquisition status "meter"; and a plurality of spectrum display controls in the lower right hand area of the display. Upon selecting each of the menu choices on the top line of the display, a pull down submenu appears as illustrated in FIGS. 30-36. The operator selects from the submenu to set control modes within the desk top spectrum analyzer. For example, the user may access the display illustrated in FIG. 32 to generate one or more spectra from first principles as depicted in element 90 of FIG. 4. FIG. 34 illustrates a reduced intensity submenu label "experiment header" and "spectrum header". This reduced intensity is referred to as "greyed". This indicates that there are no active experiment files open. If an experiment file has been opened, these submenu choices would not be "greyed".

Figure 35:
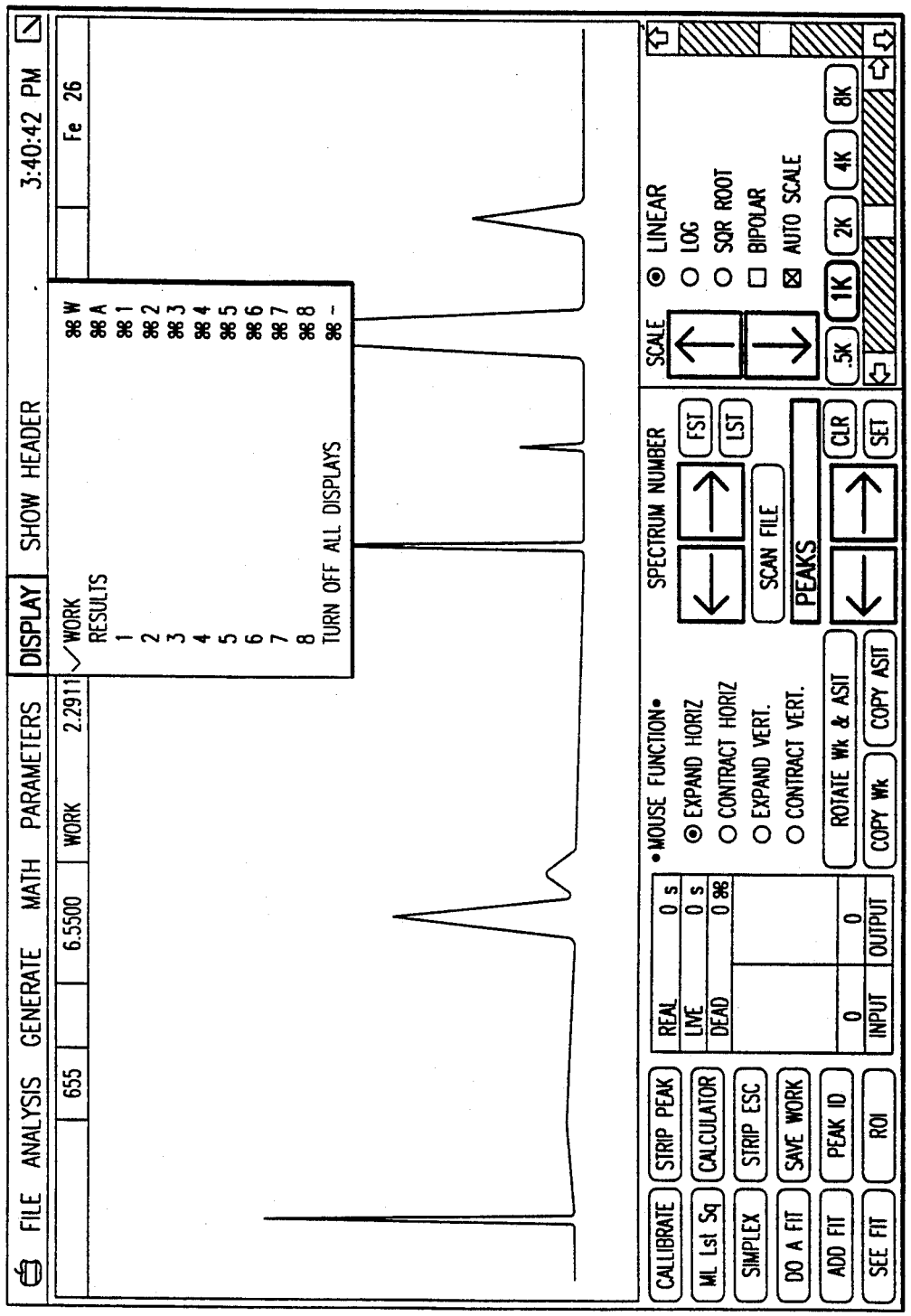
FIG. 35 illustrates the display submenu of the desktop spectrum analyzer.

FIG. 35 illustrates the active display memories (see FIG. 7 element 158). In the figure only the "work" display memory is active and currently displayed.

Figure 36:
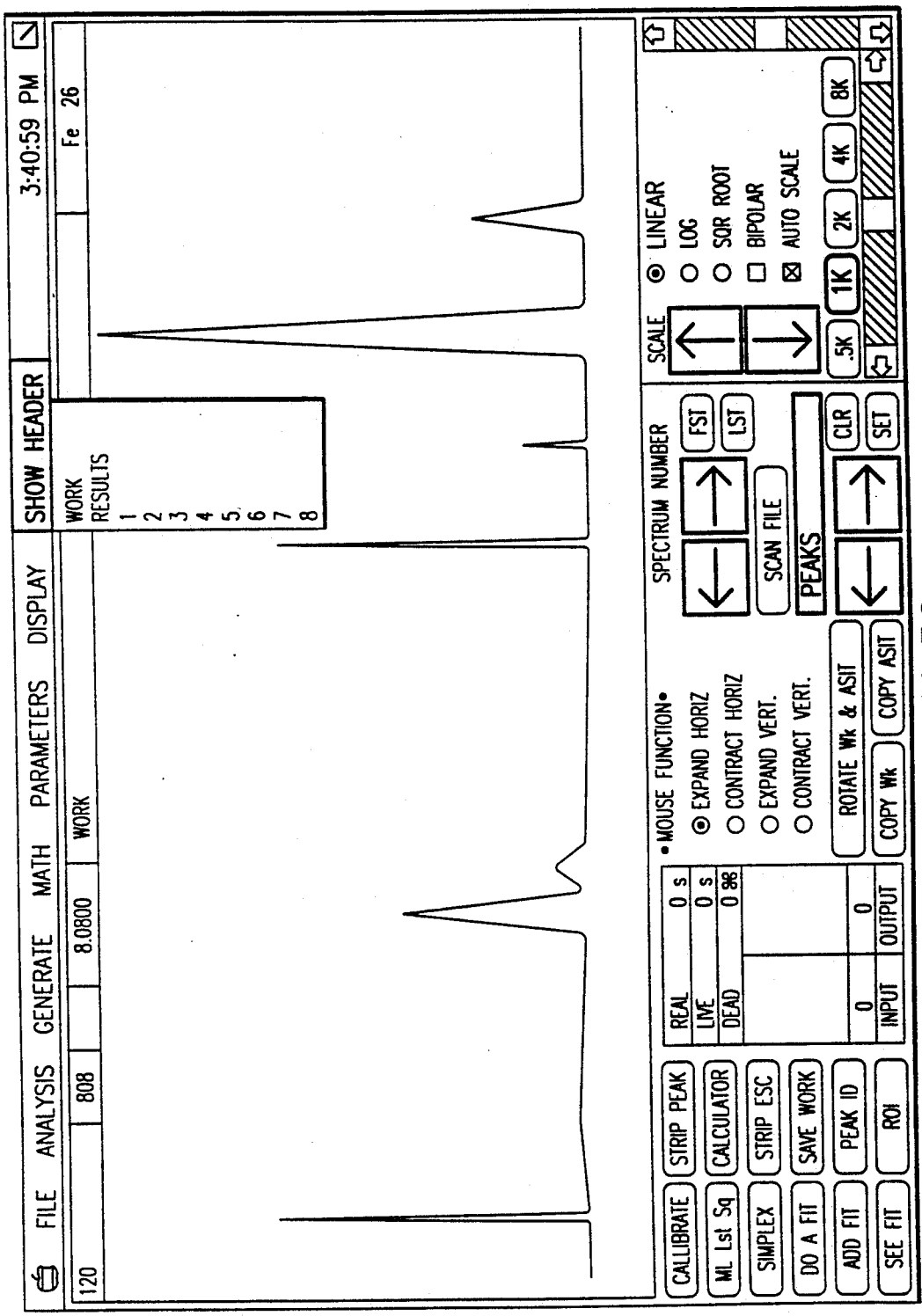
FIG. 36 illustrates the show header submenu of the desktop spectrum analyzer.

FIG. 36 illustrates the submenu by which the user selects headers corresponding to one of the image memories for display in text format.

Figure 37:
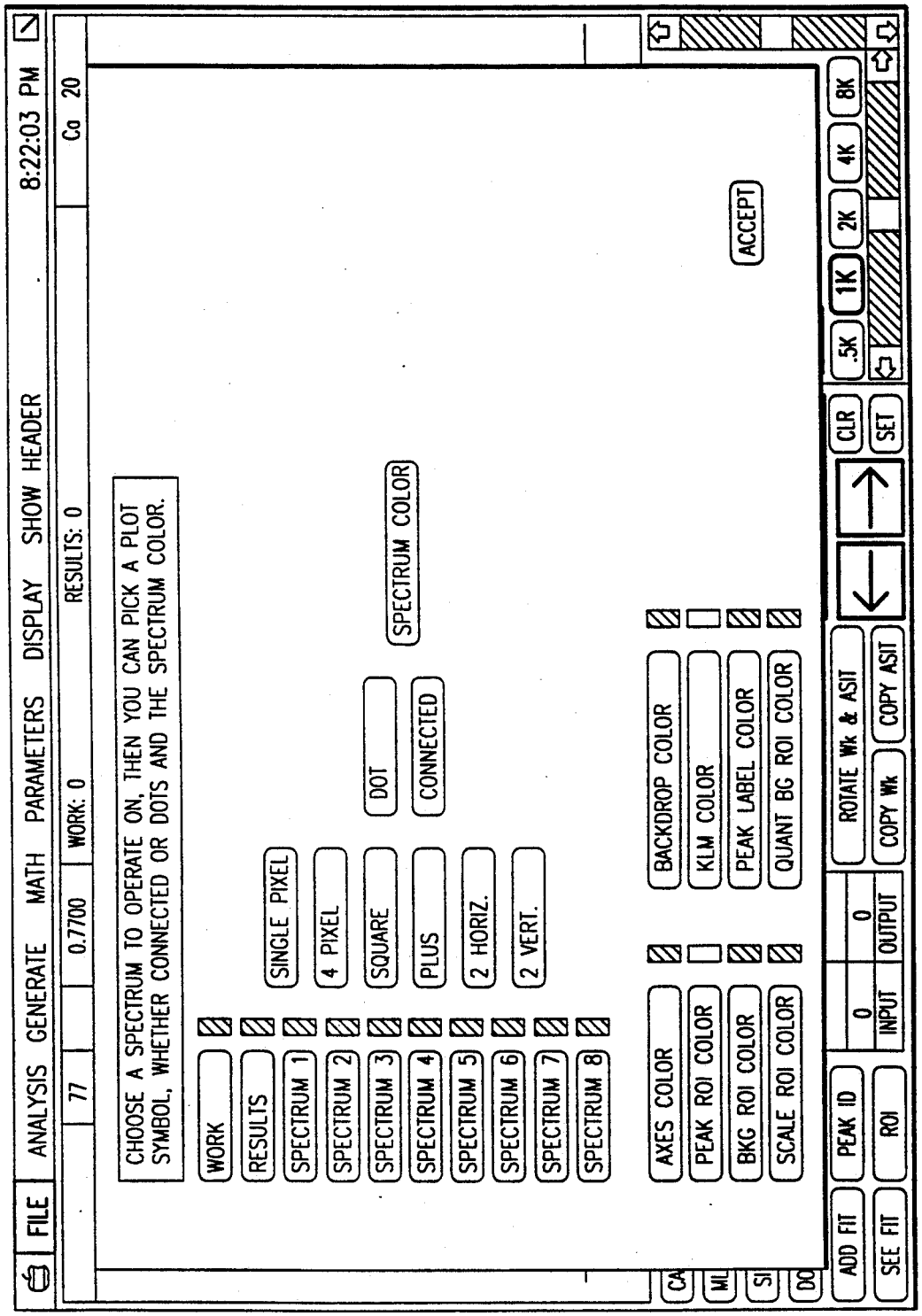
FIG. 37 illustrates the display options dialogue interface.

Many of the submenu choices open additional submenus or create dialogue interfaces for the user to set input data. FIG. 37 illustrates a dialogue interface opened when the "display options" submenu choice was selected from the file submenu illustrated in FIG. 30. From this dialogue interface, the user can select a spectrum, plot symbols, line connect choices and spectrum color with which to display the selected spectrum.

FIG. 38 illustrates a dialogue interface opened from the generate submenu. In this interface, the user can select the fractional weight composition of a plurality of constituent elements to be used for the generation of a theoretical spectrum from first principles. FIG. 38 indicates that a sample of 100% potassium is to be used to generate the theoretical spectrum. FIG. 39 illustrates the next dialogue interface where the user is prompted to indicate the destinations for the selected steps or functions related to generation results.

Figure 41:
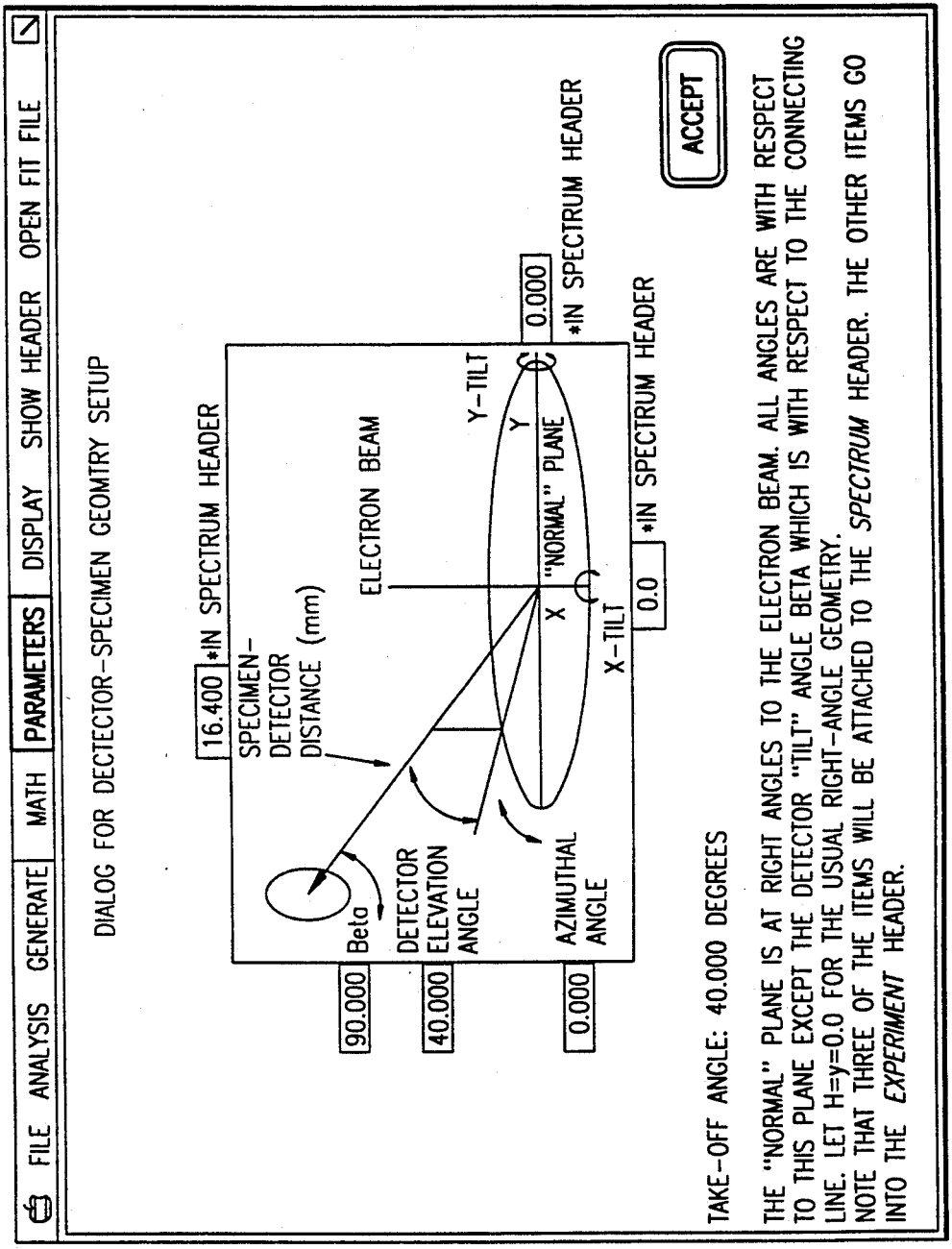
FIG. 41 illustrates the detector-specimen geometry dialogue interface of the detector parameters dialogue interface of the parameters submenu.

FIG. 40 illustrates a dialogue interface reached by selecting parameters and then selecting detected parameters. In this dialogue interface the user is prompted to define the detector to be used in the experiments performed. FIG. 41 illustrates the dialogue interface used to define the detector-specimen geometry setup. The display includes a normal plane containing the specimen on which an exciting beam impinges. The detector is located at an azimuthal angle and detector elevation angle which the user may define.

Figure 42:
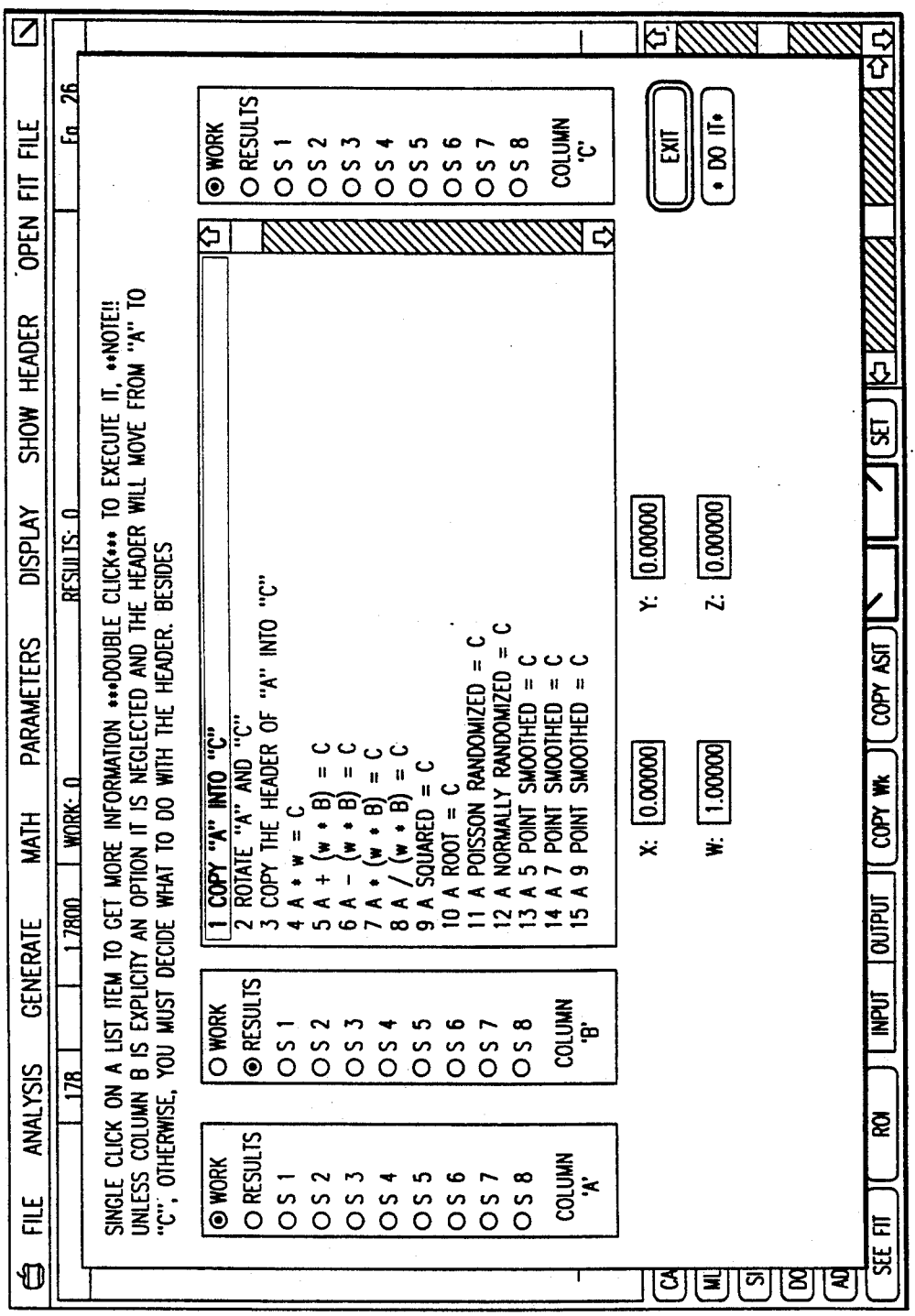
FIG. 42 illustrates the calculator dialogue interface.

FIG. 42 illustrates a calculator dialogue interface accessed by selecting the calculator choice in the lower left hand area of the display illustrated in FIG. 29. With the calculator dialogue the user may select two input operands (column A and column B) and an output (column C). The operands in this case are spectra contained in one of the plurality of image memories (FIG. 7, element 158). The user may then select the operation to be performed. Fifteen operations are indicated in FIG. 42. However, FIG. 42 illustrates a scroll window that displays only fifteen of a plurality of options where the plurality exceeds 15. Having selected the operation, the user next selects to "do it".

FIG. 43 illustrates a dialogue interface entered by selection from the math submenu. The dialogue is for converting a wavelength dispersive spectrum to an energy dispersive spectrum. The user selects the wavelength units of the spectrometer that produced the wavelength dispersive spectrum, and selects to convert either the X and Y axes, or the X axis only. The user then enters the beginning and ending channel for the wavelength dispersive spectrum, the values of the beginning and ending channels, and the channel width. The user then selects the crystal type used in the wavelength dispersive spectrometer and default $2d$ the spacing of the crystal is entered by the program and may be changed by the user.

Figure 44:
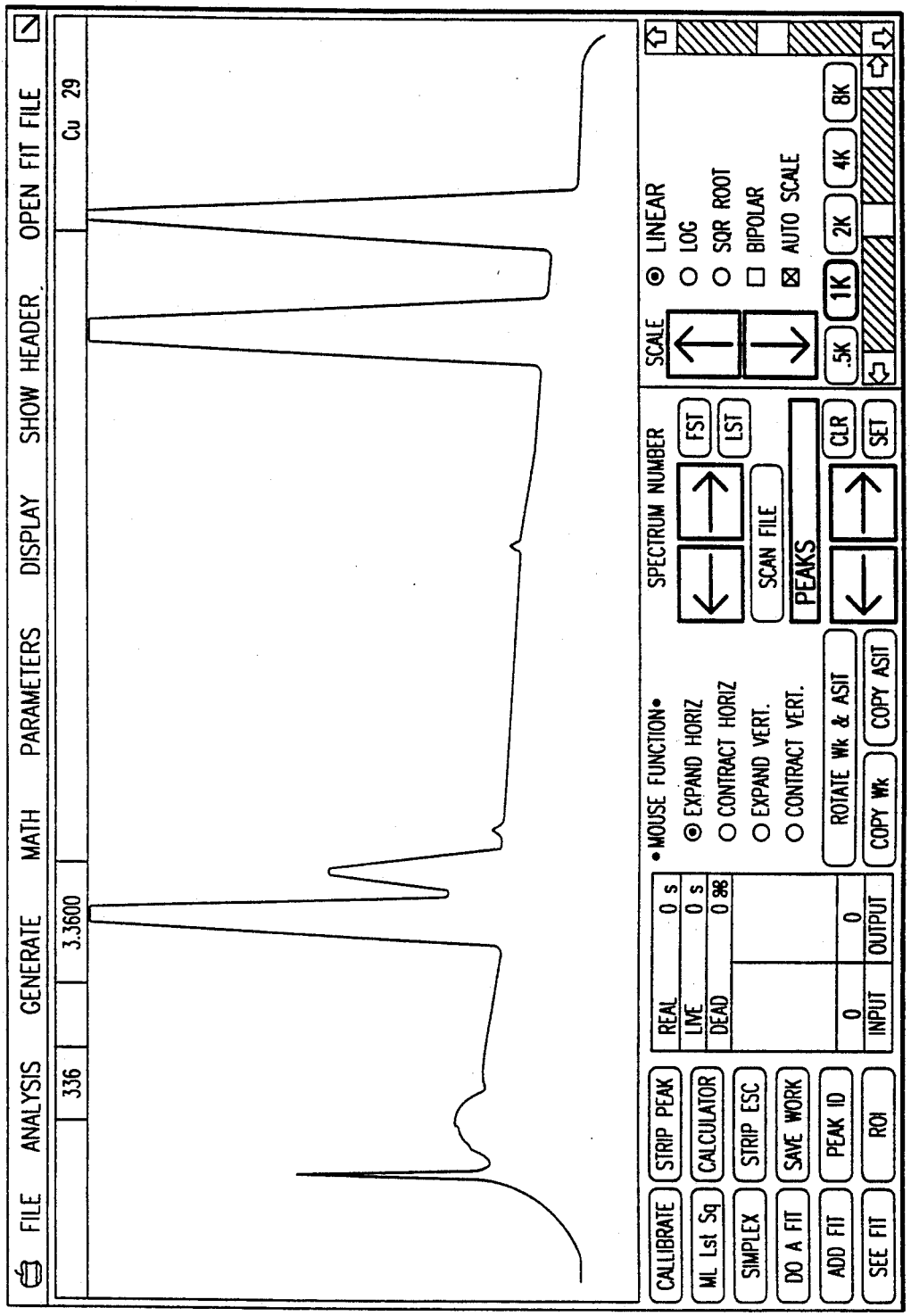
FIG. 44 illustrates the overlayed display.

FIG. 44 illustrates the overlap display 160 of FIG. 7. The display illustrated is the result of fit processing. For example, on the left hand half of the display, a double peak is illustrated. The peak has been labeled K $K_\alpha$, K $K_\beta$, Ca $K_\alpha$ and Ca $K_\beta$. At the bottom of the double peak is a small "bumpy" line and a smooth line. The bumpy line is the residual after a properly scaled K and a properly scaled Ca reference have been subtracted from the work spectrum. The smooth line is a best fit "smoothed" residual. The line markers are set on Cu 29 as is indicated in the upper right hand corner of the display.

Figure 45:
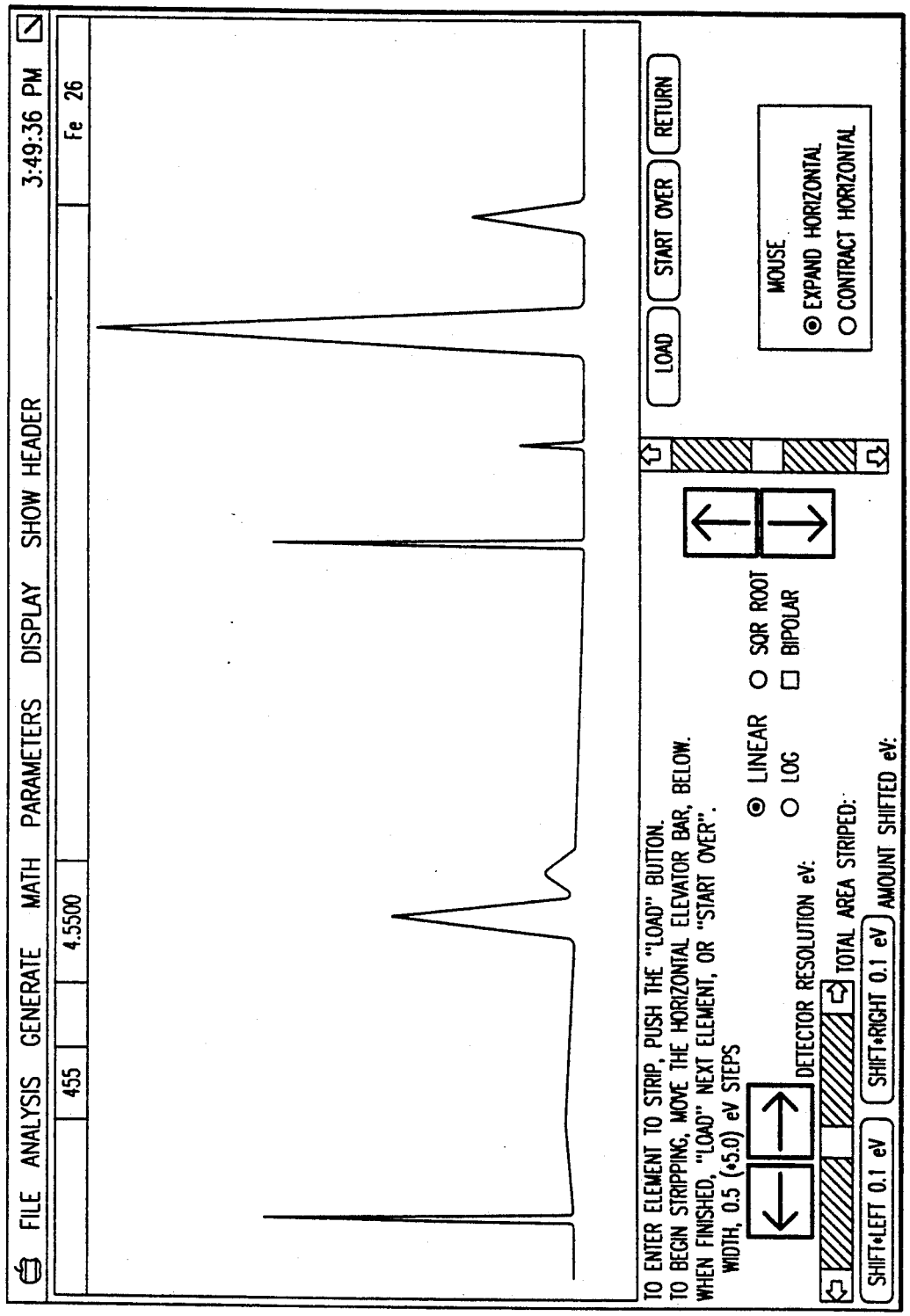
FIG. 45 illustrates the dialogue interface for the strip peaks menu selection.

FIG. 45, lower section, illustrates the dialogue interface produced when the "strip peak" choice is selected from the lower left hand corner menu of the display illustrated in FIG. 29.

FIG. 46 illustrates the output results displayed according to the process of FIG. 10 step 404.

Figure 47:
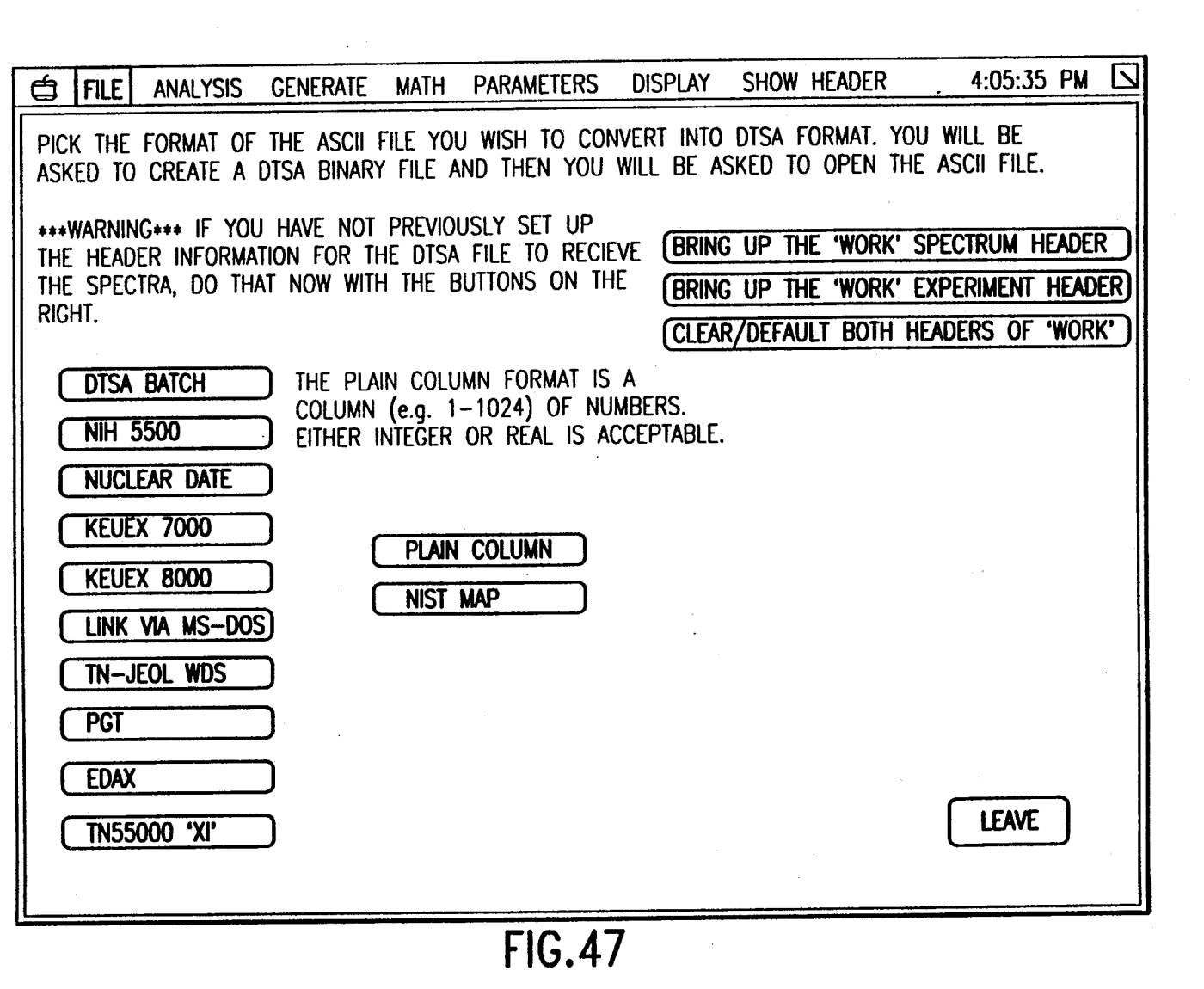
Figure 48:
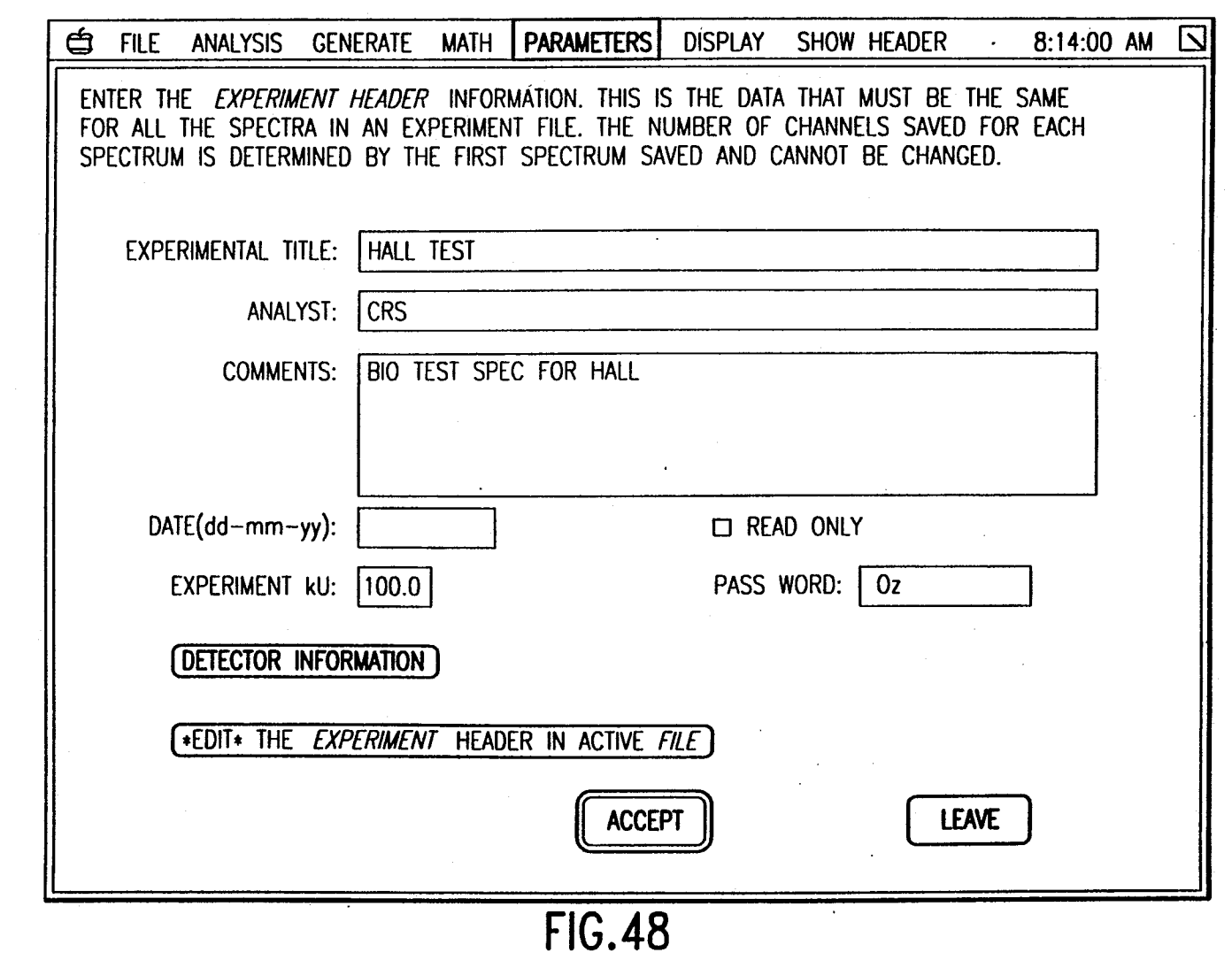

FIG. 47 illustrates the dialogue interface that is produced at step 432 of FIG. 11. FIG. 48 illustrates the dialogue interface produced at step 436 of FIG. 11, or other steps where the experiment header may be accessed or modified.

Figure 49:
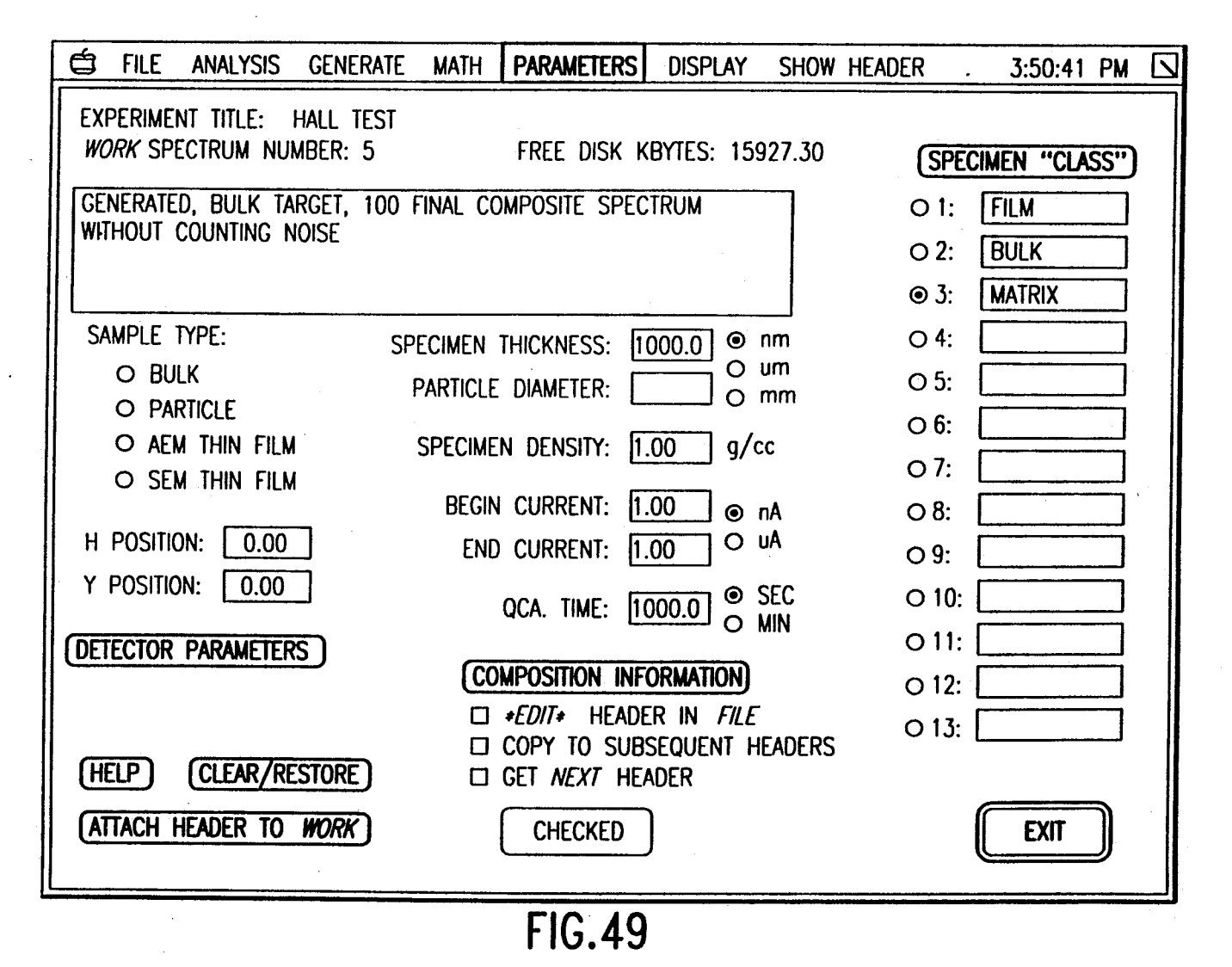

FIG. 49 illustrates the dialogue interface produced at step 434 of FIG. 11, step 734 of FIG. 18, or other steps where the spectrum header may be accessed or modified.

Figure 30:
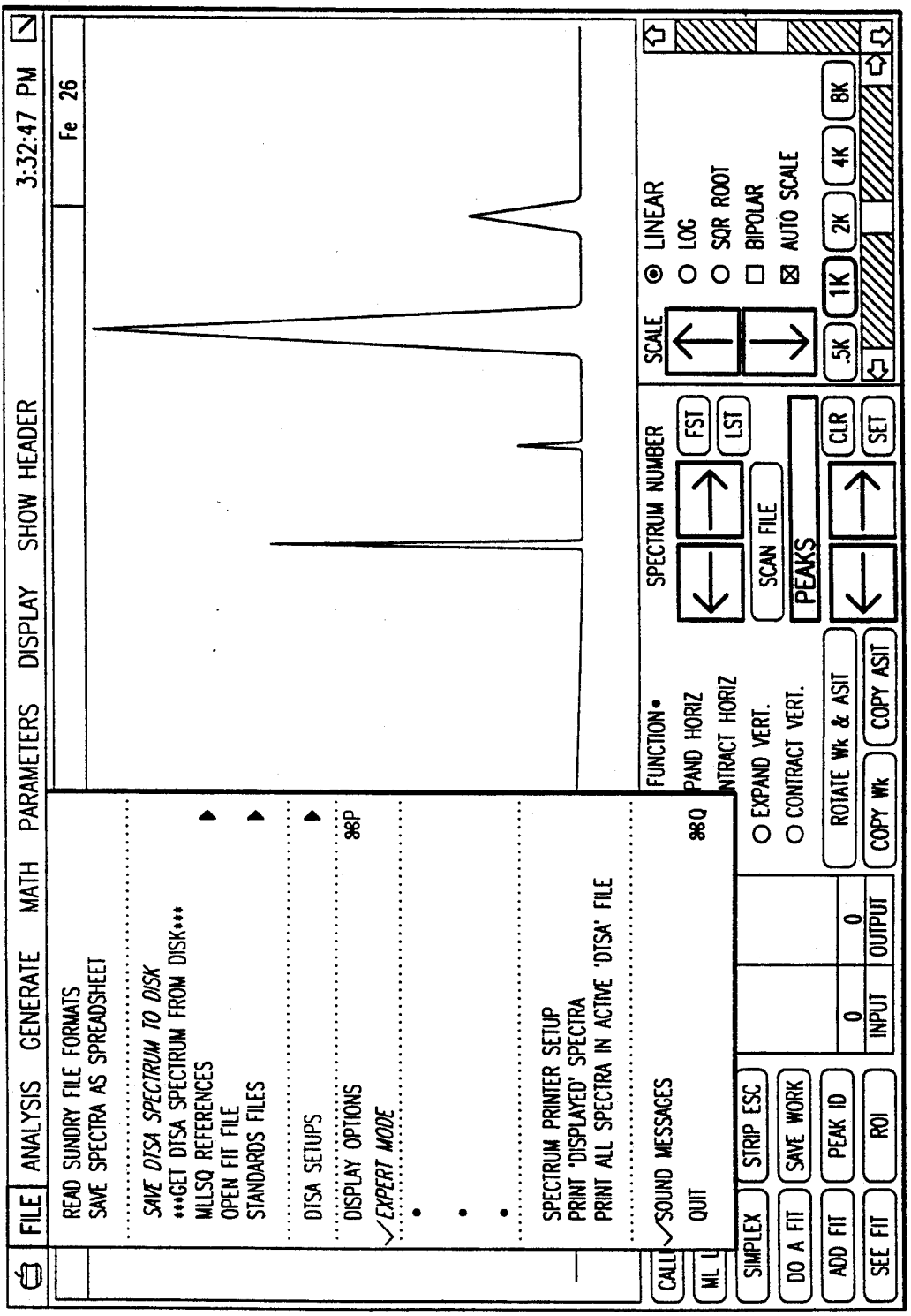
FIG. 30 illustrates the file submenu of the desktop spectrum analyzer.
Figure 31:
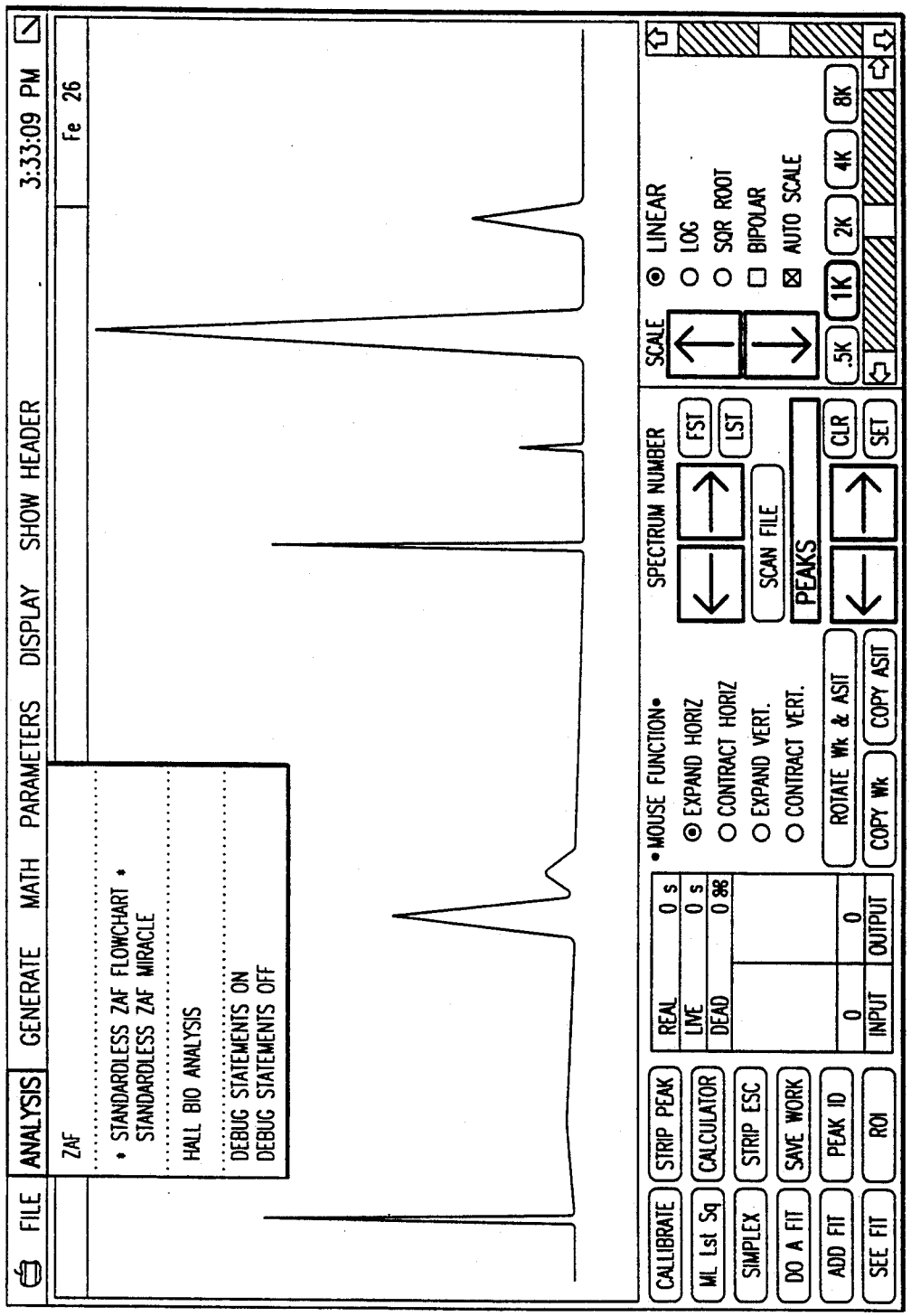
FIG. 31 illustrates the analysis submenu of the desktop spectrum analyzer.
Figure 32:
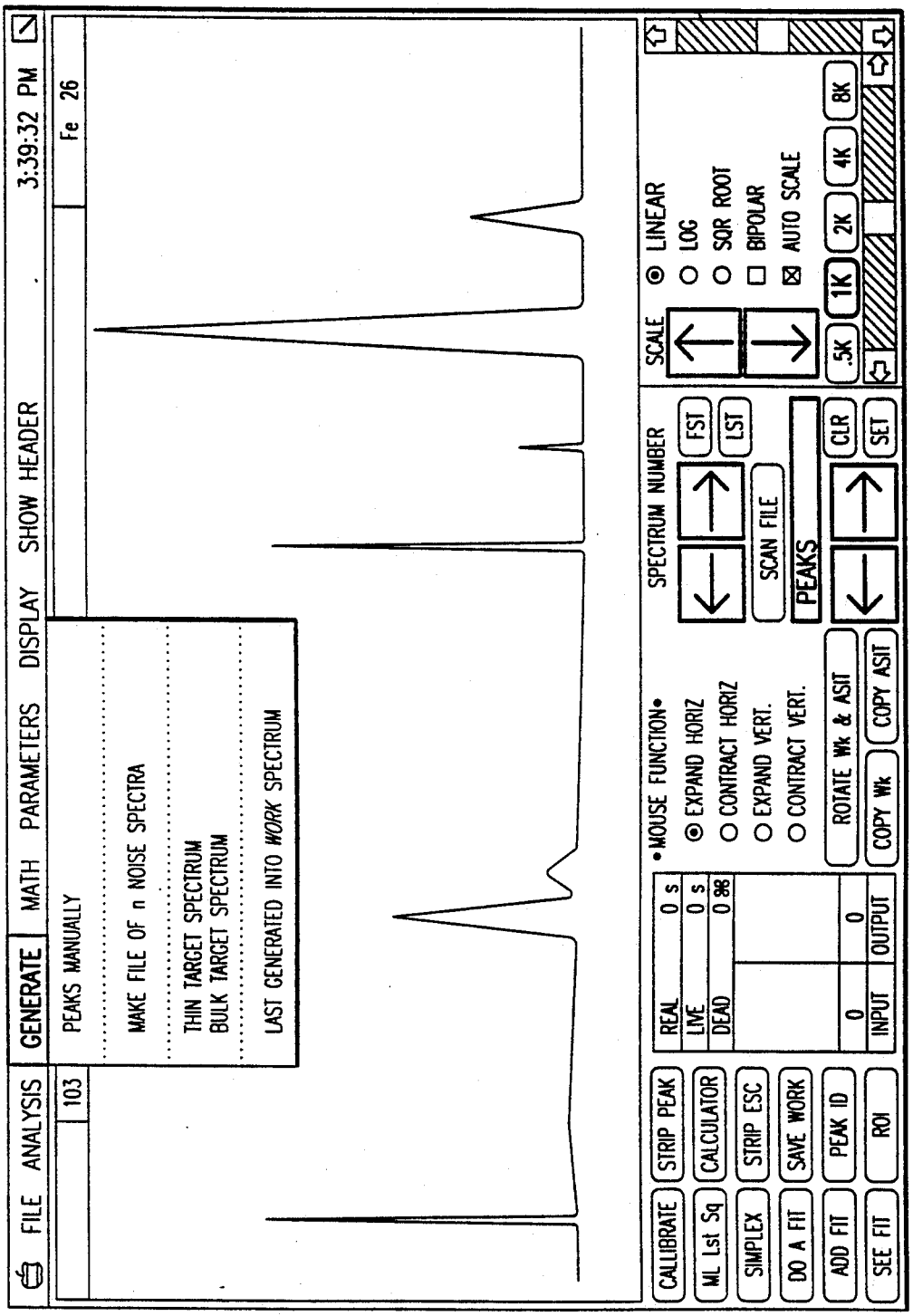
FIG. 32 illustrates the generate submenu of the desktop spectrum analyzer.
Figure 33:
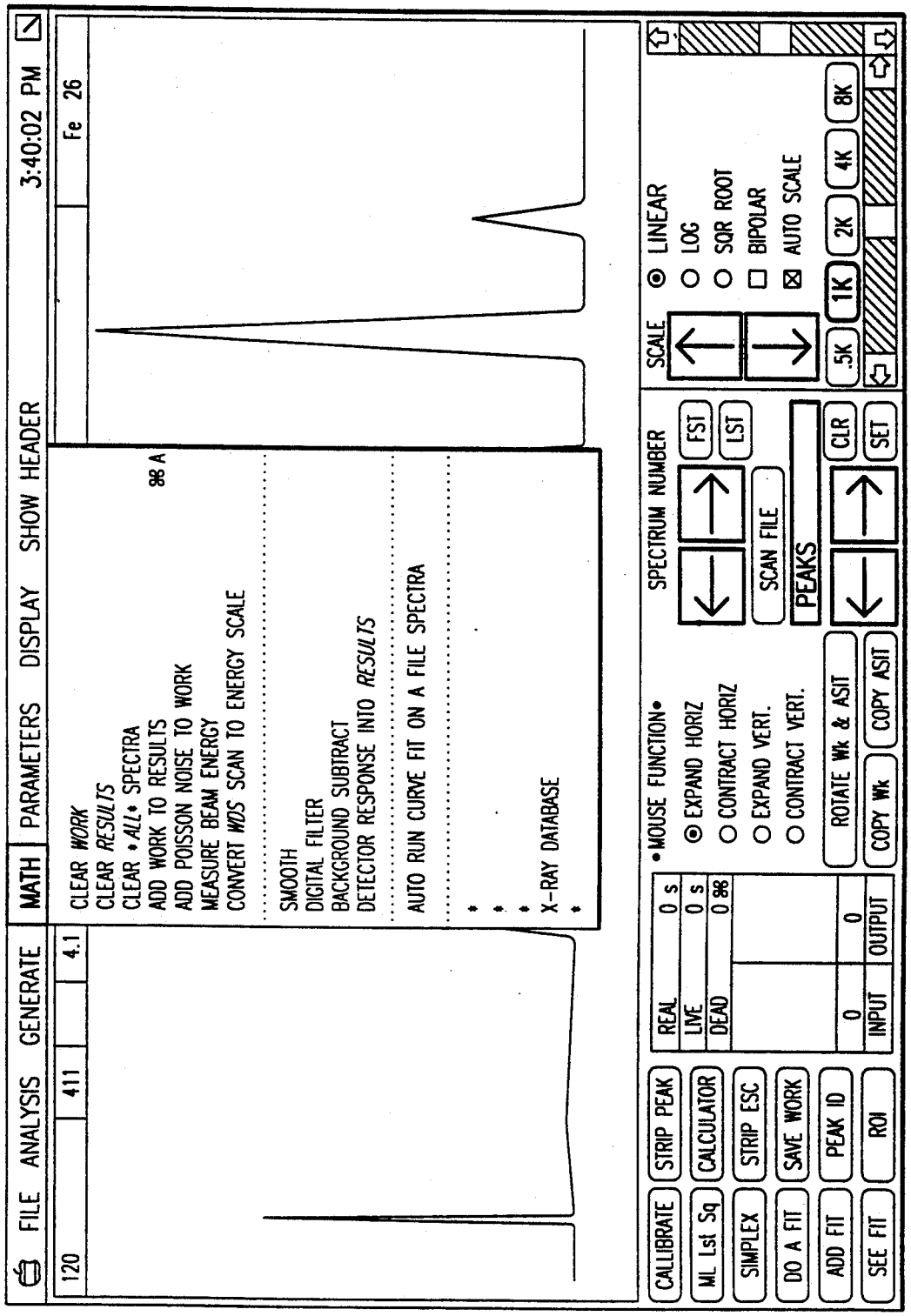
FIG. 33 illustrates the math submenu of the desktop spectrum analyzer.
Figure 50:
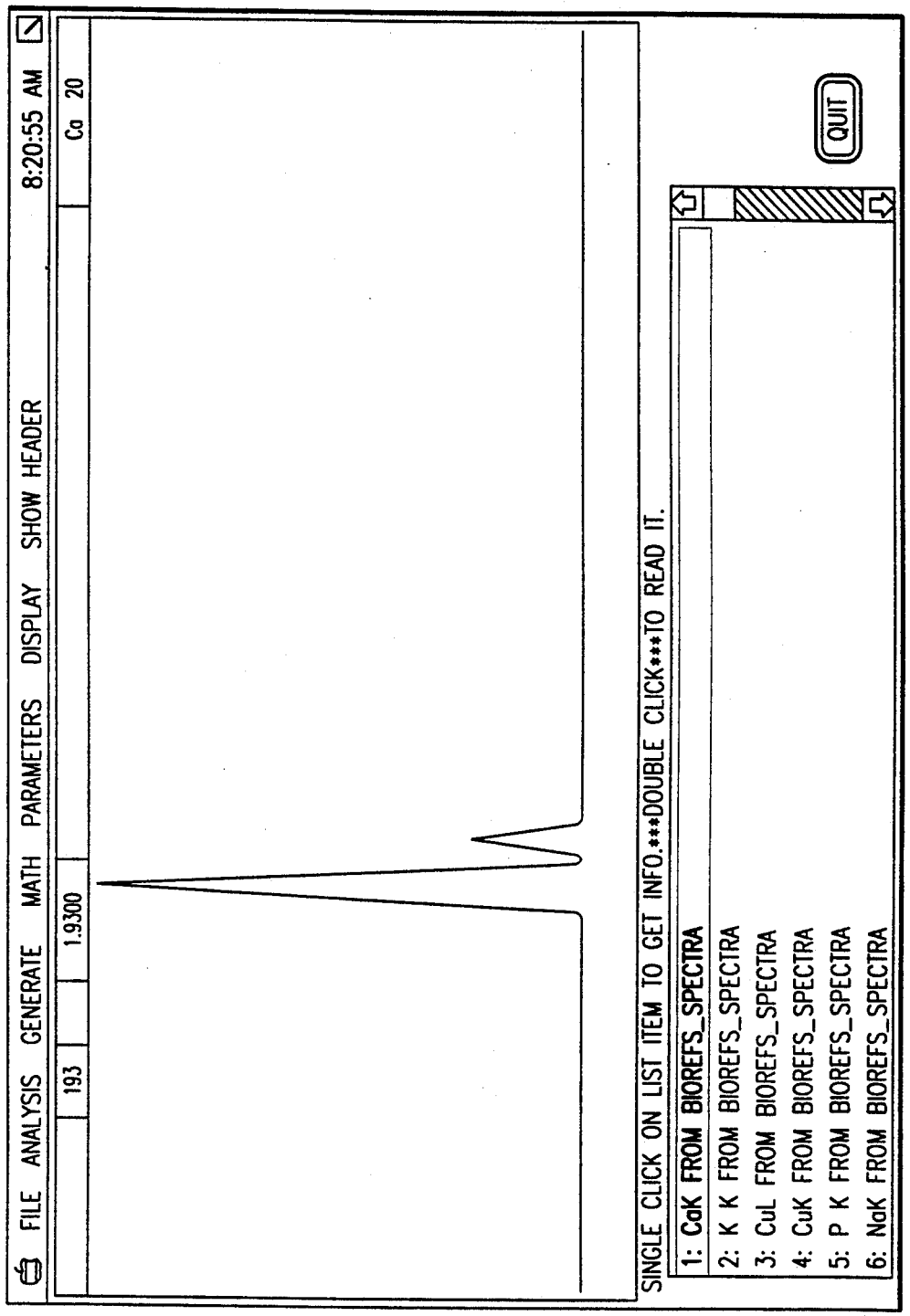
FIG. 50 illustrates a menu for choosing references to display and the reference display.

FIG. 50 illustrates the display of a reference and a dialogue interface for choosing a reference to display. This display is accessed by selecting the file submenu as illustrated in FIG. 30, then selecting the MLLSQ references choice in the file submenu which produces a small three choice peripheral menu, one choice of which is display reference. This choice leads to the display indicated in FIG. 50. Display indicated in FIG. 50 may also be produced from step 476 of FIG. 12.

FIG. 51 illustrates a dialogue interface for the user to select "background subtract" as indicated at step 466 in FIG. 12.

Figure 52:
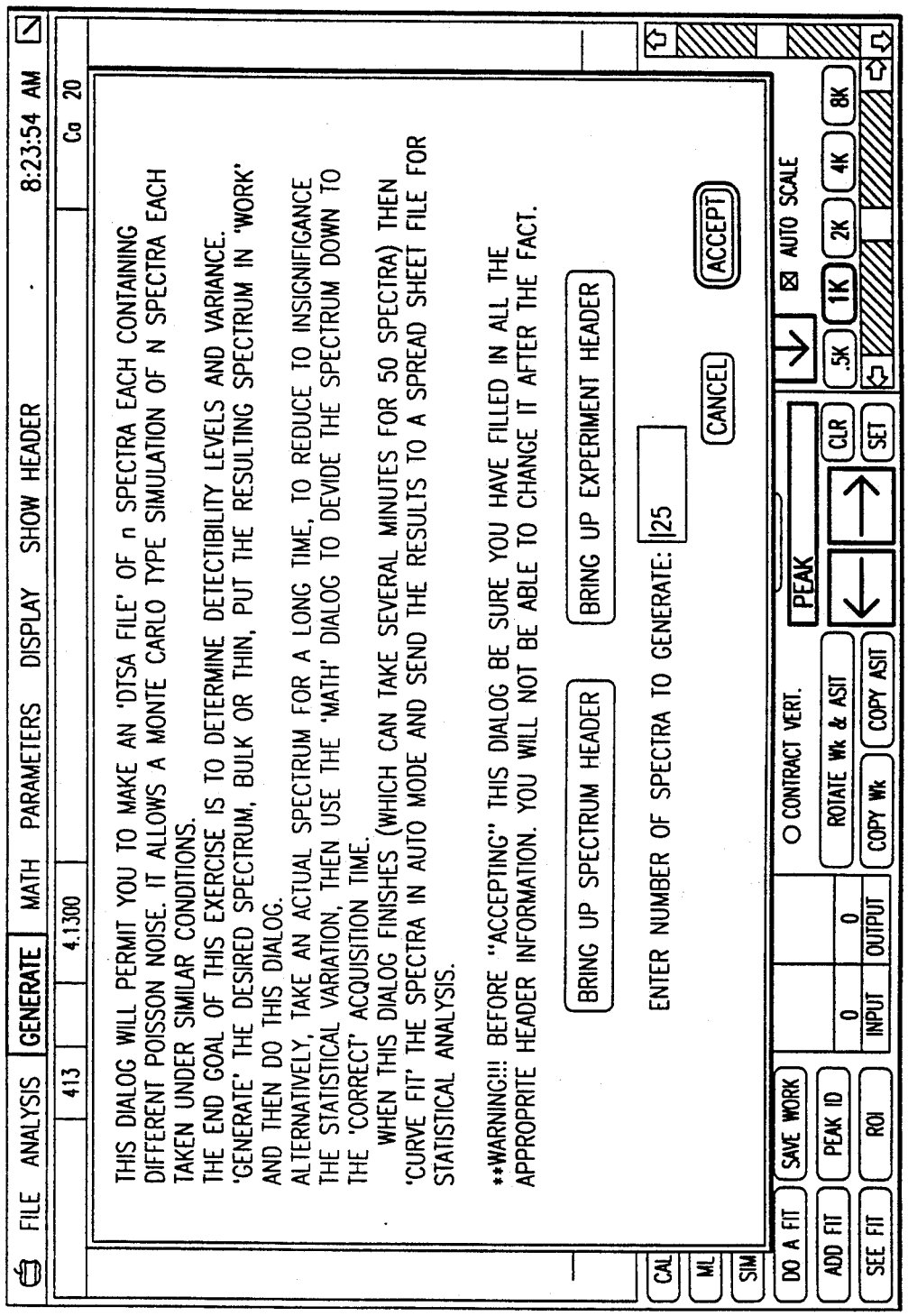
FIG. 52 illustrates a dialogue interface for defining statistical parameters to compute variance and minimum detectable limits.

FIG. 52 illustrates a dialogue interface for the user to generate a plurality of spectra, each spectrum containing Poisson counting noise. The plurality, preferably 25 or more, of spectra are used for statistical determination of variance and minimum detectable limit (MDL).

Figure 53:
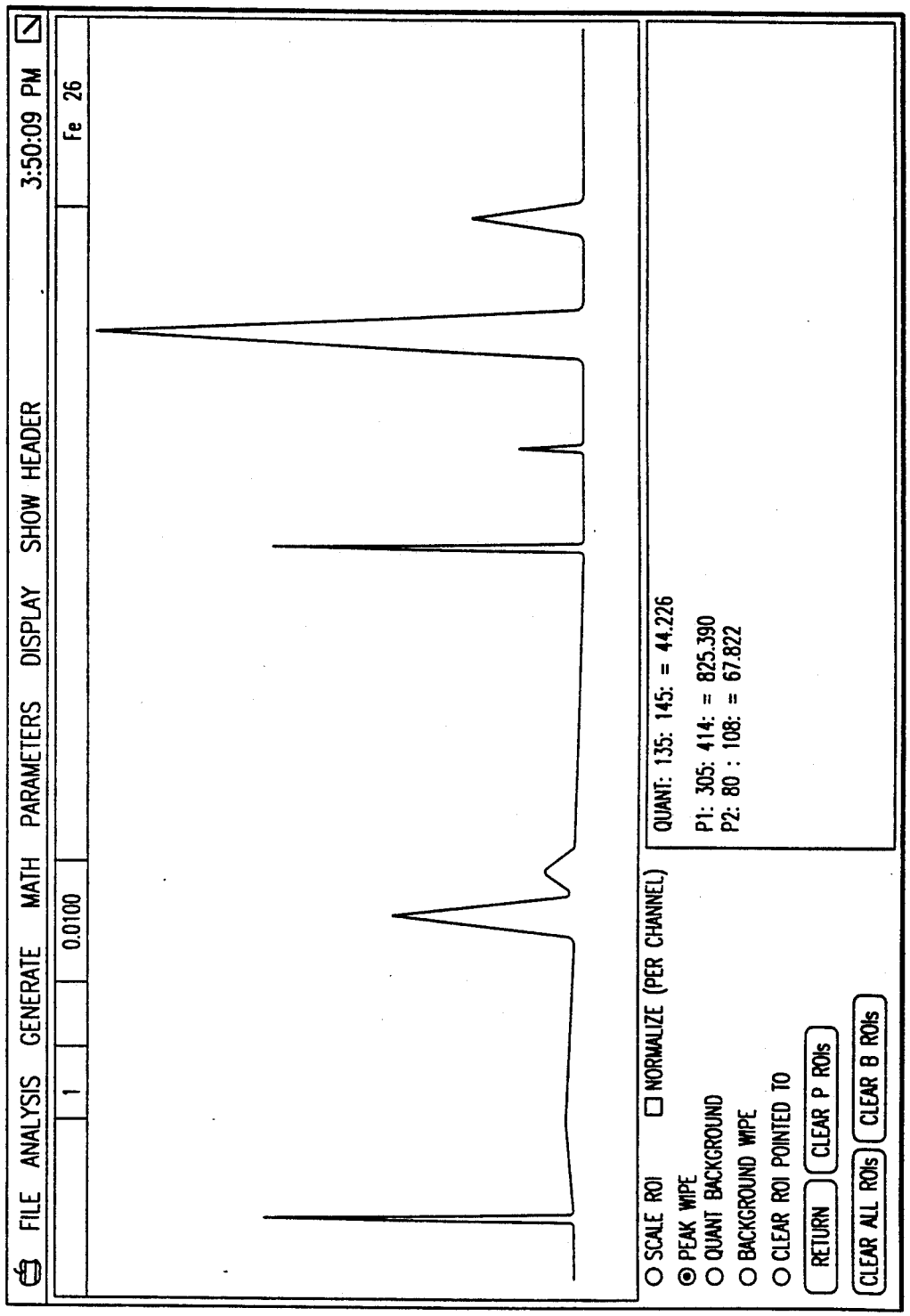
FIG. 53 illustrates the display for selecting a region of interest (ROI)

FIG. 53 illustrates the interface by which the user selects a region of interest such as indicated in step 464 of FIG. 12, step 504 of FIG. 13 and step 610 of FIG. 15. Preferably, this interface employs a mouse and cursor controlled by the mouse for "sweeping the region of interest". Upon such selection, the display will be brightened in the region of interest or the color in the region of interest of the display will change.

Figure 54:
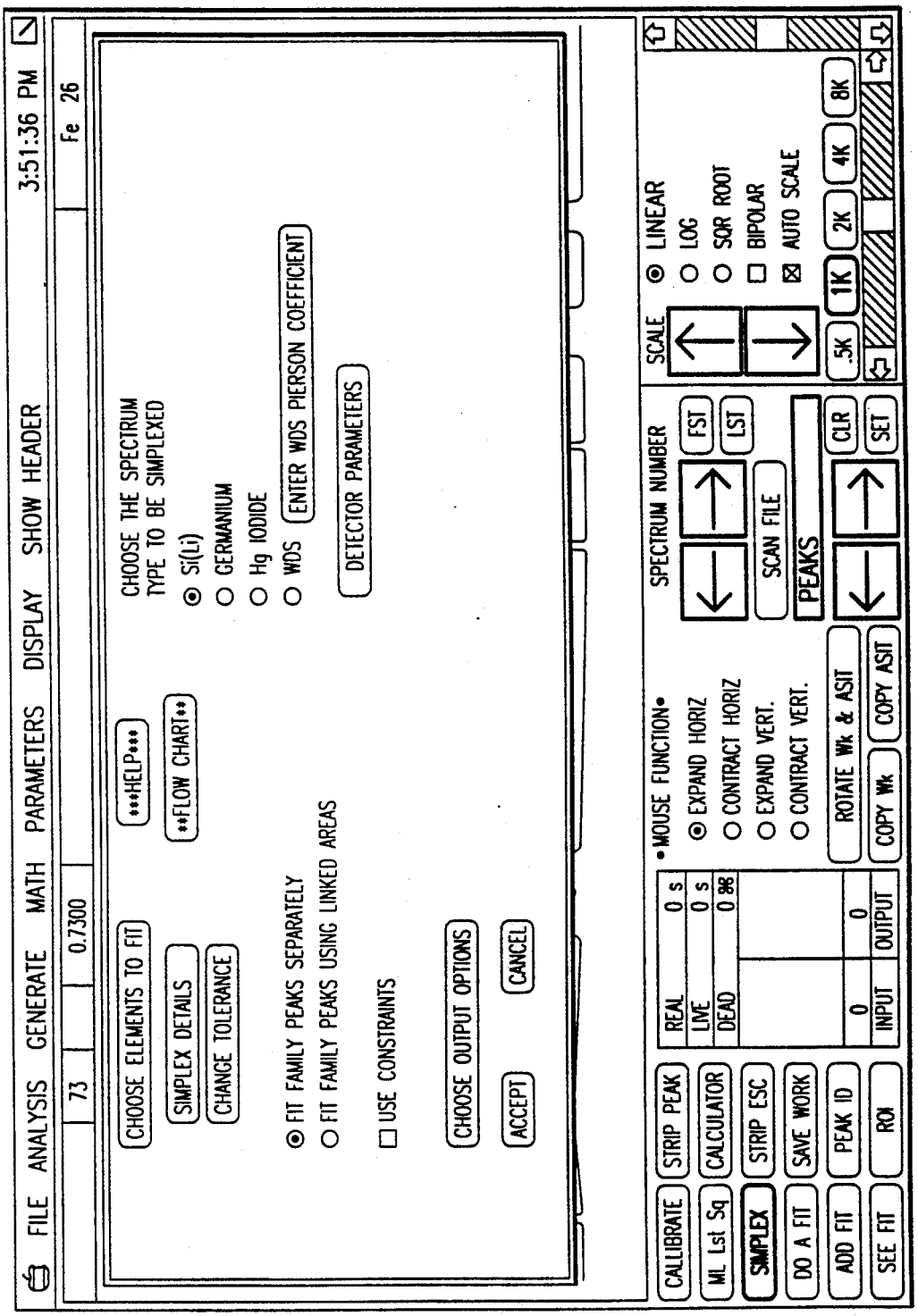
FIG. 54 illustrates a simplex setup dialogue interface.

FIG. 54 illustrates a simplex setup dialogue interface which is accessed from the choice "SIMPLEX" in the lower left hand corner of the display. This setup dialogue interface prepares the desk top spectrum analyzer to process spectra as illustrated in FIG. 8 element 186. Step 502 of FIG. 13 is preceded by this setup display interface.

Figure 55:
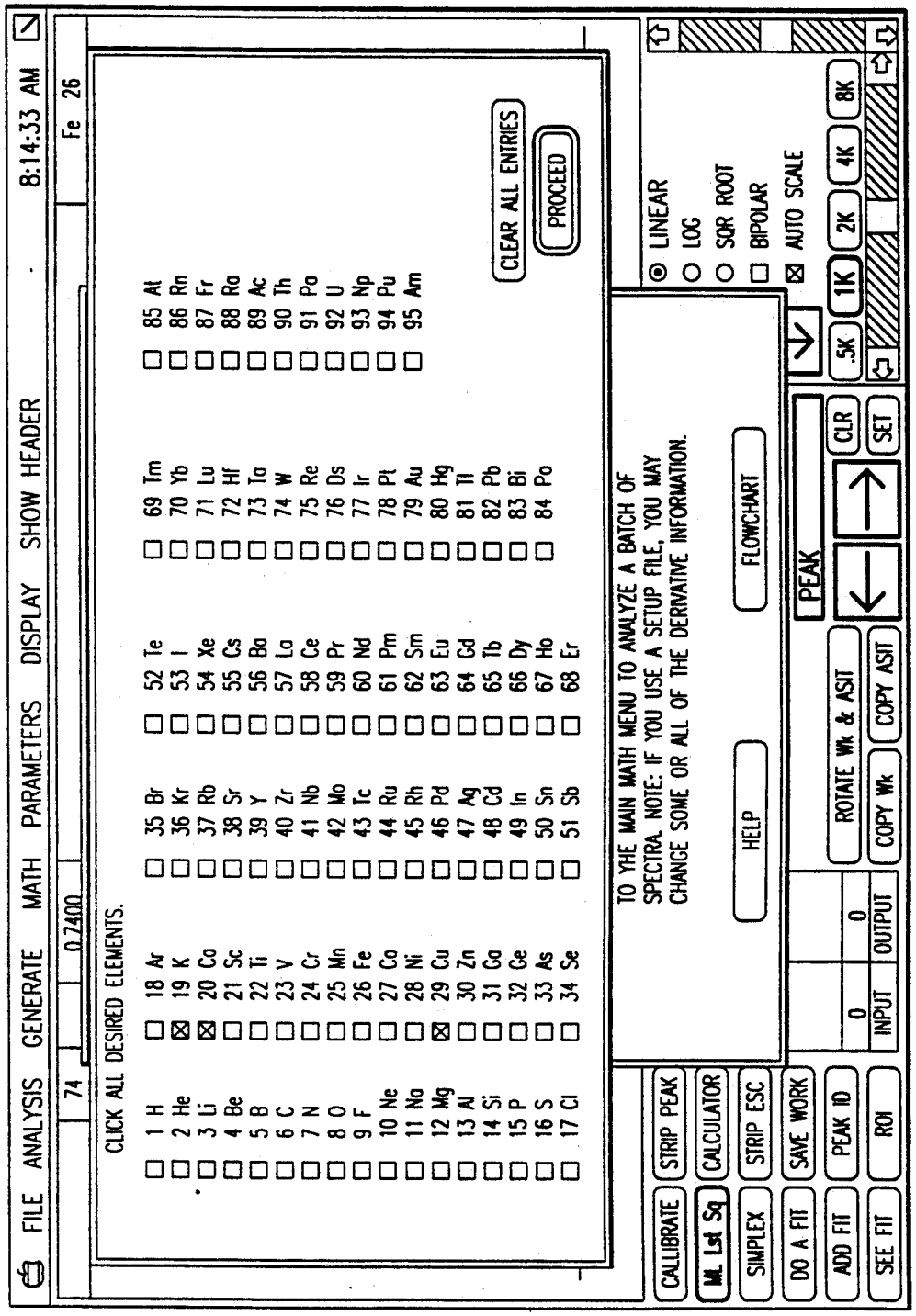
FIG. 55 illustrates a select elements dialogue interface.

FIG. 55 illustrates the dialogue interface used for selecting elements for either ML (multiple least squares regression) or simplex fitting, as selected in step 480 of FIG. 12, 508 of FIG. 13 or 788 of FIG. 19.

Figure 56:
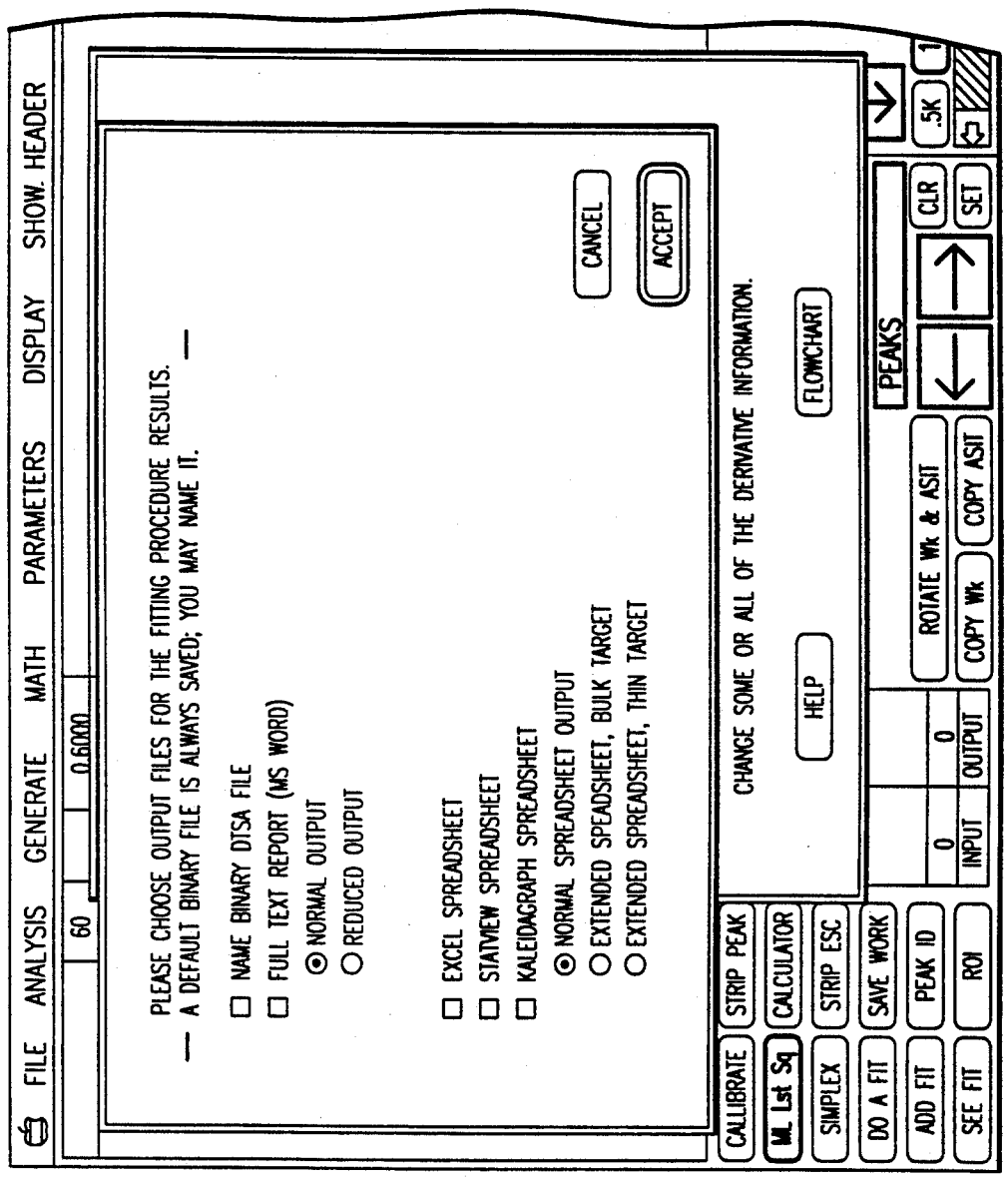
FIG. 56 illustrates an output options dialogue interface.

FIG. 56 illustrates the dialogue interface for selecting output options as indicated at step 410 of FIG. 10, step 514 of FIG. 13, step 794 of FIG. 19 and selection between steps 752, 754, 756 and 758 of FIG. 18.

FIG. 56 illustrates an output option dialogue interface for choosing output files for fitting procedure results. As indicated in the lower left hand corner of FIG. 56, the output options illustrated are for fitting results from a multiple linear least squares regression. It will be appreciated that this dialogue interface may be used for output files for results from simplex fitting.

Figure 57:
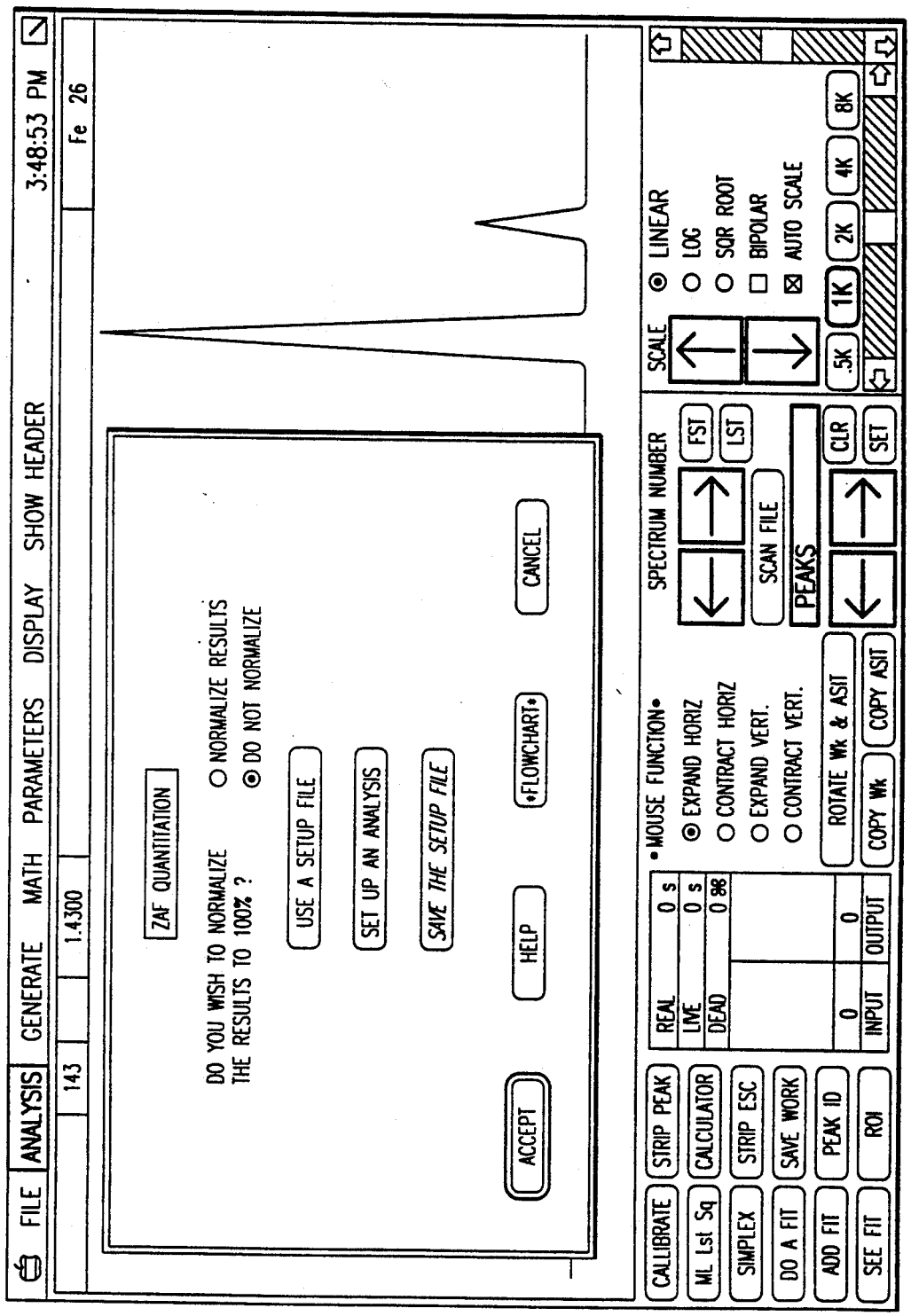
FIG. 57 illustrates a ZAF quantitization dialogue interface of the analysis submenu.

FIG. 57 illustrates the main dialogue interface for ZAF quantitization analysis as selected in step 616 of FIG. 15.

Figure 58:
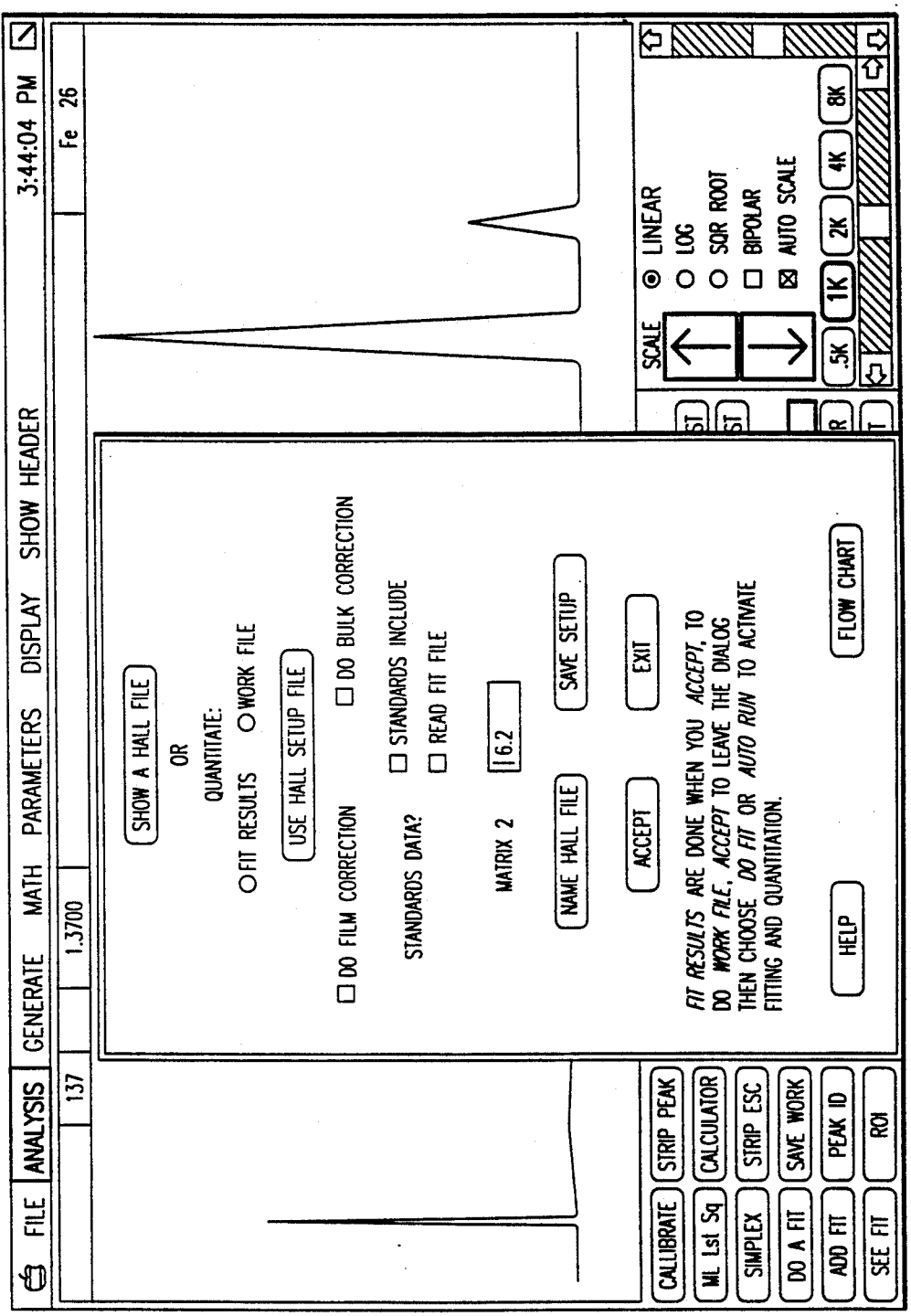
FIG. 58 illustrates a Hall bio-analysis dialogue interface of the analysis submenu.

FIG. 58 illustrates the main dialogue interface for Hall quantitization procedure as illustrated in step 644 of FIG. 16.

Figure 59:
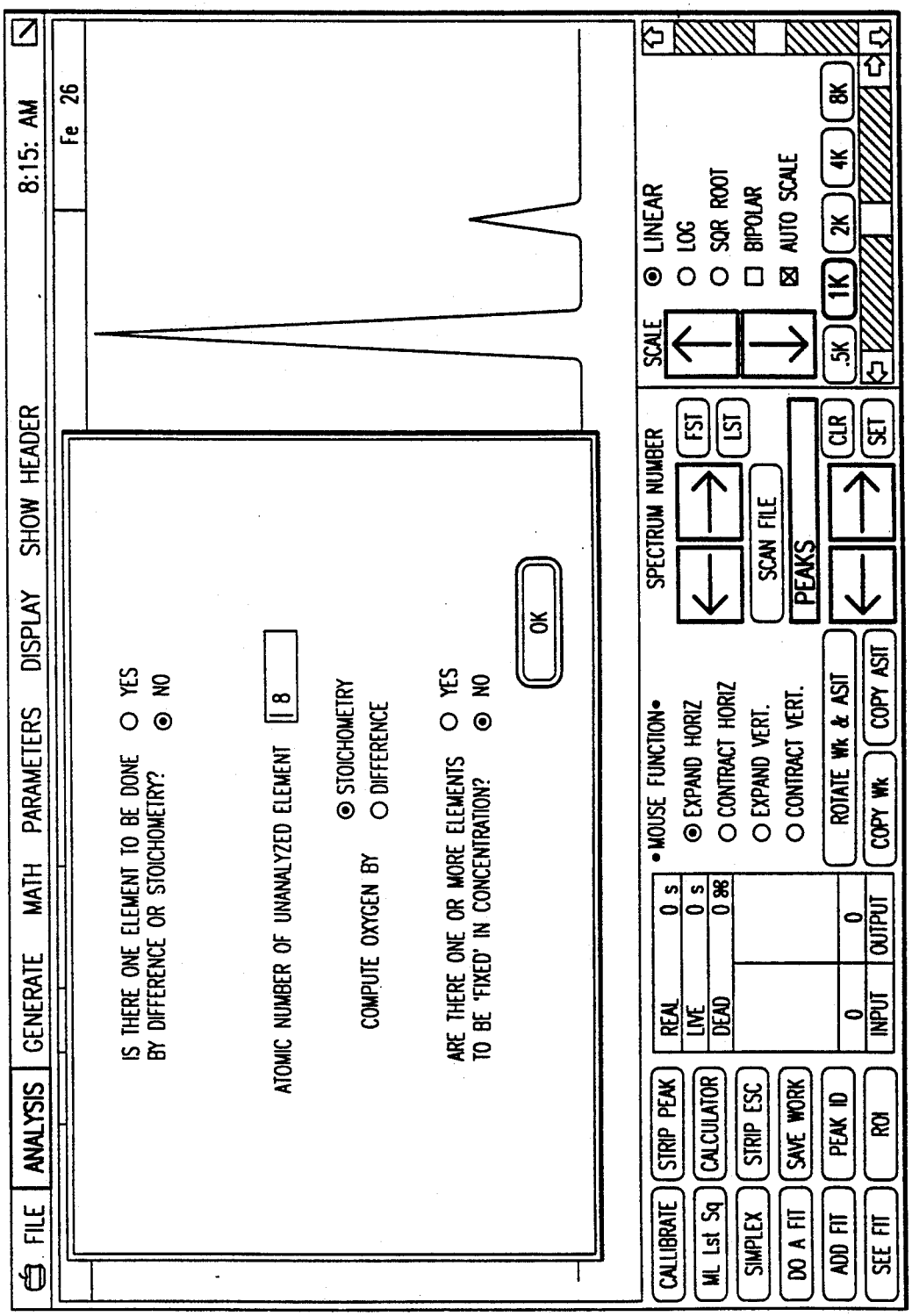
FIG. 59 illustrates a standardless ZAF analysis dialogue of the analysis submenu.

FIG. 59 illustrates a dialogue interface which appears after the ZAF quantitization dialogue interface illustrated in FIG. 57. The dialogue interface illustrated in FIG. 59 permits the user to define an unanalyzed element as indicated in step 742 of FIG. 18.

Figure 60:
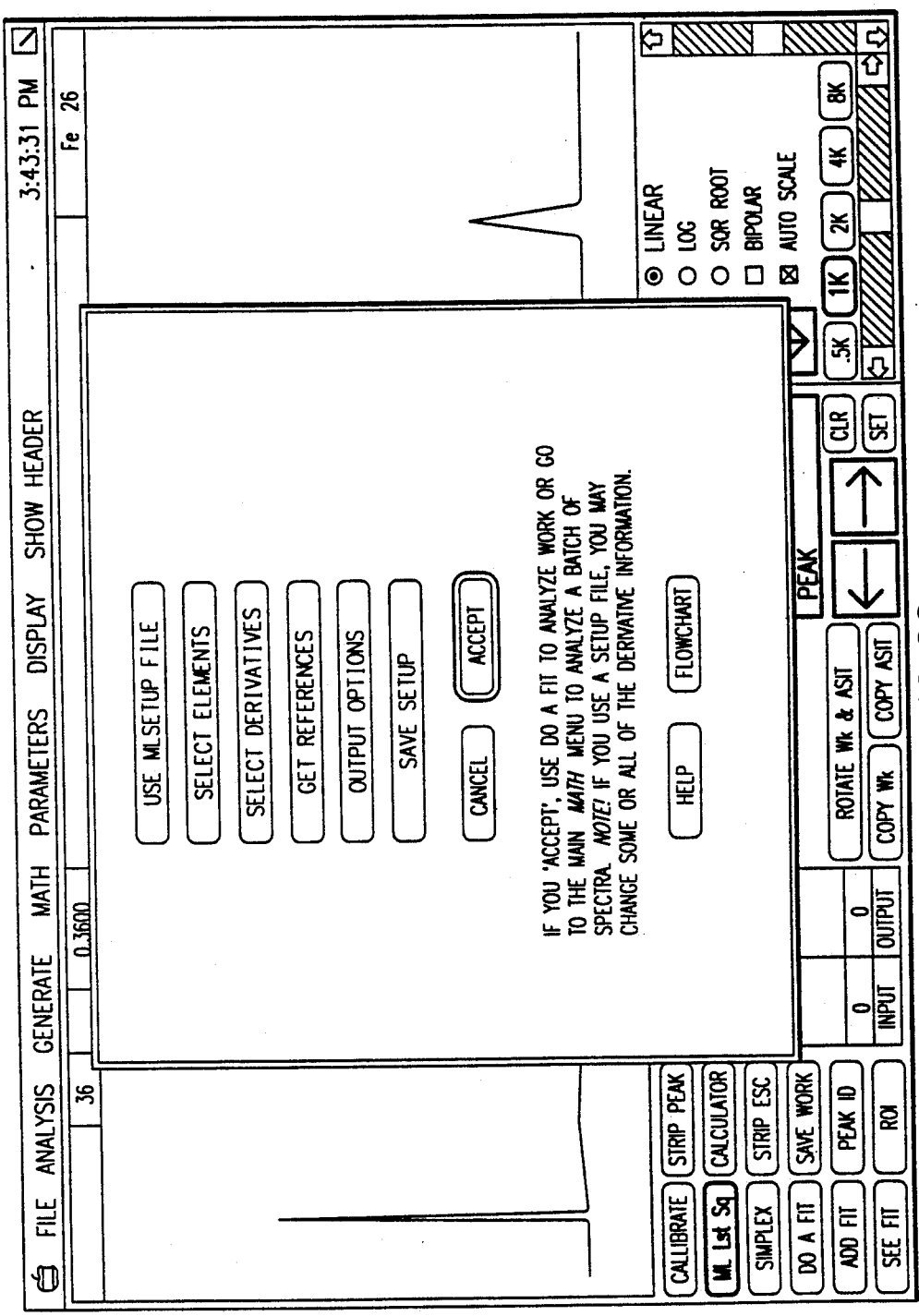
FIG. 60 illustrates the setup interface dialogue for multiple linear least squares analysis.

FIG. 60 illustrates a setup dialogue interface for multiple linear least squares regression, the process indicated by element 184 of FIG. 8 and step 782 of FIG. 19.

Figure 61:
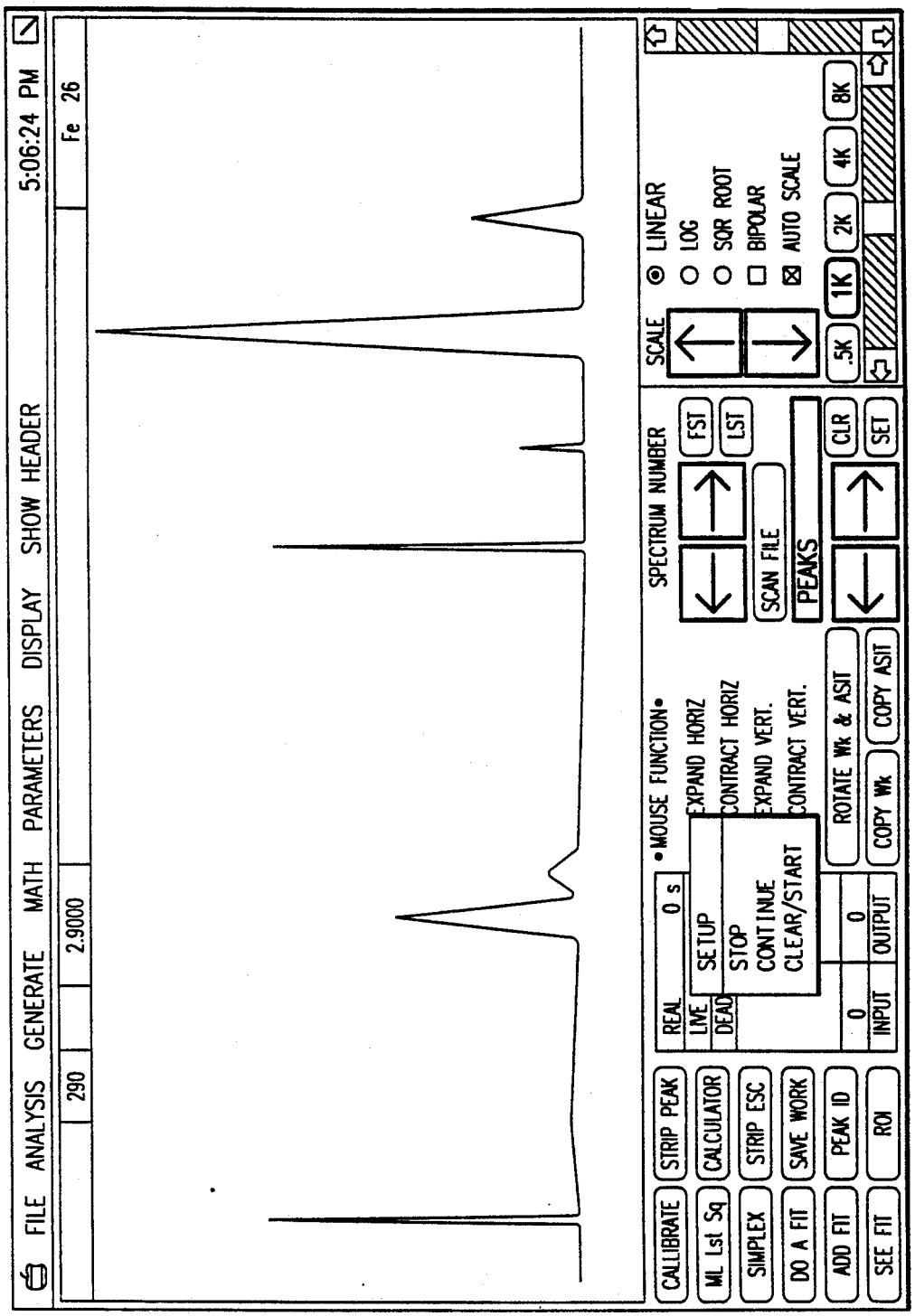
FIG. 61 illustrates the control dialog interface for NuBus-based spectrum acquisition.

FIG. 61 illustrates the sub dialogue, accessed from the spectrum acquisition status "meter" of FIG. 29, to control spectrum acquisition based on a NuBus card.

Figure 62:
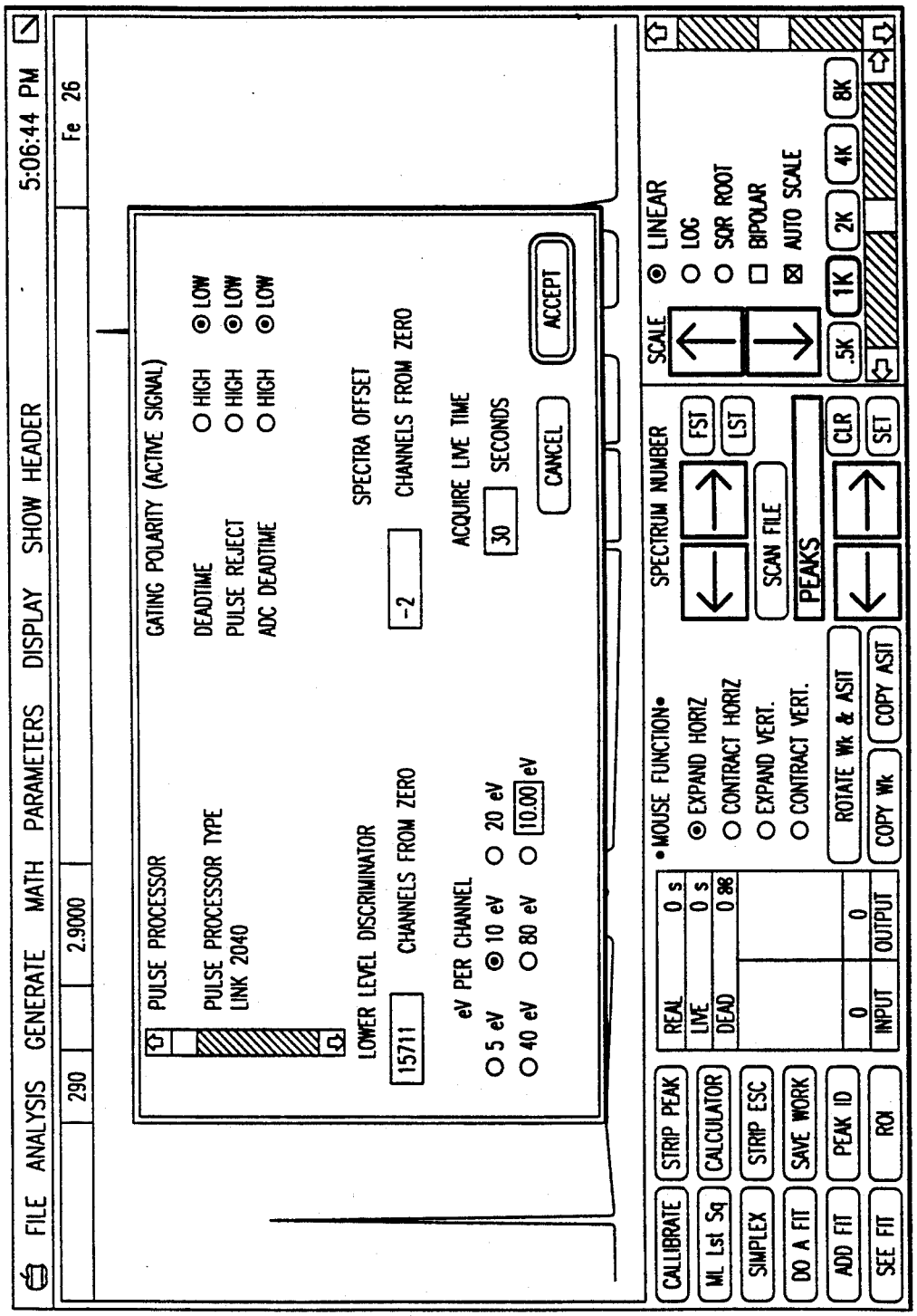
FIG. 62 illustrates the acquisition parameter sub-dialog interface for NuBus-based spectrum acquisition.

FIG. 62 illustrates a sub dialogue of the control dialog of FIG. 61 whereby the user inputs the acquisition parameters for spectrum acquisition based on a NuBus card.

It will be apparent to persons skilled in the art that the spectrum analyzer so described affords the analyst the ability to generate theoretical spectra from first principles so as to take into account the various detector characteristics and experimental geometries that affect the detected spectrum distribution, and to simplify the spectrum quantitation process and the determination of minimum detectable limits. It will be appreciated that a unique feature provided by the spectrum generation function of the spectrum analyzer is the option to plot, in any one of a plurality of overlapping displays, the spectrum at any step in the generation/detection process, or annotate and plot important physical parameters as a function of appropriate variables. Accordingly, the analyst will be able to quickly modify and observe the effect of a new parameter value on the selected distributions at each interaction in the process so that the analyst is better able to understand the physics that result in the detected spectrum distribution. The spectrum analyzer is suitable for desktop operation and receives transfers of spectra data from a plurality of commercial x-ray systems. This feature permits both the spectra from many systems and the quantitative results of processing to be directly compared, and evaluations made of the performance of various electron column-acquisition systems. While the analyst studies the spectra at his own desk, time is freed on the electron column-commercial analyzer system in the laboratory. The spectrum analyzer generates a theoretical spectrum according to input parameter values important to physical characteristics of a number of types of x-ray detectors. This unique feature permits comparison of an experimentally acquired spectrum using a new detector with a theoretically generated spectrum using the manufacturer's specifications of the new detector. In this way the analyst can determine whether the detector meets the manufacturer's specification, diagnose problems such as contamination on the detector window, and determine if the detector has been degraded by any other factor. The spectrum analyzer stores in a preference file a set of parameters values particular to the experimental conditions. The same parameter values are used to generate theoretical characteristic peak distributions. A plurality of such distributions, corresponding to a plurality of constituent elements to be studied in a specimen, are generated and stored to be used as reference distributions to perform quantitative analysis using very rapid multiple linear regression methods. This feature obviates the need to perform laboratory experiments to acquire reference spectra from pure elements under the conditions used for measuring the specimen, thereby eliminating the time consuming acquisition of spectra with very good statistical characteristics. The spectrum analyzer imports spectra acquired with a wavelength dispersive x-ray analyzer and converts the spectra to an energy dependent distribution. This feature permits wavelength dispersive spectrometer data to be analyzed with the same procedures used for energy distribution spectrometer data. The spectrum analyzer permits an analyst to deduct from an acquired spectrum a reference spectrum properly scaled so as to reveal remaining constituent elements in the acquired spectrum. This feature permits small overlapped peaks or background under the peak to be observed without interference and is an important tool for qualitative analysis. The features of the present invention have been described with reference to x-ray spectra generated with an electron beam. It will be appreciated that the invention described herein is also applicable to x-ray fluorescence spectra with appropriate changes well known to persons of ordinary skill in this art.

Having described a preferred embodiment of a novel spectrum analyzer, it is obvious that other modifications and variations will be suggested to those skilled in the art in light of the above teachings. It is therefore to be understood that changes may be made in the particular embodiment of the invention disclosed which are within the full intended scope of the invention as defined by the appended claims.

Having thus described the invention with the details and particularity required by the patent laws, what is claimed and desired protected by letters patent is set forth in the following claims.

What is claimed is:

1. A spectrum analyzer system comprising:
   a spectrum analyzer;
   a data interface means for porting spectra data from an x-ray acquisition system to said spectrum analyzer; and
   output interface means driven by said spectrum analyzer for providing output data in a desired form;

wherein said spectrum analyzer comprises:
a microcomputer means comprising processing means for processing spectra data according to a selected one of a plurality of control modes and a controlling means for selectively configuring the processing means for processing said spectra data according to said selected control mode,
operator interface means comprising keyboard-/mouse means for receiving commands from an operator to set said selected control mode, and display means for displaying at least one of said selected control mode and spectra data processed according to said control mode,
storage means connected to said microcomputer means for storing at least spectra data,
input device means connected to said microcomputer means for receiving said data interface means, and
output device means connected to said microcomputer means for driving said output interface means; and
wherein said display means comprises:
overlay means for forming an overlaid image from a plurality of spectra so that each spectrum of said plurality of spectra is distinguishable,
annotation means for marking points in and labeling said overlaid image, and
display apparatus for displaying said marked and labeled overlaid image to said operator.

2. The spectrum analyzer system of claim 1 wherein said processing means transfers a selected spectrum from said storage means to said overlay means of said display means according to a command from said operator interface means.

3. The spectrum analyzer system of claim 1 wherein said processing means deletes a selected spectrum from said overlay means according to a command from said operator interface means.

4. The spectrum analyzer system of claim 1 wherein said overlay means forms said overlay image of said plurality of spectra wherein each of said spectrum comprises a plurality of channels, each channel having an amplitude.

5. A control system emulating an x-ray spectrum generation and analyzing system on a computer, the computer comprising:
a controller;
data input means for inputting data to the computer;
data output means for outputting data from the computer;
interface means for connecting the data input means and data output means to the controller; and
memory means for storing data;
wherein the controller comprises;
experimental apparatus emulation means for emulating operating characteristics of an experimental apparatus, including operating characteristics of an incident exciting beam,
experimental geometry emulation means for emulating geometrical relationships between elements of the emulated experimental apparatus,
material sample emulation means for emulating physical properties of an experimental material sample,
physics equations selecting means for emulating physical interactions of the emulated material sample and the incident exciting beam of the emulated experimental apparatus, and
data generating means for generating theoretical x-ray spectrum data based on the emulated experimental apparatus, the emulated geometrical relationships and the emulated material sample and the emulated physical interactions.

6. The control system of claim 5, wherein the data input means comprises at least one of an actual experimental apparatus, a keyboard, a mouse, a hard drive, a disk drive, and a remote computer.

7. The control system of claim 5, wherein the data output means comprises at least one of a video display, a plotter, and a printer.

8. The control system of claim 5, wherein the memory means comprises at least one of a RAM, a ROM, a hard drive, a disk drive, and a remote computer.

9. The control system of claim 5, wherein the emulated experimental apparatus comprises:
an incident exciting beam generator;
at least one resulting photon detector; and
a material sample.

10. The control system of claim 9, wherein the incident exciting beam generator generates an electron beam, and wherein the resulting photon detector detects x-ray photons emitted by the emulated material sample.

11. The control system of claim 9, wherein the physical characteristics emulated by the experimental apparatus emulation means comprise:
an operating energy range of the emulated incident exciting beam generator;
operating characteristics of the at least one emulated detector; and
physical dimensions of the emulated material sample.

12. The control system of claim 9, wherein the geometrical relationships emulated by the experimental geometry emulating means comprises:
relative positioning between the material sample and the incident exciting beam generator;
an orientation of the emulated material sample;
relative positioning between the emulated material sample and the at least one emulated detector; and
an orientation of the at least one emulated detector.

13. The control system of claim 5, wherein the controller further comprises data conditioning means for conditioning the generated theoretical spectrum data.

14. The control system of claim 13, wherein the data conditioning means conditions the generated theoretical spectrum data by at least one of scaling, summing, filtering, differentiating, integrating, background removing and parsing.

15. The control system of claim 5, wherein the controller further comprises emulation altering means for altering at least one element of the emulated experimental apparatus, the emulated physical characteristics, the emulated experimental geometry, the emulated material sample, the emulated physical properties and the emulated physical interactions.

16. The control system of claim 5, wherein the controller further comprises data converting means for converting at least one of an actual spectrum data and the theoretical spectrum data between a wavelength dispersive spectrum and an energy-dispersive spectrum.

17. The control system of claim 5, wherein the controller further comprises data removal means for deleting data corresponding to a theoretical spectrum of the emulated material sample from an actual spectrum of a first material sample to create a parsed spectrum corresponding to the first material sample without the emulated material sample.

18. A method for generating a theoretical x-ray spectrum, comprising the steps of:
    emulating an actual experimental apparatus;
    emulating geometric relationships between elements of the actual experimental apparatus;
    emulating an experimental sample material;
    generating a theoretical spectrum data based on the emulated experimental apparatus, the experimental geometric relationships, the emulated experimental material sample and first principles; and
    displaying the generated theoretical spectrum.

19. The method of claim 18, wherein the step of emulating an actual experimental apparatus comprises the step of:
    emulating an incident exciting beam generator;
    emulating at least one resulting photon detector;
    emulating an operating energy range of the incident exciting beam generator;
    emulating operating characteristics of the at least one resulting photon detector;
    emulating physical characteristics of the emulated sample; and
    altering the emulated experimental apparatus in response to the generated theoretical spectrum.

20. The method of claim 19, wherein the step of emulating the geometric relationships comprises the steps of:
    emulating relative positions of the emulated incident exciting beam generator, the emulated experimental sample and the at least one emulated detector; and
    emulating orientations of the emulated material sample and the at least one emulated detector.

21. The method of claim 19, wherein the step of altering the experimental apparatus comprises the steps of:
    determining an experimental goal;
    generating the theoretical spectrum;
    determining if the generated theoretical spectrum is adequate based on the determined experimental goal; and
    altering the experimental apparatus based on discrepancies between the generated theoretical spectrum and the determined experimental goal.

22. The method of claim 19, wherein:
    the step of emulating an incident exciting beam generator comprises emulating an electron beam generator; and
    the step of emulating at least one resulting photon detector comprises emulating an x-ray photon detector.

* * * * *